United States Patent

Kim et al.

[11] Patent Number: 6,127,366
[45] Date of Patent: Oct. 3, 2000

[54] INHIBITORS OF FARNESYL-PROTEIN TRANSFERASE

[75] Inventors: Byeong M. Kim, Seoul, Rep. of Korea; Anthony W. Shaw, Lansdale, Pa.; Samuel L. Graham, Schwenksville, Pa.; S. Jane deSolms, Norristown, Pa.; Terrence M. Ciccarone, Telford, Pa.

[73] Assignee: Merck & Co., Inc., Rahway, N.J.

[21] Appl. No.: 09/166,271

[22] Filed: Oct. 5, 1998

Related U.S. Application Data

[62] Division of application No. 08/749,254, Nov. 15, 1996, Pat. No. 5,817,678.
[60] Provisional application No. 60/007,498, Nov. 22, 1995.
[51] Int. Cl.[7] ........................ A61K 31/535; C07D 413/06
[52] U.S. Cl. ........................ 514/235.5; 544/130
[58] Field of Search ........................ 514/235.5; 544/130

[56] References Cited

U.S. PATENT DOCUMENTS

| | | | |
|---|---|---|---|
| 3,038,835 | 6/1962 | Endres et al. | 514/330 |
| 5,141,851 | 8/1992 | Brown et al. | 435/15 |
| 5,238,922 | 8/1993 | Graham et al. | 514/18 |
| 5,326,773 | 7/1994 | deSolms et al. | 514/336 |
| 5,340,828 | 8/1994 | Graham et al. | 514/357 |
| 5,352,705 | 10/1994 | Deana et al. | 514/630 |
| 5,439,918 | 8/1995 | deSolms et al. | 514/307 |
| 5,468,733 | 11/1995 | deSolms et al. | 514/19 |
| 5,476,942 | 12/1995 | Lassale et al. | 546/210 |
| 5,478,934 | 12/1995 | Yuan et al. | 540/546 |
| 5,480,893 | 1/1996 | Graham et al. | 514/307 |
| 5,486,526 | 1/1996 | Durant et al. | 514/319 |
| 5,491,164 | 2/1996 | deSolms et al. | 514/423 |
| 5,504,212 | 4/1996 | deSolms et al. | 546/336 |
| 5,534,537 | 7/1996 | Ciccarone et al. | 514/397 |
| 5,571,835 | 11/1996 | Anthony et al. | 514/428 |
| 5,585,359 | 12/1996 | Breslin et al. | 514/19 |
| 5,686,472 | 11/1997 | Anthony et al. | 514/357 |
| 5,817,678 | 10/1998 | Kim et al. | 514/326 |

OTHER PUBLICATIONS

J. of Biol. Chem., vol. 268, No. 11, pp. 7617–7620 (1993), by J. B. Gibbs, et al.
J. of Biol. Chem., vol. 266, No. 24, pp. 15575–15578 (1991), by J. L. Goldstein, et al.
J. of Biol. Chem., vol. 369, No. 44, pp. 27705–27714 (1994), by G. L. James, et al.
Science, vol. 260, pp. 1937–1942 (1993), by G. L. James, et al.
J. of Biol. Chem., vol. 270, No. 11, pp. 6221–6226 (1995), by G. L. James, et al.
Science, vol. 260, pp. 1934–1937 (1993), by N. E. Kohl, et al.
Proc. Natl. Acad. Sci. USA, Med. Sciences, vol. 91, pp. 9141–9145 (1994), by N. E. Kohl, et al.
Nature Medicine, vol. 1, No. 8 (1995), N.E. Kohl, et al.
Biochemistry, vol. 31, pp. 3800–3807 (1992), by D. L. Pompliano.
Cancer Research, vol. 55, pp. 5302–5309 (1995), by L. Sepp–Lorenzino, et al.
Exp. Opin. Ther. Patents, 5(12), pp. 1269–1285 (1995), by S. L. Graham.

*Primary Examiner*—Jane Fan
*Attorney, Agent, or Firm*—J. Antonio Garcia-Rivas; Mark R. Daniel

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

22 Claims, No Drawings

INHIBITORS OF FARNESYL-PROTEIN TRANSFERASE

This is a division of Ser. No. 08/749,254 filed Nov. 15, 1996, U.S. Pat. No. 5,817,678. This application claims domestic priority under 35 USC 119(e), 60/007,498 Nov. 22, 1995.

BACKGROUND OF THE INVENTION

The Ras protein is part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, Ann. Rev. Biochem. 62:851–891 (1993)). Mutated ras genes are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., Nature 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., Ann. Rev. Biochem. 61:355–386 (1992); W. R. Schafer and J. Rine, Ann. Rev. Genetics 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., J. Biol. Chem. 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., Science, 260:1934–1937 (1993) and G. L. James et al., Science, 260:1937–1942 (1993). Recently, it has been shown that an inhibitor of farnesyl-protein transferase blocks the growth of ras-dependent tumors in nude mice (N. E. Kohl et al., Proc. Natl. Acad. Sci U.S.A., 91:9141–9145 (1994) and induces regression of mammary and salivary carcinomas in ras transgenic mice (N. E. Kohl et al., Nature Medicine, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., Science 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., Cell, 62:81–88 (1990); Schaber et al., J. Biol. Chem., 265:14701–14704 (1990); Schafer et al., Science, 249:1133–1139 (1990); Manne et al., Proc. Natl. Acad. Sci USA, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., PNAS, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., Science, 260:1934–1937 (1993); Graham, et al., J. Med. Chem., 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It has recently been shown that farnesyl-protein transferase inhibitors are inhibitors of proliferation of vascular smooth muscle cells and are therefore useful in the prevention and therapy of arteriosclerosis and diabetic disturbance of blood vessels (JP H7-112930). It has also recently been disclosed that certain tricyclic compounds which optionally incorporate a piperidine moiety are inhibitors of FPTase (WO 95/10514, WO 95/10515 and WO 95/10516).

It is, therefore, an object of this invention to develop novel peptidomimetic compounds that do not have a thiol moiety, and that will inhibit farnesyl-protein transferase and thus, the post-translational farnesylation of proteins. It is a further object of this invention to develop chemotherapeutic compositions containing the compounds of this invention and methods for producing the compounds of this invention.

SUMMARY OF THE INVENTION

The present invention comprises peptidomimetic piperidine, 1,4-dihydropyridine and 1,2,3,4-tetrahydropyridine compounds which inhibit the farnesyl-protein transferase. Furthermore, these compounds differ from such heterocyclic compounds previously described as inhibitors of farnesyl-protein transferase with respect to the position of substituents about the nitrogen containing ring. Further contained in this invention are chemotherapeutic compositions containing these farnesyl transferase inhibitors and methods for their production.

The compounds of this invention are illustrated by the formulae A:

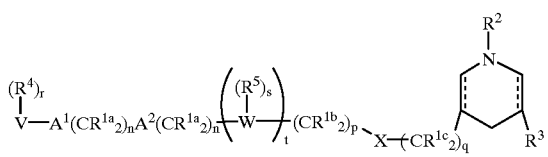

DETAILED DESCRIPTION OF THE INVENTION

The compounds of this invention are useful in the inhibition of farnesyl-protein transferase and the farnesylation of the oncogene protein Ras. In a first embodiment of this invention, the inhibitors of farnesyl-protein transferase are illustrated by the formula A:

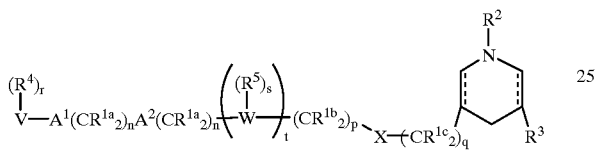

wherein:
$R^{1a}$, $R^{1b}$ and $R^{1c}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $NO_2$, $(R^8)_2N$—$C(NR^8)$—, $R^8C(O)$—, $R^8OC(O)$—, $N_3$, —$N(R^8)_2$, or $R^9OC(O)NR^8$—,
c) $C_1$–$C_6$ alkyl unsubstituted or substituted by unsubstituted or substituted aryl, heterocyclic, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)$—$NR^8$—;

$R^2$ is selected from: H; unsubstituted or substituted $C_{1-8}$ alkyl, unsubstituted or substituted $C_{2-8}$ alkenyl, unsubstituted or substituted aryl, unsubstituted or substituted heterocycle,

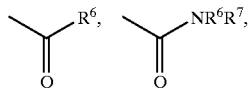

and —$SO(O)_2R^6$,
wherein the substituted group is substituted with one or more of:

1) aryl or heterocycle, unsubstituted or substituted with one or two groups selected from:
   a) $C_{1-4}$ alkyl,
   b) $(CH_2)_pOR^6$,
   c) $(CH_2)_pNR^6R^7$,
   d) halogen,
   e) $C_{1-4}$ perfluoroalkyl,
2) $C_{3-6}$ cycloalkyl,
3) $OR^6$,
4) $SR^6$, $S(O)R^6$, $SO_2R^6$,
5) —$NR^6R^7$,

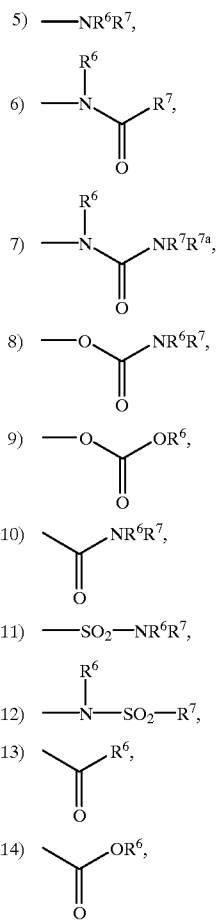

15) $C_{1-8}$ alkyl, or
16) $C_{1-8}$ perfluoroalkyl;
$R^3$ is selected from: H;

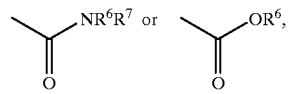

$R^4$ is independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, $NO_2$, $R^8_2N$—$C(NR^8)$—, $R^8C(O)$—, $R^8OC(O)$—, $N_3$, —$N(R^8)_2$, or $R^9OC(O)NR^8$—, and
c) $C_1$–$C_6$ alkyl unsubstituted or substituted by aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NH$—, CN, $H_2N$—$C(NH)$—, $R^8C(O)$—, $R^8OC(O)$—, $N_3$, —$N(R_8)_2$, or $R^8OC(O)NH$—;

$R^5$ is independently selected from:
a) hydrogen,
b) $C_2$–$C_6$ alkenyl, $C_2$–$C_6$ alkynyl, $C_3$–$C_6$ cycloalkyl, perfluoroalkyl, F, Cl, Br, $R^8O$—, $R^9S(O)_m$—, $R^8C(O)NR^8$—, CN, $NO_2$, $(R^8)_2N$—$C$—$(NR^8)$—, $R^8C(O)$—, $R^8OC(O)$—, $N_3$, —$N(R^8)_2$, or $R^9OC(O)NR^8$—, and c) $C_1$–$C_6$ alkyl, unsubstituted or substituted by perfluoroalkyl, F, Cl, Br, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$—, —$N(R^8)_2$, or $R^9OC(O)NR^8$—;

$R^6$, $R^7$ and $R^{7a}$ are independently selected from: H; $C_{1-4}$ alkyl, $C_{3-6}$ cycloalkyl, heterocycle, aryl, $C_{1-4}$ perfluoroalkyl, unsubstituted or substituted with one or two substituents selected from:

a) $C_{1-4}$ alkoxy, b) substituted or unsubstituted aryl or substituted or unsubstituted heterocycle, c) halogen, d) HO, e) 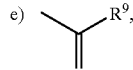

f) 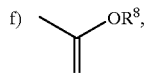

g) 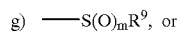

h) $N(R^8)_2$; or $R^6$ and $R^7$ may be joined in a ring;

$R^7$ and $R^{7a}$ may be joined in a ring;

$R^8$ is independently selected from hydrogen, $C_1$–$C_6$ alkyl, benzyl, 2,2,2-trifluoroethyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1-4}$ alkyl, unsubstituted or substituted $C_{3-6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:

a) $C_{1-4}$ alkoxy, b) aryl or heterocycle, c) halogen, d) HO, e) 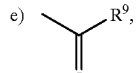

f) 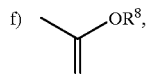

g) 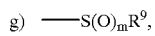

h) $N(R^8)_2$, or i) $C_{3-6}$ cycloalkyl;

$A^1$ and $A^2$ are independently selected from: a bond, —CH=CH—, —C≡C—, —C(O)—, —C(O)NR$^8$—, —NR$^8$C(O)—, O, —N(R$^8$)—, —S(O)$_2$N(R$^8$)—, —N(R$^8$)S(O)$_2$—, or S(O)$_m$;

V is selected from:

a) hydrogen, b) heterocycle, c) aryl, d) $C_1$–$C_{20}$ alkyl wherein from 0 to 4 carbon atoms are replaced with a a heteroatom selected from O, S, and N, and e) $C_2$–$C_{20}$ alkenyl, provided that V is not hydrogen if $A^1$ is S(O)$_m$ and V is not hydrogen if $A^1$ is a bond, n is 0 and $A^2$ is S(O)$_m$;

W is a heterocycle;

X is a bond, —C(=O)NR$^{10}$—, —NR$^{10}$C(=O)—, —S(O)$_m$—, —NR$^{10}$—, O or —C(=O)—;

| | |
|---|---|
| m is | 0, 1 or 2; |
| n is | 0, 1, 2, 3 or 4; |
| p is | 0, 1, 2, 3 or 4; |
| q is | 0, 1, 2, 3 or 4; |
| r is | 0 to 5, provided that r is 0 when V is hydrogen; |
| s is | 1 or 2; |
| t is | 0 or 1; and | the dashed lines represent optional double bonds;

or an optical isomer or a pharmaceutically acceptable salt thereof.

A preferred embodiment of the compounds of this invention is illustrated by the following formula:

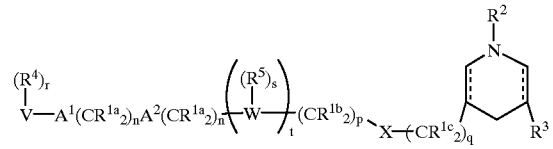

A wherein:

$R^{1a}$ and $R^{1c}$ are independently selected from: hydrogen, $C_3$–$C_{10}$ cycloalkyl, $R^8O$—, —N(R$^8$)$_2$, F or $C_1$–$C_6$ alkyl;

$R^{1b}$ is independently selected from:

a) hydrogen, b) unsubstituted or substituted aryl, unsubstituted or substituted heterocycle, $C_3$–$C_6$ cycloalkyl, $R^8O$—, —N(R$^8$)$_2$ or $C_2$–$C_6$ alkenyl, c) $C_1$–$C_6$ alkyl unsubstituted or substituted by unsubstituted or substituted aryl, heterocycle, $C_3$–$C_6$ cycloalkyl, $C_2$–$C_6$ alkenyl, $R^8O$—, or —N(R$^8$)$_2$;

$R^2$ is selected from:

a) $C_{1-8}$ alkyl, unsubstituted or substituted with one or more of:

1) aryl or heterocycle, unsubstituted or substituted with:
   i) $C_{1-4}$ alkyl,
   ii) $(CH_2)_pOR^6$,
   iii) $(CH_2)_pNR^6R^7$,
   iv) halogen,
   v) $C_{1-4}$ perfluoroalkyl,

2) OR$^6$,

3) SR$^6$, SO$_2$R$^6$, or

4) 

b) 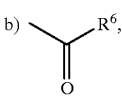

c) aryl, unsubstituted or substituted with one or more of:
   1) $C_{1-8}$ alkyl,
   2) $C_{1-8}$ perfluoroalkyl, 3) $OR^6$,
4) $SR^6$, $SO_2R^6$, or 5) 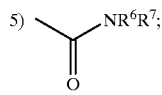 $NR^6R^7$;

d) —$SO_2R^6$, and e) 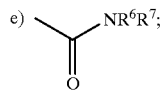 $NR^6R^7$;

$R^3$ is selected from: H;

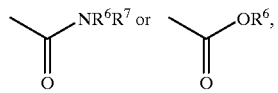 $NR^6R^7$ or $OR^6$, $R^4$ is independently selected from:
  a) hydrogen,
  b) $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and
  c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, $R^8OC(O)$—, —$N(R^8)_2$, or $R^9OC(O)NR^8$—;

$R^5$ is selected from:
  a) hydrogen,
  b) $C_2$–$C_6$ alkenyl, $C_2$–$C_6$ alkynyl, $C_3$–$C_6$ cycloalkyl, $C_1$–$C_6$ perfluoroalkyl, F, Cl, $R^8O$—, $R^9S(O)_m$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and
  c) $C_1$–$C_6$ alkyl unsubstituted or substituted by $C_1$–$C_6$ perfluoroalkyl, F, Cl, $R^8O$—, $R^9S(O)_m$—, $R^8C(O)NR^8$—, CN, $(R^8)_2N$—$C(NR^8)$—, $R^8C(O)$—, $R^8OC(O)$—, —$N(R^8)_2$, or $R^9OC(O)NR^8$—;

$R^6$, $R^7$ and $R^{7a}$ are independently selected from: H; $C_{1-4}$ alkyl, $C_{3-6}$ cycloalkyl, aryl, heterocycle, unsubstituted or substituted with:
  a) $C_{1-4}$ alkoxy,
  b) halogen, or
  c) substituted or unsubstituted aryl or substituted or unsubstituted heterocycle, $R^8$ is independently selected from hydrogen, $C_1$–$C_6$ alkyl, benzyl, 2,2,2-trifluoroethyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1-4}$ alkyl, unsubstituted or substituted $C_{3-6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:
  a) $C_{1-4}$ alkoxy,
  b) aryl or heterocycle,
  c) halogen,
  d) HO, e) 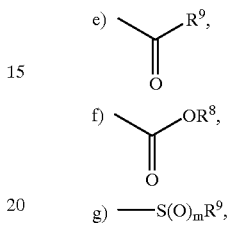 $R^9$, f) $OR^8$, g) —$S(O)_mR^9$, h) $N(R^8)_2$, or i) $C_{3-6}$ cycloalkyl;

$A^1$ and $A^2$ are independently selected from: a bond, —CH=CH—, —C≡C—, —C(O)—, —C(O)NR$^8$—, O, —N(R$^8$)—, or S(O)$_m$;

V is selected from:
  a) heterocycle selected from pyrrolidinyl, imidazolyl, pyridinyl, thiazolyl, pyridonyl, 2-oxopiperidinyl, indolyl, quinolinyl, isoquinolinyl, and thienyl, and
  b) aryl;

W is a heterocycle selected from pyrrolidinyl, imidazolyl, pyridinyl, thiazolyl, pyridonyl, 2-oxopiperidinyl, indolyl, quinolinyl, or isoquinolinyl;

X is a bond, —C(=O)NR$^{10}$—, —NR$^{10}$C(=O)—, —S(O)$_m$— or —NR$^{10}$—;

| | |
|---|---|
| m is | 0, 1 or 2; |
| n is | 0, 1, 2, 3 or 4; |
| p is | 1, 2 or 3; |
| q is | 0 or 1; |
| r is | 0 to 5, provided that r is 0 when V is hydrogen; |
| s is | 1 or 2; and |
| t is | 1; | or an optical isomer or a pharmaceutically acceptable salt thereof.

Another preferred embodiment of the compounds of this invention are illustrated by the formula B:

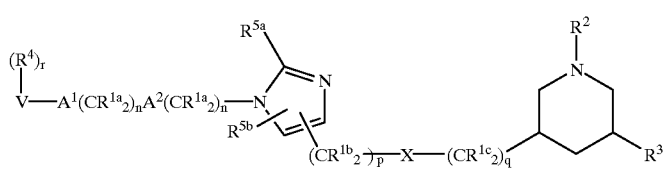

wherein:
$R^{1a}$ and $R^{1c}$ are independently selected from: hydrogen, $C_3$–$C_{10}$ cycloalkyl, $R^8O$—, —$N(R^8)_2$, F or $C_1$–$C_6$ alkyl;
$R^{1b}$ is independently selected from:

a) hydrogen, b) aryl, heterocycle, $C_3$–$C_{10}$ cycloalkyl, $R^8O$—, —$N(R^8)_2$, F or $C_2$–$C_6$ alkenyl, c) unsubstituted or substituted $C_1$–$C_6$ alkyl wherein the substituent on the substituted $C_1$–$C_6$ alkyl is selected from unsubstituted or substituted aryl, heterocycle, $C_3$–$C_{10}$ cycloalkyl, $C_2$–$C_6$ alkenyl, $R^8O$— and —$N(R^8)_2$;

$R^2$ is selected from: H; unsubstituted or substituted $C_{1-8}$ alkyl, unsubstituted or substituted $C_{2-8}$ alkenyl, unsubstituted or substituted aryl, unsubstituted or substituted heterocycle,

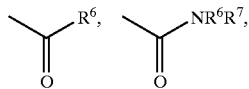

and —$S(O)_2R^6$, wherein the substituted group is substituted with one or more of:

1) aryl or heterocycle, unsubstituted or substituted with one or two groups selected from:
   a) $C_{1-4}$ alkyl,
   b) $(CH_2)_pOR^6$,
   c) $(CH_2)_pNR^6R^7$,
   d) halogen,
   e) $C_{1-4}$ perfluoroalkyl,
2) $C_{3-6}$ cycloalkyl,
3) $OR^6$,
4) $SR^6$, $S(O)R^6$, $SO_2R^6$,

5) —$NR^6R^7$,

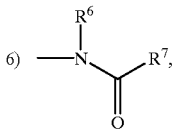

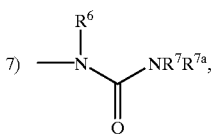

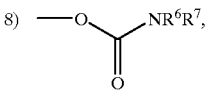

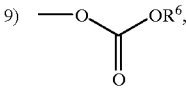

10) 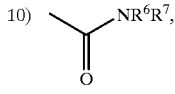

11) —$SO_2$—$NR^6R^7$,

12) 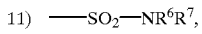

13) 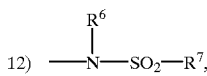

14) 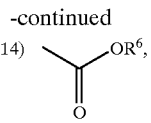

15) $C_{1-8}$ alkyl, or
16) $C_{1-8}$ perfluoroalkyl;

$R^3$ is selected from: H;

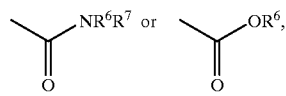

$R^4$ is independently selected from:
a) hydrogen,
b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, —$N(R^8)_2$, or $R^9OC(O)NR^8$—, and
c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, —$N(R^8)_2$, or $R^9OC(O)NR^8$—;

$R^{5a}$ and $R^{5b}$ are independently hydrogen, $C_1$–$C_6$ alkyl, cyclopropyl, trifluoromethyl and halogen;

$R^6$, $R^7$ and $R^{7a}$ are independently selected from: H; $C_{1-4}$ alkyl, $C_{3-6}$ cycloalkyl, aryl, heterocycle, unsubstituted or substituted with:
a) $C_{14}$ alkoxy,
b) halogen, or
c) substituted or unsubstituted aryl or substituted or unsubstituted heterocycle;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1-4}$ alkyl, unsubstituted or substituted $C_{3-6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:
a) $C_{1-4}$ alkoxy,
b) aryl or heterocycle,
c) halogen,
d) HO, e) 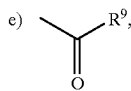

f) 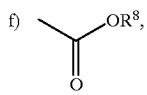

g) —$S(O)_mR^9$, h) $N(R^8)_2$, or
i) $C_{3-6}$ cycloalkyl;

$A^1$ and $A^2$ are independently selected from: a bond, —CH=CH—, —C≡C—, —C(O)—, —C(O)NR^8—, O, —N(R^8)—, or $S(O)_m$;

V is selected from:
 a) hydrogen,
 b) heterocycle selected from pyrrolidinyl, imidazolyl, imidazolinyl, pyridinyl, thiazolyl, pyridonyl, 2-oxopiperidinyl, oxazolyl, indolyl, quinolinyl, isoquinolinyl, triazolyl and thienyl,
 c) aryl,
 d) $C_1$–$C_{20}$ alkyl wherein from 0 to 4 carbon atoms are replaced with a a heteroatom selected from O, S, and N, and
 e) $C_2$–$C_{20}$ alkenyl, and
provided that V is not hydrogen if $A^1$ is $S(O)_m$ and V is not hydrogen if $A^1$ is a bond, n is 0 and $A^2$ is $S(O)_m$;
X is a bond, —C(=O)$NR^{10}$—, —$NR^{10}$C(=O)—, —$S(O)_m$— or —$NR^{10}$—;

| | |
|---|---|
| m is | 0, 1 or 2; |
| n is | 0, 1, 2, 3 or 4; |
| p is | 0, 1, 2, 3 or 4; |
| q is | 0 or 1; and | r is 0 to 5, provided that r is 0 when V is hydrogen;
or an optical isomer or pharmaceutically acceptable salt thereof.

Another preferred embodiment of the compounds of this invention are illustrated by the formula C:

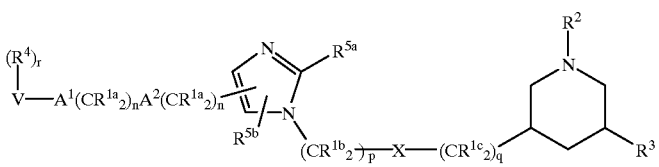

wherein:
$R^{1a}$ and $R^{1c}$ are independently selected from: hydrogen, $C_3$–$C_{10}$ cycloalkyl, $R^8O$—, —$N(R^8)_2$, F or $C_1$–$C_6$ alkyl;
$R^{1b}$ is independently selected from:
 a) hydrogen,
 b) aryl, heterocycle, $C_3$–$C_{10}$ cycloalkyl, $R^8O$—, —$N(R^8)_2$, F or $C_2$–$C_6$ alkenyl,
 c) unsubstituted or substituted $C_1$–$C_6$ alkyl wherein the substituent on the substituted $C_1$–$C_6$ alkyl is selected from unsubstituted or substituted aryl, heterocycle, $C_3$–$C_{10}$ cycloalkyl, $C_2$–$C_6$ alkenyl, $R^8O$— and —$N(R^8)_2$;
$R^2$ is selected from: H; unsubstituted or substituted $C_{1-8}$ alkyl, unsubstituted or substituted $C_{2-8}$ alkenyl, unsubstituted or substituted aryl, unsubstituted or substituted heterocycle,

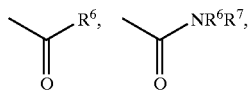

and —$S(O)_2R^6$,
wherein the substituted group is substituted with one or more of:
 1) aryl or heterocycle, unsubstituted or substituted with one or two groups selected from:
  a) $C_{1-4}$ alkyl,
  b) $(CH_2)_pOR^6$,
  c) $(CH_2)_pNR^6R^7$,
  d) halogen,
  e) $C_{1-4}$ perfluoroalkyl,
 2) $C_{3-6}$ cycloalkyl,
 3) $OR^6$,
 4) $SR^6$, $S(O)R^6$, $SO_2R^6$, 5) 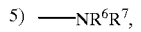 —$NR^6R^7$, 6) 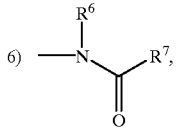

7) 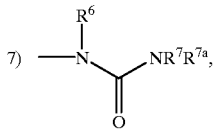

8) 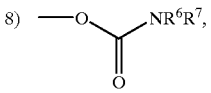

-continued

9) 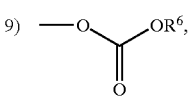

10) 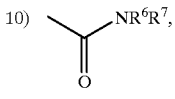

11) 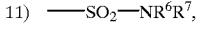 —$SO_2$—$NR^6R^7$,

12) 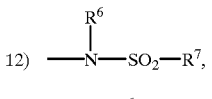

13) 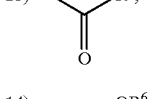

14) 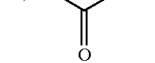

15) $C_{1-8}$ alkyl, or

16) $C_{1-8}$ perfluoroalkyl;

$R^3$ is selected from: H;

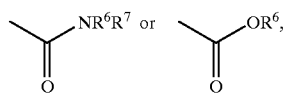

$R^4$ is independently selected from:
 a) hydrogen,
 b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, —$N(R^8)_2$, or $R^9OC(O)NR^8$—, and
 c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, —$N(R^8)_2$, or $R^9OC(O)NR^8$—;

$R^{5a}$ and $R^{5b}$ are independently hydrogen, $C_1$–$C_6$ alkyl, cyclopropyl, trifluoromethyl and halogen;

$R^6$, $R^7$ and $R^{7a}$ are independently selected from: H; $C_{1-4}$ alkyl, $C_{3-6}$ cycloalkyl, aryl, heterocycle, unsubstituted or substituted with:
 a) $C_{1-4}$ alkoxy,
 b) halogen, or
 c) substituted or unsubstituted aryl or substituted or unsubstituted heterocycle;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1-4}$ alkyl, unsubstituted or substituted $C_{3-6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:
 a) $C_{1-4}$ alkoxy,
 b) aryl or heterocycle,
 c) halogen,
 d) HO, e) 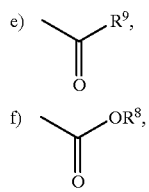

f) ![](OR8 group)

-continued
 g) —$S(O)_mR^9$,
 h) $N(R^8)_2$, or
 i) $C_{3-6}$ cycloalkyl;

$A^1$ and $A^2$ are independently selected from: a bond, —CH=CH—, —C≡C—, —C(O)—, —C(O)$NR^8$—, O, —$N(R^8)$—, or $S(O)_m$;

V is selected from:
 a) hydrogen,
 b) heterocycle selected from pyrrolidinyl, imidazolyl, imidazolinyl, pyridinyl, thiazolyl, pyridonyl, 2-oxopiperidinyl, oxazolyl, indolyl, quinolinyl, isoquinolinyl, triazolyl and thienyl,
 c) aryl,
 d) $C_1$–$C_{20}$ alkyl wherein from 0 to 4 carbon atoms are replaced with a a heteroatom selected from O, S, and N, and
 e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

X is a bond, —C(=O)$NR^{10}$—, —$NR^{10}C(=O)$—, —$S(O)_m$— or —$NR^{10}$—;

m is 0, 1 or 2;

n is 0, 1, 2, 3 or 4;

p is 0, 1, 2, 3 or 4, provided that p is not 0 if X is a bond, —$NR^8$— or O;

q is 0 or 1; and r is 0 to 5, provided that r is 0 when V is hydrogen;

or an optical isomer or pharmaceutically acceptable salt thereof.

In a more preferred embodiment of this invention, the inhibitors of farnesyl-protein transferase are illustrated by the formula D:

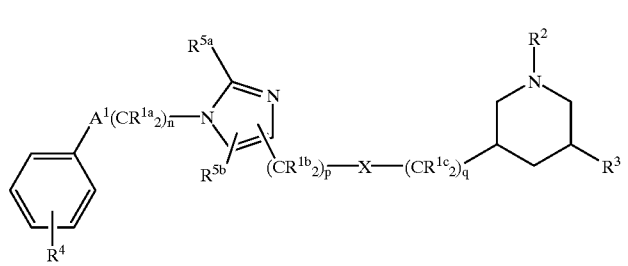

wherein:

$R^{1a}$ and $R^{1c}$ are independently selected from: hydrogen, $C_3$–$C_{10}$ cycloalkyl or $C_1$–$C_6$ alkyl;

$R^{1b}$ is independently selected from:
 a) hydrogen,
 b) aryl, heterocycle, $C_3$–$C_{10}$ cycloalkyl, $R^8O$—, —$N(R^8)_2$, F or $C_2$–$C_6$ alkenyl,
 c) $C_1$–$C_6$ alkyl unsubstituted or substituted by aryl, heterocycle, $C_3$–$C_{10}$ cycloalkyl, $C_2$–$C_6$ alkenyl, $R^8O$—, or —$N(R^8)_2$;

$R^2$ is selected from: H; unsubstituted or substituted $C_{1-8}$ alkyl, unsubstituted or substituted aryl,

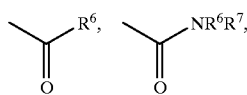

and —S(O)$_2$R$^6$, wherein the substituted group is substituted with one or more of:

1) aryl or heterocycle, unsubstituted or substituted with one or two groups selected from:
   a) C$_{1-4}$ alkyl,
   b) (CH$_2$)$_p$OR$^6$,
   c) (CH$_2$)$_p$NR$^6$R$^7$,
   d) halogen,
   e) C$_{1-4}$ perfluoroalkyl,
2) C$_{3-6}$ cycloalkyl,
3) OR$^6$,
4) SR$^6$, S(O)R$^6$, SO$_2$R$^6$,

5) —NR$^6$R$^7$,

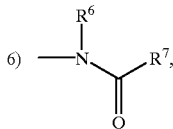

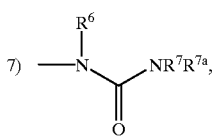

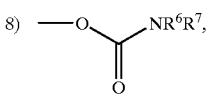

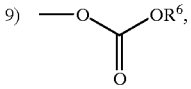

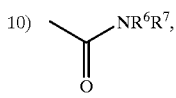

11) —SO$_2$—NR$^6$R$^7$,

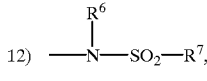

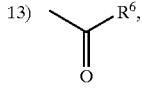

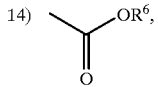

15) C$_{1-8}$ alkyl, or
16) C$_{1-8}$ perfluoroalkyl;

R$^3$ is selected from: H;

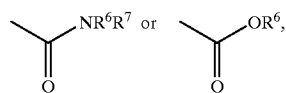

R$^4$ is independently selected from:
  a) hydrogen,
  b) aryl, substituted aryl, heterocycle, substituted heterocycle, C$_1$–C$_6$ alkyl, C$_2$–C$_6$ alkenyl, C$_2$–C$_6$ alkynyl, C$_1$–C$_6$ perfluoroalkyl, F, Cl, R$^8$O—, R$^8$C(O)NR$^8$—, CN, NO$_2$, (R$^8$)$_2$N—C(NR$^8$)—, R$^8$C(O)—, —N(R$^8$)$_2$, or R$^9$OC(O)NR$^8$—, and
  c) C$_1$–C$_6$ alkyl substituted by C$_1$–C$_6$ perfluoroalkyl, R$^8$O—, R$^8$C(O)NR$^8$—, (R$^8$)$_2$N—C(NR$^8$)—, R$^8$C(O)—, —N(R$^8$)$_2$, or R$^9$OC(O)NR$^8$—;

R$^{5a}$ and R$^{5b}$ are independently hydrogen, ethyl, cyclopropyl or methyl;

R$^6$, R$^7$ and R$^{7a}$ are independently selected from: H; C$_{1-4}$ alkyl, C$_{3-6}$ cycloalkyl, aryl, heterocycle, unsubstituted or substituted with:
  a) C$_{1-4}$ alkoxy,
  b) halogen, or
  c) substituted or unsubstituted aryl or substituted or unsubstituted heterocycle;

R$^8$ is independently selected from hydrogen, C$_1$–C$_6$ alkyl, 2,2,2-trifluoroethyl, benzyl and aryl;

R$^9$ is independently selected from C$_1$–C$_6$ alkyl and aryl;

R$^{10}$ is selected from: H; R$^8$C(O)—; R$^9$S(O)$_m$—; unsubstituted or substituted C$_{1-4}$ alkyl, wherein the substituted alkyl group is substituted with one or two substituents selected from:
  a) C$_{1-4}$ alkoxy,
  b) aryl or heterocycle,
  c) halogen,
  d) HO,

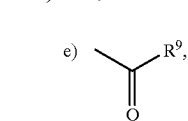

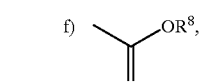

g) —S(O)$_m$R$^9$, h) N(R$^8$)$_2$, or
i) C$_{3-6}$ cycloalkyl;

A$^1$ is selected from: a bond, —C(O)—, O, —N(R$^8$)—, or S(O)$_m$;

X is a bond, —C(=O)NR$^{10}$—, —NR$^{10}$C(=O)—, —S(O)$_m$— or —NR$^{10}$—;

n is 0 or 1; provided that n is not 0 if A$^1$ is a bond, O, —N(R$^8$)—, or S(O)$_m$;

m is 0, 1 or 2;
p is 0, 1, 2, 3 or 4; and
q is 0 or 1;
or an optical isomer or pharmaceutically acceptable salt thereof.

In another more preferred embodiment of this invention, the inhibitors of farnesyl-protein transferase are illustrated by the formula E:

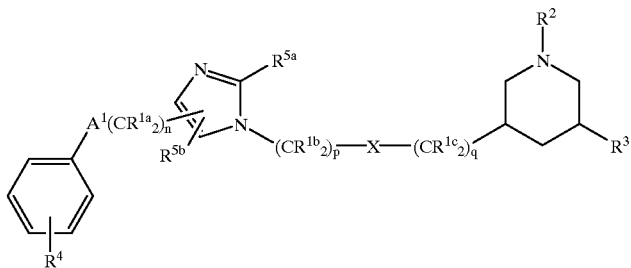

wherein:

$R^{1a}$ and $R^{1c}$ are independently selected from: hydrogen, $R^8O-$, $-N(R^8)_2$, F, $C_3-C_{10}$ cycloalkyl or $C_1-C_6$ alkyl;

$R^{1b}$ is independently selected from:
a) hydrogen,
b) aryl, heterocycle, $C_3-C_{10}$ cycloalkyl, $R^8O-$, $-N(R^8)_2$, F or $C_2-C_6$ alkenyl,
c) $C_1-C_6$ alkyl unsubstituted or substituted by aryl, heterocycle, $C_3-C_{10}$ cycloalkyl, $C_2-C_6$ alkenyl, $R^8O-$, or $-N(R^8)_2$;

$R^2$ is selected from: H; unsubstituted or substituted $C_{1-8}$ alkyl, unsubstituted or substituted aryl,

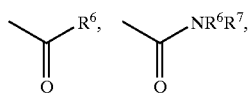

and $-S(O)_2R^6$, wherein the substituted group is substituted with one or more of:
1) aryl or heterocycle, unsubstituted or substituted with one or two groups selected from:
   a) $C_{1-4}$ alkyl,
   b) $(CH_2)_pOR^6$,
   c) $(CH_2)_pNR^6R^7$,
   d) halogen,
   e) $C_{1-4}$ perfluoroalkyl,
2) $C_{3-6}$ cycloalkyl,
3) $OR^6$,
4) $SR^6$, $S(O)R^6$, $SO_2R^6$, 5) 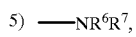—$NR^6R^7$, 6) 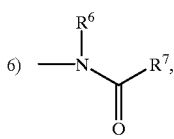

7) 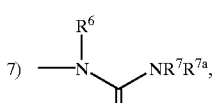

8) 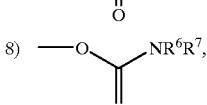

9) 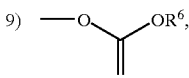

10) 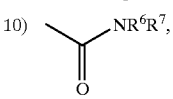

11) —$SO_2$—$NR^6R^7$,

12) 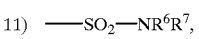

13) 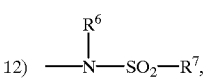

14) 

15) $C_{1-8}$ alkyl, or
16) $C_{1-8}$ perfluoroalkyl;

$R^3$ is selected from: H;

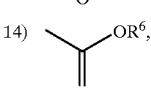

$R^4$ is independently selected from:
a) hydrogen,
b) aryl, substituted aryl, heterocycle, substituted heterocycle, $C_1-C_6$ alkyl, $C_2-C_6$ alkenyl, $C_2-C_6$ alkynyl, $C_1-C_6$ perfluoroalkyl, F, Cl, $R^8O-$, $R^8C(O)NR^8-$, CN, $NO_2$, $(R^8)_2N-C(NR^8)-$, $R^8C(O)-$, $-N(R^8)_2$, or $R^9OC(O)NR^8-$, and
c) $C_1-C_6$ alkyl substituted by $C_1-C_6$ perfluoroalkyl, $R^8O-$, $R^8C(O)NR^8-$, $(R^8)_2N-C(NR^8)-$, $R^8C(O)-$, $-N(R^8)_2$, or $R^9OC(O)NR^8-$;

$R^{5a}$ and $R^{5b}$ are independently hydrogen, ethyl, cyclopropyl or methyl;

$R^6$, $R^7$ and $R^{7a}$ are independently selected from: H; $C_{1-4}$ alkyl, $C_{3-6}$ cycloalkyl, aryl, heterocycle, unsubstituted or substituted with:
a) $C_{1-4}$ alkoxy,
b) halogen, or
c) substituted or unsubstituted aryl or substituted or unsubstituted heterocycle;

$R^8$ is independently selected from hydrogen, $C_1-C_6$ alkyl, 2,2,2-trifluoroethyl, benzyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1-4}$ alkyl, wherein the substituted alkyl group is substituted with one or two substituents selected from:

a) $C_{1-4}$ alkoxy, b) aryl or heterocycle, c) halogen, d) HO, e) 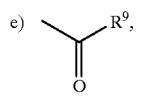

f) 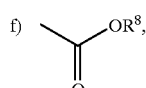

g) 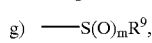

h) $N(R^8)_2$, or i) $C_{3-6}$ cycloalkyl;

X is a bond, —C(=O)NR$^{10}$—, —NR$^{10}$C(=O)—, —S(O)$_m$— or —NR$^{10}$—;

| | |
|---|---|
| n is | 0 or 1; |
| m is | 0, 1 or 2; |
| p is | 0, 1, 2, 3 or 4, provided that p is not 0 if X is a bond; —NR$^8$— or O; and |
| q is | 0 or 1; | or an optical isomer or pharmaceutically acceptable salt thereof.

In a further embodiment of this invention, the inhibitors of farnesyl-protein transferase are illustrated by the formula F:

F wherein:

$R^{1a}$ and $R^{1c}$ are independently selected from: hydrogen, $C_3$–$C_{10}$ cycloalkyl or $C_1$–$C_6$ alkyl;

$R^{1b}$ is independently selected from:

a) hydrogen, b) aryl, heterocycle, $C_3$–$C_{10}$ cycloalkyl, $R^8O$—, —$N(R^8)_2$ or F, c) $C_1$–$C_6$ alkyl unsubstituted or substituted by aryl, heterocycle, $C_3$–$C_{10}$ cycloalkyl, $R^8O$—, or —$N(R^8)_2$;

$R^2$ is selected from: H; unsubstituted or substituted $C_{1-8}$ alkyl, unsubstituted or substituted aryl,

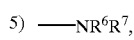

and —S(O)$_2R^6$, wherein the substituted group is substituted with one or more of:

1) aryl or heterocycle, unsubstituted or substituted with one or two groups selected from:

a) $C_{1-4}$ alkyl, b) $(CH_2)_pOR^6$, c) $(CH_2)_pNR^6R^7$, d) halogen, e) $C_{1-4}$ perfluoroalkyl, 2) $C_{3-6}$ cycloalkyl,

3) $OR^6$,

4) $SR^6$, $S(O)R^6$, $SO_2R^6$,

5) —$NR^6R^7$,

6) 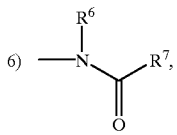

7) 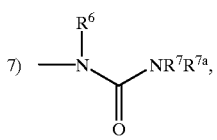

8) 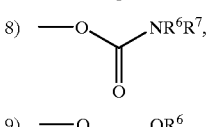

9) 

10) 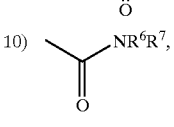

11) —$SO_2$—$NR^6R^7$,

12) 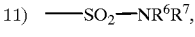

13) 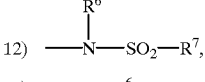

14) 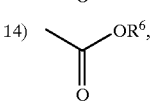

15) $C_{1-8}$ alkyl, or

16) $C_{1-8}$ perfluoroalkyl;

$R^3$ is selected from: H;

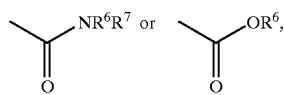

$R^{5a}$ and $R^{5b}$ are independently hydrogen, ethyl, cyclopropyl or methyl;

$R^6$, $R^7$ and $R^{7a}$ are independently selected from: H; $C_{1-4}$ alkyl, $C_{3-6}$ cycloalkyl, aryl, heterocycle, unsubstituted or substituted with:
a) $C_{1-4}$ alkoxy,
b) halogen, or
c) substituted or unsubstituted aryl or substituted or unsubstituted heterocycle;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1-4}$ alkyl, wherein the substituted alkyl group is substituted with one or two substituents selected from:
a) $C_{1-4}$ alkoxy,
b) aryl or heterocycle,
c) halogen,
d) HO, e) 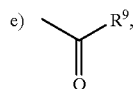

f) 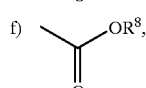

g) 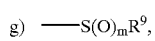

h) $N(R^8)_2$, or
i) $C_{3-6}$ cycloalkyl;

X is a bond, —C(=O)NR$^{10}$—, —NR$^{10}$C(=O)—, —S(O)$_m$— or —NR$^{10}$—;

| m is | 0, 1 or 2; |
| p is | 0, 1, 2, 3 or 4; and |
| q is | 0 or 1; | or an optical isomer or pharmaceutically acceptable salt thereof.

In a further embodiment of this invention, the inhibitors of farnesyl-protein transferase are illustrated by the formula G:

G

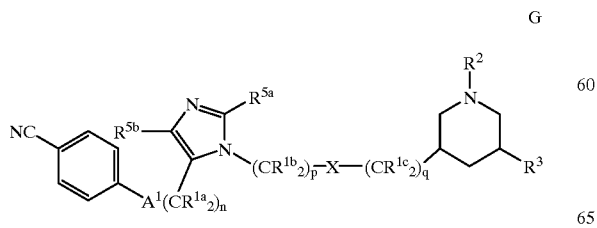

wherein:

$R^{1a}$ and $R^{1c}$ are independently selected from: hydrogen, $R^8O$—, —$N(R^8)_2$, F, $C_3$–$C_{10}$ cycloalkyl or $C_1$–$C_6$ alkyl;

$R^{1b}$ is independently selected from:
a) hydrogen,
b) aryl, heterocycle or $C_3$–$C_{10}$ cycloalkyl,
c) $C_1$–$C_6$ alkyl unsubstituted or substituted by aryl, heterocycle, $C_3$–$C_{10}$ cycloalkyl, $C_2$–$C_6$ alkenyl, $R^8O$—, or —$N(R^8)_2$;

$R^2$ is selected from: H; unsubstituted or substituted $C_{1-8}$ alkyl, unsubstituted or substituted aryl,

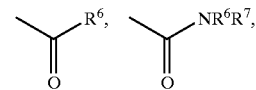

and —$S(O)_2R^6$, wherein the substituted group is substituted with one or more of:

1) aryl or heterocycle, unsubstituted or substituted with one or two groups selected from:
   a) $C_{1-4}$ alkyl,
   b) $(CH_2)_pOR^6$,
   c) $(CH_2)_pNR^6R^7$,
   d) halogen,
   e) $C_{1-4}$ perfluoroalkyl,
2) $C_{3-6}$ cycloalkyl,
3) $OR^6$,
4) $SR^6$, $S(O)R^6$, $SO_2R^6$,

5) —$NR^6R^7$,

6) 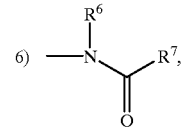

7) 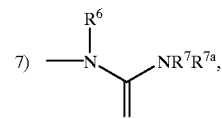

8) 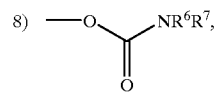

9) 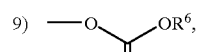

10) 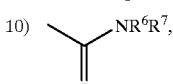

11) —$SO_2$—$NR^6R^7$,

12) 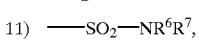

13) 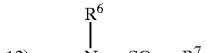

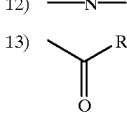

-continued

14) 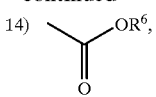

15) $C_{1-8}$ alkyl, or
16) $C_{1-8}$ perfluoroalkyl;

$R^3$ is selected from: H;

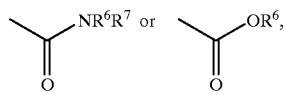

$R^{5a}$ and $R^{5b}$ are independently hydrogen, ethyl, cyclopropyl or methyl;

$R^6$, $R^7$ and $R^{7a}$ are independently selected from: H; $C_{1-4}$ alkyl, $C_{3-6}$ cycloalkyl, aryl, heterocycle, unsubstituted or substituted with:
 a) $C_{1-4}$ alkoxy,
 b) halogen, or
 c) substituted or unsubstituted aryl or substituted or unsubstituted heterocycle;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1-4}$ alkyl, wherein the substituted alkyl group is substituted with one or two substituents selected from:
 a) $C_{1-4}$ alkoxy,
 b) aryl or heterocycle,
 c) halogen,
 d) HO, e) 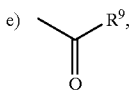

f) 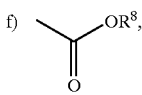

g) 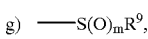

h) $N(R^8)_2$, or
 i) $C_{3-6}$ cycloalkyl;

$A^1$ is selected from: a bond, —C(O)—, O, —N($R^8$)—, or $S(O)_m$;

X is a bond, —C(=O)NR$^{10}$—, —NR$^{10}$C(=O)—, —S(O)$_m$— or —NR$^{10}$—;

| | |
|---|---|
| m is | 0, 1 or 2; |
| n is | 0 or 1; |
| p is | 1, 2 or 3; and |
| q is | 0 or 1; | or an optical isomer or pharmaceutically acceptable salt thereof.

The preferred compounds of this invention are as follows:

1-(t-Butoxycarbonyl)-cis-3-methoxycarbonyl-5-[N-(1-(4-cyanobenzyl-1H-imidazol-5-ylethyl)carbamoyl] piperidine 1-Phenethyl-cis-3-methoxycarbonyl-5-[N-(1-(4-cyanobenzyl)-1H-imidazol-5-ylethyl)carbamoyl] piperidine 1-(1-Naphthylmethyl)-cis-3-methoxycarbonyl-5-[N-(1-(4-cyanobenzyl-1H-imidazol-5-ylethyl)carbamoyl] piperidine 1-Benzyl-cis-3-methoxycarbonyl-5-[N-(1-(4-cyanobenzyl-1H-imidazol-5-ylethyl)carbamoyl]piperidine 1-Methyl-cis-3-methoxycarbonyl-5-[N-(1-(4-cyanobenzyl-1H-imidazol-5-ylethyl)carbamoyl]piperidine 1-(2-Indanyl)-cis-3-methoxycarbonyl-5-[N-(1-(4-cyanobenzyl-1H-imidazol-5-ylethyl)carbamoyl] piperidine 1-(2-Diphenylethyl)-cis-3-methoxycarbonyl-5- [N-(1-(4-cyanobenzyl-1H-imidazol-5-ylethyl)carbamoyl] piperidine 1-(3-Phenylpropyl)-cis-3-methoxycarbonyl-5-[N-(1-(4-cyanobenzyl-1H-imidazol-5-ylethyl)carbamoyl] piperidine 1-(2-Methylpropyl)-cis-3-methoxycarbonyl-5-[N-(1-(4-cyanobenzyl-1H-imidazol-5-ylethyl)carbamoyl] piperidine 1-Phenethyl-cis-3-carboxyl-5-[N-(1-(4-cyanobenzyl-1H-imidazol-5-ylethyl)carbamoyl]piperidine 1-Phenethyl-cis-3-[N-(1-morpholinyl)carbamyl]-5-[N-(1-(4-cyanobenzyl-1H-imidazol-5-ylethyl)carbamoyl] piperidine 1-Phenethyl-cis-3-[N-(benzyl)carbamyl]-5-[N-(1-(4-cyanobenzyl-1H-imidazol-5-ylethyl)carbamoyl] piperidine 1-Phenethyl-cis-3-[N-(cyclopropyl)carbamyl]-5-[N-(1-(4-cyanobenzyl-1H-imidazol-5-ylethyl)carbamoyl] piperidine 1-Phenethyl-cis-3-[N-(t-butyl)carbamyl]-5-[N-(1-(4-cyanobenzyl-1H-imidazol-5-ylethyl)carbamoyl] piperidine 1-(2,2-Diphenylethyl)-cis-3-[N-(1-morpholinyl)carbamyl]-5-[N-(1-(4-cyanobenzyl-1H-imidazol-5-ylethyl) carbamoyl]piperidine 1-(2,2-Diphenylethyl)-cis-3-[N-(t-butyl)carbamyl]-5-[N-(1-(4-cyanobenzyl-1H-imidazol-5-ylethyl)carbamoyl] piperidine N-[1-Phenethyl-cis-5-(N'-(4-cyanobenzyl-1-imidazol-5-ylethyl)carbamyl) piperidine-3-carbonyl]methionine methyl ester N-[1-Phenethyl-cis-5-(N'-(4-cyanobenzyl-1-imidazol-5-ylethyl)carbamyl) piperidine-3-carbonyl]methionine 1-(t-Butoxycarbonyl)-cis-3-methoxycarbonyl-5-[N-(1-(4-cyanobenzyl)-1H-imidazol-5-ylacetyl)amino]piperidine 1-Phenethyl-cis-3-methoxycarbonyl-5-[N-(1-(4-cyanobenzyl)-1H-imidazol-5-ylacetyl)amino]piperidine 1-Diphenylacetyl-cis-3-methoxycarbonyl-5-[N-(1-(4-cyanobenzyl-1H-imidazol-5-ylethyl)carbamoyl] piperidine 1-(t-Butoxycarbonyl)-trans-3-methoxycarbonyl-5-[N-(1-(4-cyanobenzyl)-1H-imidazol-5-ylethyl)carbamoyl]-piperidine 1-(2,2-Diphenylethyl)-3-[N-1-(4-cyanobenzyl)-1H-imidazol-5-ylethyl)carbamoyl]piperidine 1-(2,2-Diphenylethyl)-3(S)-[N-(1-(4-cyanobenzyl)-1H-imidazol-5-ylacetyl)amino]piperidine 1-(2,2-Diphenylethyl)-3(S)-[N-(1-(4-cyanobenzyl)-1H-imidazol-5-ylpropionyl)amino]piperidine 1-(2,2-Diphenylethyl)-3(S)-[N-(1-(4-cyanobenzyl)-1H-imidazol-5-ylcarbonyl)amino]piperidine 1-(Phenylacetyl)-3(S)-[N-(1-(4-cyanobenzyl)-1H-imidazol-5-ylethyl)carbamoyl]piperidine 1-(Diphenylacetyl)-3(S)-[N-(1-(4-cyanobenzyl)-1H-imidazol-5-ylethyl)carbamoyl]piperidine 1-(3-Chlorobenzoyl)-3(S)-[N-(1-(4-cyanobenzyl)-1H-imidazol-5-ylethyl)carbamoyl]piperidine 1-(2-(3-Chlorophenyl)-2-phenylethyl)-3(S)-[N-(1-(4-cyanobenzyl)-1H-imidazol-5-ylethyl)carbamoyl]piperidine 1-(Dibenzylsuberylmethyl)-3(S)-[N-(1-(4-cyanobenzyl)-1H-imidazol-5-ylethyl)carbamoyl]piperidine 1-(2-(3-Methylphenyl)-2-phenylethyl)-3(S)-[N-(1-(4-cyanobenzyl)-1H-imidazol-5-ylethyl)carbamoyl]piperidine 1-(2-(3-Trifluoromethylphenyl)-2-phenylethyl)-3(S)-[N-(1-(4-cyanobenzyl)-1H-imidazol-5-ylethyl)carbamoyl]piperidine 1-(2-(2-Chlorophenyl)-2-phenylethyl)-3(S)-[N-(1-(4-cyanobenzyl)-1H-imidazol-5-ylethyl)carbamoyl]piperidine 1-(2-(4-Chlorophenyl)-2-phenylethyl)-3(S)-[N-(1-(4-cyanobenzyl)-1H-imidazol-5-ylethyl)carbamoyl]piperidine 1-(2-(3-Aminomethylphenyl)-2-phenylethyl)-3(S)-[N-(1-(4-cyanobenzyl)-1H-imidazol-5-ylethyl)carbamoyl]piperidine 1-(2-Phenethyl)-3(S)-[N-(1-(4-cyanobenzyl)-1H-imidazol-5-ylethyl)carbamoyl]piperidine 1-(2-Phenethyl)-3-(R)-[N-(1-(4-cyanobenzyl)-1H-imidazol-5-ylethyl)carbamoyl]piperidine 1-(3-Phenylpropyl)-3(S)-[N-(1-(4-cyanobenzyl)-1H-imidazol-5-ylethyl)carbamoyl]piperidine 1-(2-Benzyl)-3-[N-(1-(4-cyanobenzyl)-1H-imidazol-5-ylethyl)carbamoyl]piperidine 1-(2-Chlorobenzyl)-3-[N-(1-(4-cyanobenzyl)-1H-imidazol-5-ylethyl)carbamoyl]piperidine 1-(3-Chlorobenzyl)-3-[N-(1-(4-cyanobenzyl)-1H-imidazol-5-ylethyl)carbamoyl]piperidine 1-(3-Chlorobenzyl)-3(S)-[N-(1-(4-cyanobenzyl)-1H-imidazol-5-ylethyl)carbamoyl]piperidine 1-(2,2-Diphenyl-2-hydroxyethyl)-3(S)-[N-(1-(4-cyanobenzyl)-1H-imidazol-5-ylethyl)carbamoyl]piperidine 1-(3-Methoxybenzyl)-3(S)-[N-(1-(4-cyanobenzyl)-1H-imidazol-5-ylethyl)carbamoyl]piperidine 1-(3,5-Dichlorobenzyl)-3(S)-[N-(1-(4-cyanobenzyl)-1H-imidazol-5-ylethyl)carbamoyl]piperidine 1-(3-Trifluoromethoxybenzyl)-3(S)-[N-(1-(4-cyanobenzyl)-1H-imidazol-5-ylethyl)carbamoyl]piperidine 1-(2,5-Dimethylbenzyl)-3(S)-[N-(1-(4-cyanobenzyl)-1H-imidazol-5-ylethyl)carbamoyl]piperidine 1-(3-Trifluoromethylbenzyl)-3(S)-[N-(1-(4-cyanobenzyl)-1H-imidazol-5-ylethyl)carbamoyl]piperidine 1-(3-Bromobenzyl)-3(S)-[N-(1-(4-cyanobenzyl)-1H-imidazol-5-ylethyl)carbamoyl]piperidine 1-(3-Methylbenzyl)-3(S)-[N-(1-(4-cyanobenzyl)-1-H-imidazol-5-ylethyl)carbamoyl]piperidine 1-Isobutyl-3(S)-[N-(1-(4-cyanobenzyl)-1H-imidazol-5-ylethyl)carbamoyl]piperidine 1-(2-Methyl-2-phenylethyl)-3-[N-(1-(4-cyanobenzyl)-1H-imidazol-5-ylethyl)carbamoyl]piperidine 1-(2-(1-Morpholinyl)-2-phenylethyl)-3(S)-[N-(1-(4-cyanobenzyl)-1H-imidazol-5-ylethyl)carbamoyl]piperidine 1-(2-(1-Piperidinyl)-2-phenylethyl)-3(S)-[N-(1-(4-cyanobenzyl)-1H-imidazol-5-ylethyl)carbamoyl]piperidine 1-(2,2-Diphenylethyl)-3(S)-[N-(1-(4-cyanobenzyl)-2-methyl-1H-imidazol-5-ylethyl)carbamoyl]piperidine 1-(2,2-Diphenylethyl)-3(S)-[N-(1-(4-methoxybenzyl)-1H-imidazol-5-ylethyl)carbamoyl]piperidine 1-(Diphenylmethyl)-3(S)-[N-(1-(4-cyanobenzyl)-1H-imidazol-5-ylethyl)carbamoyl]piperidine 1-(3-Methoxyphenethyl)-3(S)-[N-(1-(4-cyanobenzyl)-1H-imidazol-5-ylethyl)carbamoyl]piperidine 1-(1-Naphthylethyl)-3(S)-[N-(1-(4-cyanobenzyl)-1H-imidazol-5-ylethyl)carbamoyl]piperidine 1-(3-Chlorophenethyl)-3(S)-[N-1-(4-cyanobenzy)l-1H-imidazol-5-ylethyl)carbamoyl]piperidine 1-(α-Methylbenzyl)-3(S)-[N-(1-(4-cyanobenzyl)-1H-imidazol-5-ylethyl)carbamoyl]piperidine 1-(Diphenylmethyl)-3(S)-[N-(1-(4-cyanobenzyl)-2-methyl-1H-imidazol-5-ylethyl)carbamoyl]piperidine 1-(α-Toluenesulfonyl)-3(S)-[N-(1-(4-cyanobenzyl)-1H-imidazol-5-ylethyl)carbamoyl]piperidine 1-(Benzenesulfonyl)-3(S)-[N-(1-(4-cyanobenzyl)-1H-imidazol-5-ylethyl)carbamoyl]piperidine 1-(1-Naphthylenesulfonyl)-3(S)-[N-(1-(4-cyanobenzyl)-1H-imidazol-5-ylethyl)carbamoyl]piperidine 1-(3-Chlorobenzenesulfonyl)-3(S)-[N-(1-(4-cyanobenzyl)-1H-imidazol-5-ylethyl)carbamoyl]piperidine 1-(3,5-Dichlorobenzenesulfonyl)-3(S)-[N-(1-(4-cyanobenzyl)-1H-imidazol-5-ylethyl)carbamoyl]piperidine 1-(α-Toluenesulfonyl)-3-(R)-[N-(1-(4-cyanobenzyl)-1H-imidazol-5-ylethyl)carbamoyl]piperidine 1-(α-Toluenesulfonyl)-cis-3-methoxycarbonyl-5-[N-(1-(4-cyanobenzyl)-1H-imidazol-5-ylethyl)carbamoyl]piperidine 1-(Methanesulfonyl)-3(S)-[N-(1-(4-cyanobenzyl)-1H-imidazol-5-ylethyl)carbamoyl]piperidine 1-(Diphenylcarbamoyl)-3(S)-[N-(1-(4-cyanobenzyl)-1H-imidazol-5-ylethyl)carbamoyl]piperidine 1-(Phenylcarbamoyl)-3(S)-[N-(1-(4-cyanobenzyl)-1H-imidazol-5-ylethyl)carbamoyl]piperidine 1-[2-(2-Pyridyl)-2-phenyl-2-hydroxyethyl]-3(S)-[N-(1-(4-cyanobenzyl)-1H-imidazol-5-ylethyl)carbamoyl]piperidine 1-(2-Pyridylethyl)-3(S)-[N-(1-(4-cyanobenzyl)-1H-imidazol-5-ylethyl)carbamoyl]piperidine 1-Phenyl-3(S)-[N-(1-(4-cyanobenzyl)-H-imidazol-5-ylethyl)carbamoyl]piperidine 1-(3-Methylphenyl)-3(S)-[N-(1-(4-cyanobenzyl)-1H-imidazol-5-ylethyl)carbamoyl]piperidine 1-(2,2-Diphenylethyl)-3(S)-[2-(1-(4-cyanobenzyl)-1H-imidazol-5-yl)ethylthiomethyl]piperidine 1-(2,2-Diphenylethyl)-3(S)-[N-(1-(4-cyanobenzyl)-1H-imidazol-5-yl)ethylsulfonylmethyl]piperidine 1-(2,2-Diphenylethyl)-3(S)-[N-(1-(4-cyanobenzyl)-1H-imidazol-5-ylethyl)-N-methyl-carbamoyl]piperidine 1-(3-Bromobenzyl)-3(S)-[N-(1-(4-cyanobenzyl)-1H-imidazol-5-ylethyl) N-methyl-carbamoyl]piperidine 1-(2,2-Diphenylethyl)-3(S)-[N-(1-(4-cyanobenzyl)-1H-imidazol-5-ylethyl)aminomethyl]piperidine 1-(2,2-Diphenylethyl)-3(S)-[N-(1-(4-cyanobenzyl)-1H-imidazol-5-ylethyl)-N-acetyl-aminomethyl]piperidine 1-(2,2-Diphenylethyl)-3(S)-[N-(1-(4-cyanobenzyl)-2-methyl-1H-imidazol-5-ylethyl)-N-acetyl-aminomethyl]piperidine 1-(2,2-Diphenylethyl)-3(S)-[N-(1-(4-cyanobenzyl)-1H-imidazol-5-ylethyl)-N-cyclopropylmethyl-aminomethyl]piperidine 1-(2,2-Diphenylethyl)-3(S)-[N-(2-methyl-1H-imidazol-4-ylethyl)-N-(4-cyanobenzoyl)aminomethyl]piperidine 1-(2,2-Diphenylethyl)-3(S)-[5-(4-cyanobenzyl)-1H-imidazol-1-ylmethyl]piperidine 1-(2,2-Diphenylethyl)-3(S)-[5-(4-cyanobenzyl)-1H-imidazol-1-ylethylcarbamoyl]piperdine or an optical isomer or a pharmaceutically acceptable salt thereof.

Specific examples of the compounds of the invention are:

1-Phenethyl-cis-3-[N-(1-morpholinyl)carbamyl]-5-[N-(1-(4-cyanobenzyl-1H-imidazol-5-ylethyl)carbamoyl]piperidine

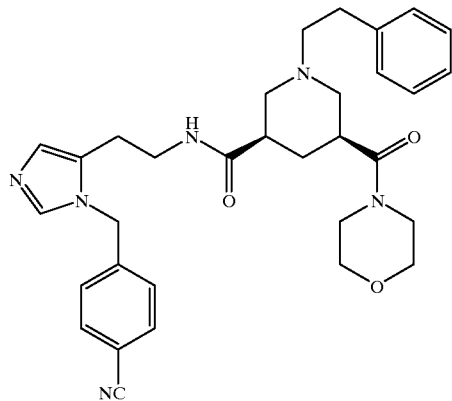

1-(2-Diphenylethyl)-cis-3-[N-(1-morpholinyl)carbamyl]-5-[N-(1-(4-cyanobenzyl-1H-imidazol-5-ylethyl)carbamoyl]piperidine

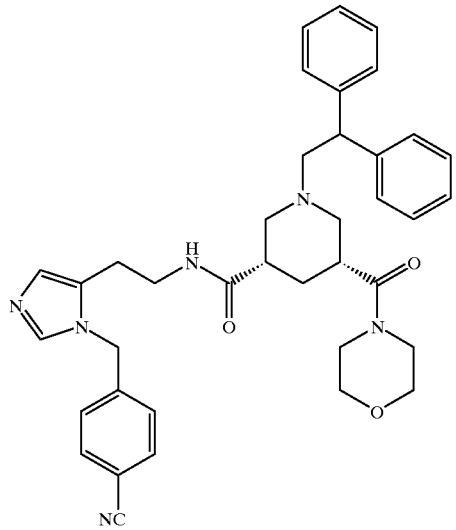

N-[1-Phenethyl-5-(N'-(4-cyanobenzyl-1-imidazol-5-ylethyl)carbamyl) piperidine-cis-3-carbonyl]methionine

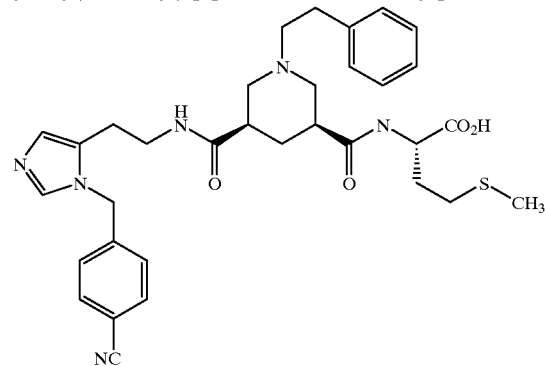

1-(2-Diphenylethyl)-3-methoxycarbonyl-5-[N-(1-(4-cyanobenzyl-1H-imidazole-cis-5-ethyl)carbamoyl]piperidine

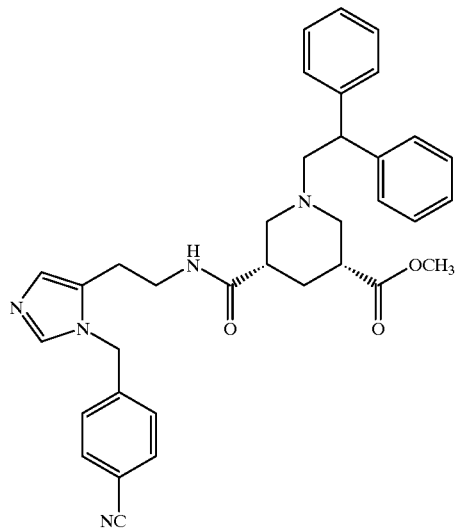

1-(2,2-Diphenylethyl)-cis-3-[N-(1-(4-cyanobenzyl)-1H-imidazol-5-ylethyl)carbamoyl]piperidine

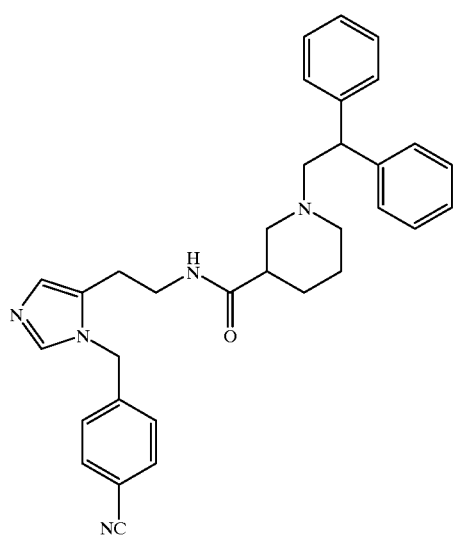

29
1-(3-Chlorobenzyl)-3-[N-(1-(4-cyanobenzyl)-1H-imidazol-5-ylethyl)carbamoyl]piperidine
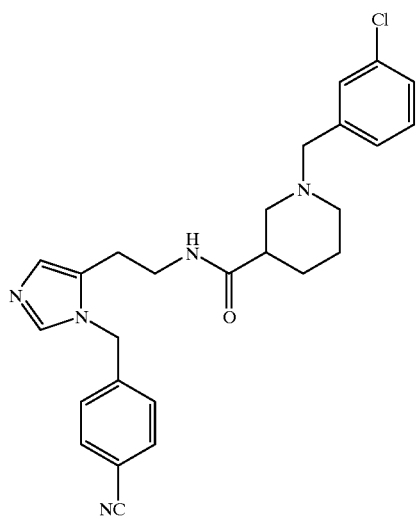
1-(2-(1-Morpholinyl)-2-phenylethyl)-3(S)-[N-(1-(4-cyanobenzyl)-1H-imidazol-5-ylethyl)carbamoyl]piperidine
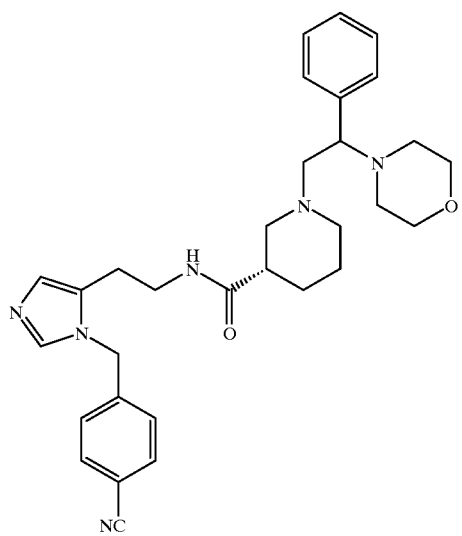
30
1-(Diphenylmethyl)-3(S)-[N-(1-(4-cyanobenzyl)-2-methyl-1H-imidazol-5-ylethyl)carbamoyl]piperidine
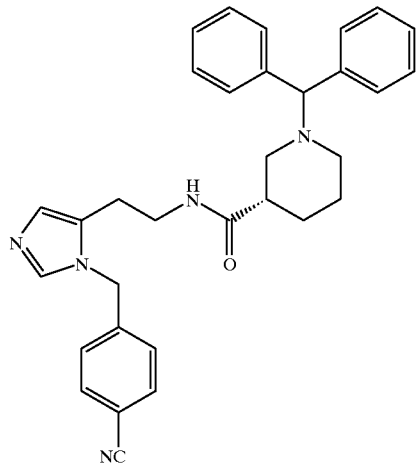
1-(3-Methylphenyl)-3(S)-[N-(1-(4-cyanobenzyl)-1H-imidazol-5-ylethyl)carbamoyl]piperidine
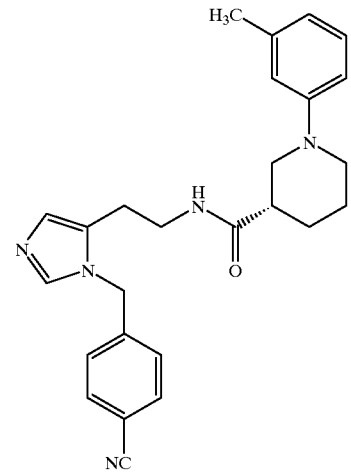

1-(2,2-Diphenylethyl)-3(S)-[N-(1-(4-cyanobenzyl)-1H-imidazol-5-ylethyl)-N-acetyl-aminomethyl]piperidine

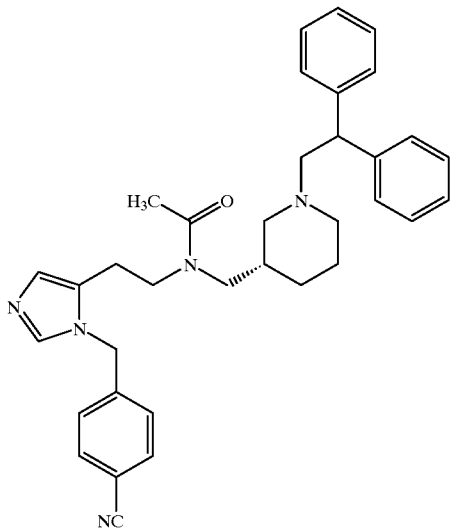

1-(Benzenesulfonyl)-3(S)-[N-(1-(4-cyanobenzyl)-1H-imidazol-5-ylethyl)carbamoyl]piperidine

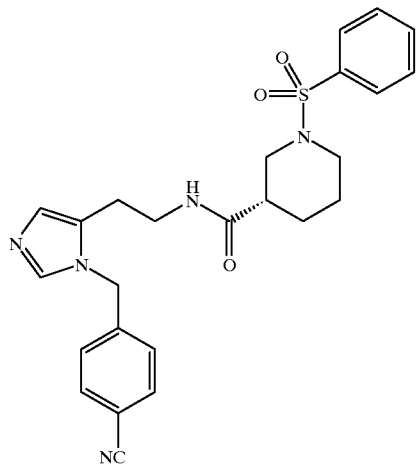

or an optical isomer or a pharmaceutically acceptable salt thereof.

The compounds of the present invention may have asymmetric centers and occur as racemates, racemic mixtures, and as individual diastereomers, with all possible isomers, including optical isomers, being included in the present invention. When any variable (e.g. aryl, heterocycle, $R^{1a}$, $R^4$ etc.) occurs more than one time in any constituent, its definition on each occurence is independent at every other occurence. Also, combinations of substituents/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein means fluoro, chloro, bromo and iodo.

As used herein, "aryl" is intended to mean any stable monocyclic, bicyclic or tricyclic carbon ring of up to 7 members in each ring, wherein at least one ring is aromatic. Examples of monocyclic and bicyclic aryl elements include phenyl, naphthyl, tetrahydronaphthyl, indanyl, biphenyl, phenanthryl, anthryl or acenaphthyl. Examples of tricyclic aryl elements include 10,11-dihydro-5H-dibenzo[a,d]cyclohepten-5-yl (which is also known as dibenzylsuberyl), 9-fluorenyl and 9,10-dihydroanthracen-9-yl. Preferably, "aryl" is a monocyclic or bicyclic carbon ring.

The term heterocycle or heterocyclic, as used herein, represents a stable 5- to 7-membered monocyclic or stable 8- to 11-membered bicyclic heterocyclic ring or stable 13- to 15-membered tricyclic heterocyclic ring, which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of monocyclic and bicyclic heterocyclic elements include, but are not limited to, azepinyl, benzimiidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl. Examples of tricyclic heterocyclic elements include, but are not limited to, 6,11-dihydro-5H-benzo[5,6]cyclohepta[1,2-b]pyridine, 9,10-dihydro-4H-3-thiabenzo[f]azulen-4-yl and 9-xanthenyl. The 6,11-dihydro-5H-benzo[5,6]cyclohepta[1,2-b]pyridine moiety has the following structure:

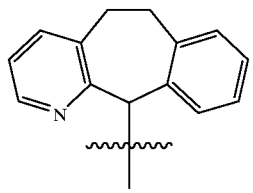

Preferably, "heterocyclic" is a monocyclic or bicyclic moiety.

As used herein, "heteroaryl" is intended to mean any stable monocyclic, bicyclic or tricyclic carbon ring of up to 7 members in each ring, wherein at least one ring is aromatic and wherein from one to four carbon atoms are replaced by heteroatoms selected from the group consisting of N, O, and S. Examples of monocyclic and bicyclic heteroaryl elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl. Examples of tricyclic heteroaryl elements include, but are not limited to, 6,11-dihydro-5H-benzo[5,6]cyclohepta[1,2-b]pyridine. Preferably, "heteroaryl" is a monocyclic or bicyclic moiety.

As used herein, the terms "substituted aryl", "substituted heterocycle" and "substituted cycloalkyl" are intended to include the cyclic group containing from 1 to 3 substitutents in addition to the point of attachment to the rest of the compound. Such substitutents are preferably selected from the group which includes but is not limited to F, Cl, Br, $CF_3$, $NH_2$, $N(C_1-C_6$ alkyl$)_2$, $NO_2$, CN, $(C_1-C_6$ alkyl$)O-$, $-OH$, $(C_1-C_6$ alkyl$)S(O)_m-$, $(C_1-C_6$ alkyl$)C(O)NH-$, $H_2N-C(NH)-$, $(C_1-C_6$ alkyl$)C(O)-$, $(C_1-C_6$ alkyl$)OC(O)-$, $N_3$, $(C_1-C_6$ alkyl$)OC(O)NH-$ and $C_1-C_{20}$ alkyl.

When $R^6$ and $R^7$ or $R^7$ and $R^{7a}$ are combined to form a ring, cyclic amine moieties are formed. Examples of such cyclic moieties include, but are not limited to:

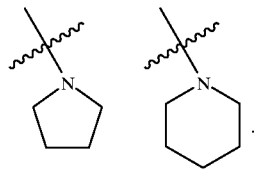

In addition, such cyclic moieties may optionally include another heteroatom(s). Examples of such heteroatom-containing, cyclic amine moieties include, but are not limited to:

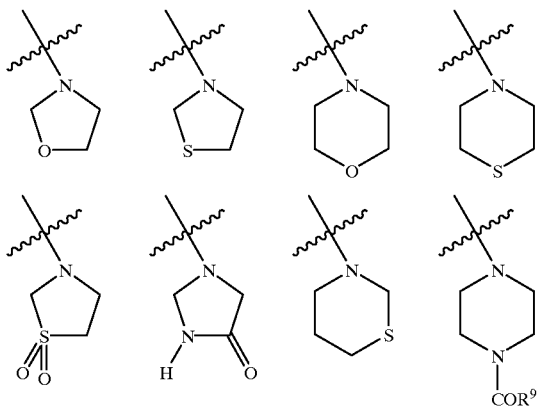

Lines drawn into the ring systems from substituents (such as from $R^2$, $R^3$, $R^4$ etc.) indicate that the indicated bond may be attached to any of the substitutable ring carbon atoms.

Preferably, $R^{1a}$ and $R^{1b}$ are independently selected from: hydrogen, $-N(R^8)_2$, $R^8C(O)NR^8-$ or $C_1-C_6$ alkyl which is unsubstituted or substituted by $-N(R^8)_2$, $R^8O-$ or $R^8C(O)NR^8-$.

Preferably, $R^2$ is selected from:
a) $C_{1-8}$ alkyl, unsubstituted or substituted with one or more of:
1) aryl or heterocycle, unsubstituted or substituted with:
  i) $C_{1-4}$ alkyl,
  ii) $(CH_2)_pOR^6$,
  iii) $(CH_2)_pNR^6R^7$,
  iv) halogen,
  v) $C_{1-4}$ perfluoroalkyl,
2) $OR^6$,
3) $SR^6$, $SO_2R^6$, or 4) 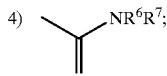

b) 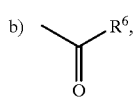

c) aryl, unsubstituted or substituted with one or more of:
1) $C_{1-8}$ alkyl,
2) $C_{1-8}$ perfluoroalkyl,
3) $OR^6$,
4) $SR^6$, $SO_2R^6$, or 5) 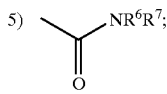

d) $-SO_2R^6$.

Preferably, $R^2$ comprises at least one unsubstituted or substituted phenyl.

Preferably, $R^4$ is selected from: hydrogen, perfluoroalkyl, F, Cl, Br, $R^8O-$, $R^9S(O)_m-$, CN, $NO_2$, $R^8{}_2N-C(NR^8)-$, $R^8C(O)-$, $N_3$, $-N(R^8)_2$, $R^9OC(O)NR^8-$ and $C_1-C_6$ alkyl.

Preferably, $R^5$ is hydrogen.

Preferably, $R^{7b}$ is $C_1-C_6$ alkyl substituted with hydrogen or an unsubstituted or substituted aryl group.

Preferably, $R^8$ is selected from H, $C_1-C_6$ alkyl and benzyl.

Preferably, $A^1$ and $A^2$ are independently selected from: a bond, $-C(O)NR^8-$, $-NR^8C(O)-$, O, $-N(R^8)-$, $-S(O)_2N(R^8)-$ and $-N(R^8)S(O)_2-$.

Preferably, V is selected from hydrogen, heterocycle and aryl.

Preferably, W is imidazolyl.

Preferably, X is a bond, $-C(=O)NR^{10}-$, $-NR^{10}C(=O)-$ or $-NR^{10}-$.

Preferably, n, p and r are independently 0, 1, or 2.

Preferably t is 1.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

It is intended that the definition of any substituent or variable (e.g., $R^{1a}$, Z, n, etc.) at a particular location in a molecule be independent of its definitions elsewhere in that molecule. Thus, $-N(R^8)_2$ represents $-NH_2$, $-NHCH_3$, $-NHC_2H_5$, etc. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Abbreviations used in the description of the chemistry and in the Examples that follow are:

| | |
|---|---|
| Ac$_2$O | Acetic anhydride; |
| Boc | t-Butoxycarbonyl; |
| CBz | Carbobenzyloxy; |
| DBU | 1,8-diazabicyclo[5.4.0]undec-7-ene; |
| DMAP | 4-Dimethylaminopyridine; |
| DME | 1,2-Dimethoxyethane; |
| DMF | Dimethylformamide; |
| EDC | 1-(3-dimethylaminopropyl)-3-ethyl-carbodiimide-hydrochloride; |
| Et$_3$N | Triethylamine; |
| EtOAc | Ethyl acetate; |
| FAB | Fast atom bombardment; |
| HOBT | 1-Hydroxybenzotriazole hydrate; |
| HOOBT | 3-Hydroxy-1,2,2-benzotriazin-4(3H)-one; |
| HPLC | High-performance liquid chromatography; |
| MCPBA | m-Chloroperoxybenzoic acid; |
| MsCl | Methanesulfonyl chloride; |
| NaHMDS | Sodium bis(trimethylsilyl)amide; |
| Py | Pyridine; |
| TFA | Trifluoroacetic acid; |
| THF | Tetrahydrofuran. |

The compounds of this invention are prepared by employing reactions as shown in the Schemes 1–21, in addition to other standard manipulations such as ester hydrolysis, cleavage of protecting groups, etc., as may be known in the literature or exemplified in the experimental procedures. While stereochemistry is shown in the Schemes, a person of ordinary skill in the art would understand that the illustrated compounds represent racemic mixtures which may be separated at a subsequent purification step or may be utilized as the racemic mixture.

These reactions may be employed in a linear sequence to provide the compounds of the invention or they may be used to synthesize fragments which are subsequently joined by the reductive alkylation or acylation reactions described in the Schemes.

Synopsis of Schemes 1–8:

The requisite intermediates are in some cases commercially available, or can be prepared according to literature procedures, for the most part. In Schemes 1–3, for example, the syntheses of 1,3,5-trisubstituted piperidines are outlined. The reactions described therein may be similarly applied to suitably protected commercially available nipecotic acid or nipecotamide to provide compounds of the instant invention wherein R$^3$ is hydrogen.

As shown in Scheme 1, the pyridinedicarboxylic acid diester may be catalytically hydrogenated and then N-protected to provide a mixture of piperidine diesters 1. The protected piperidine can then be partially hydrolyzed to provide a racemic mixture of 3,5-cis- and trans-isomers, that can be separated by chromatography. The remainder of Scheme 1 and Schemes 2 and 3 illustrate manipulation of the racemic mixture of the cis-isomers. It is well understood by one of ordinary skill in the art that such chemical manipulations can also be applied to the racemic mixture of the trans-isomers to obtain other compounds of the instant invention. Furthermore, such manipulations can also be applied to enantiomerically pure isomers (i.e., the (+)-cis isomer or the (−)-cis isomer). The trans-isomer may also be epimerized to the cis-isomer by treatment with a base, such as sodium carbonate. Racemic final compounds may be separated on a chiral preparative HPLC column to give their respective diastereomers.

The monocarboxylic acid 2 can be treated with an appropriately substituted amine in the presence of a suitable coupling reagent, such as EDC/HOBT, and the like, to provide the 5-carboxynipecotamide 3. The suitably substituted 5-carboxynipecotamide is then deprotected and the piperidine nitrogen can then be reductively alkylated to provide intermediate 4. The remaining ester moiety is saponified and then similarly functionalized with another suitably substituted amine to provide the bisamidopiperdine 5.

An alternative synthetic route to compound 5, starting with the carboxynipecotamide 3, is illustrated in Scheme 2.

As shown in Scheme 3, the monocarboxylic acid 2 can undergo a Curtius rearrangment to provide the piperidine 6 after catalytic reduction. Subsequent amide formation provides intermediate 7, which is then subjected to the reactions illustrated in Scheme 1 to provide compound 8 of the instant invention.

The instant invention also includes 1,4-dihydropyridine and 1,2,3,4-tetrahydropyridine analogs of the piperidine compounds whose syntheses are described above. Scheme 4 illustrates the synthetic route to the intermediates 11 and 13 which correspond to the saturated ring intermedate 2 illustrated in Scheme 1. Thus, the appropriately substituted pyridine may be N-alkylated to provide the quaternary intermediate 9. Subsequent reduction of this intermediate provides the 1,4-dihydropyridine 10, which can be selectively hydrolized to the key intermediate 11. Alternatively, the 1,4-dihydropyridine 10 can be further reduced to provide the enantiomeric mixture of tetrahydropyridines 12, which can be hydrolized and resolved by chromatography to provide the key intermediate 13 (and the enantiomer which is not illustrated). Intermediates 11 and 13 can then undergo synthetic modifications as described hereinabove in Schemes 1–3.

Schemes 5–7 illustrate the syntheses of 1,3-disubstituted piperidines of the instant invention wherein the "X" moiety is other than an amido moiety. The reactions illustrated therein may be modified by using appropriate protecting groups and reagents well known to one skilled in the art to provide 1,3,5-trisubstituted piperidines of the instant invention.

Scheme 5 illustrates the syntheses of compounds of the instant invention wherein "X" is —S— or —SO$_2$—. A racemic nipecotate 14 can be resolved by the selective crystallization of chiral tartrate salts and is then reductively alkylated to provide the ester 15. Intermediate 15 is reduced to the alcohol 16, activated and treated with a suitable thioacetate to provide the thioester 17. The thiol is then generated and may be alkylated and optionally oxidized to provide compounds 18 and 19 of the instant invention.

The intermediate 16 may be selectively oxidized back to an aldehyde, which can then be utilized to reductively alkylate a suitably substituted amine to provide the instant compound 20. The secondary amine of 20 can be further functionalized as illustrated.

The activated alcohol can also be reacted with a suitably substituted imidazolyl to provide compounds of the instant invention wherein "X" is a bond, as shown in Scheme 7.

Scheme 8 illustrates the syntheses of compounds of the instant invention wherein R$^2$ is an aryl moiety.

37
SCHEME 1
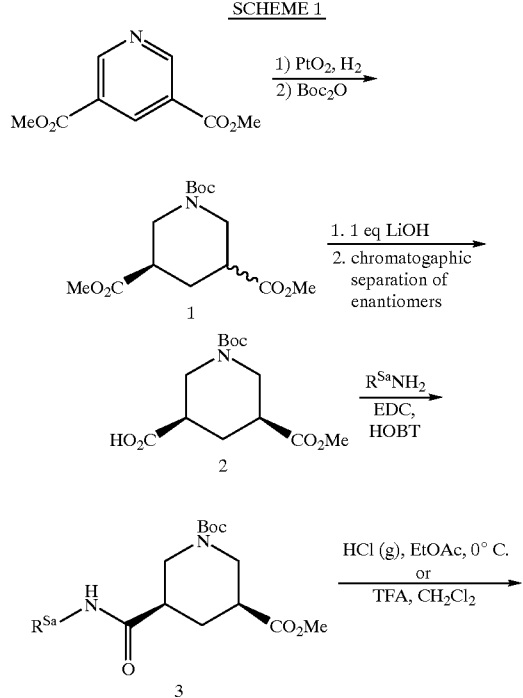
38
SCHEME 2
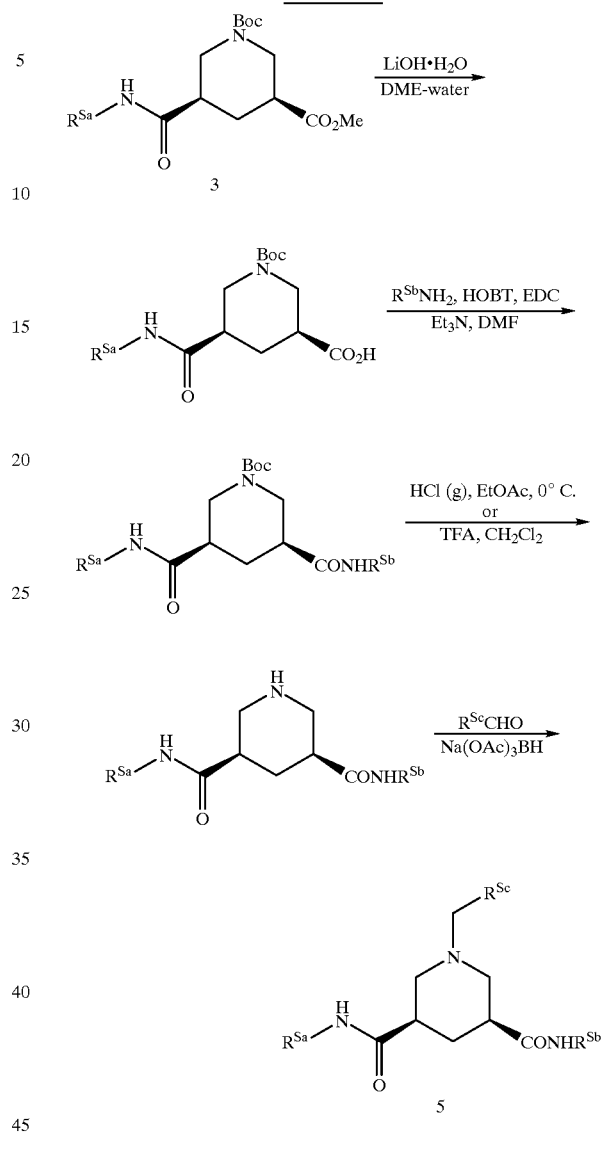
SCHEME 3
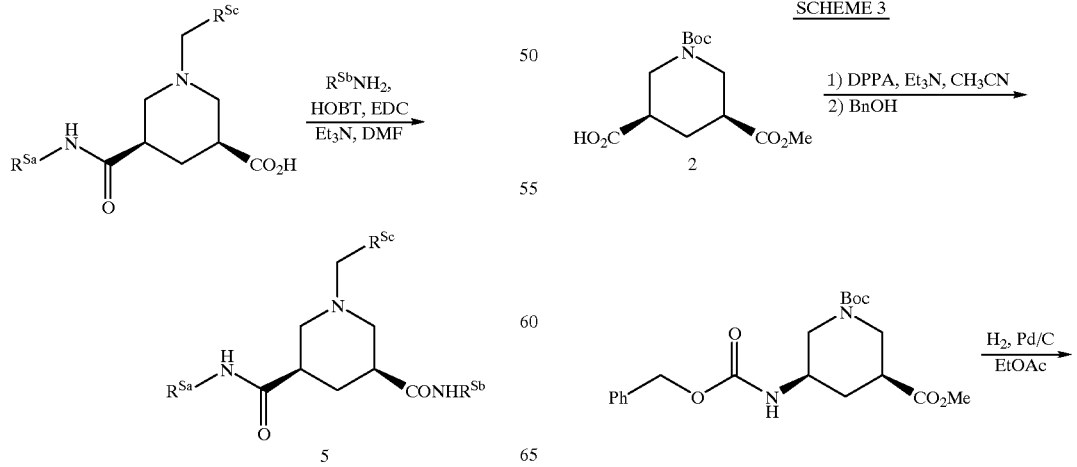

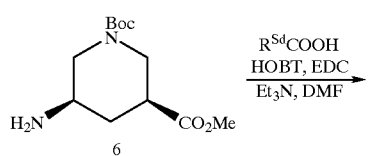
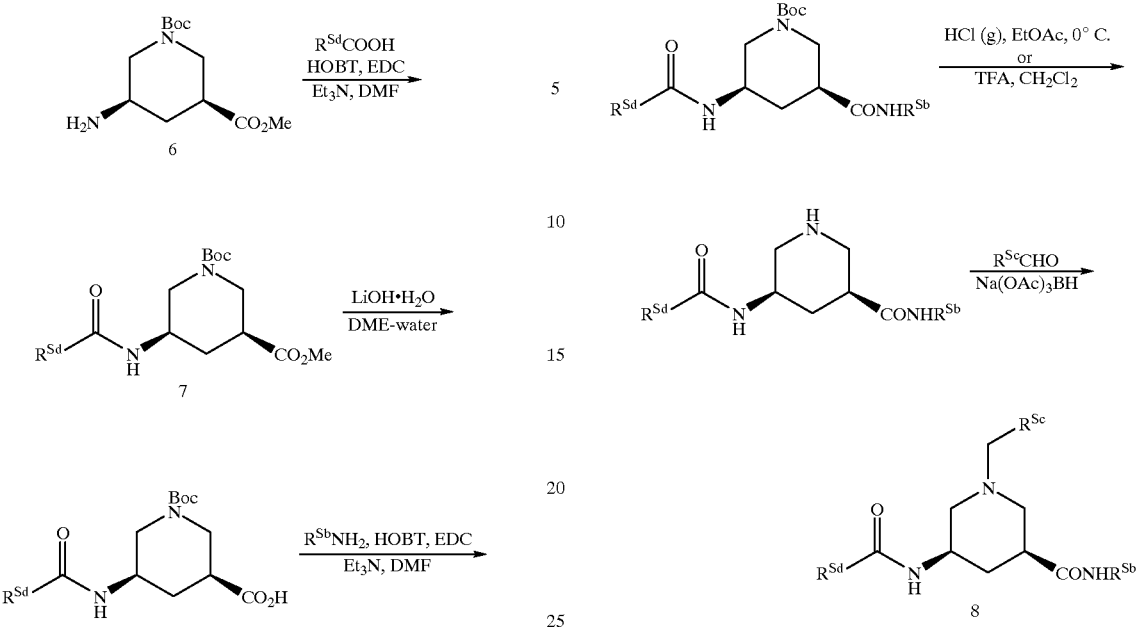
SCHEME 4
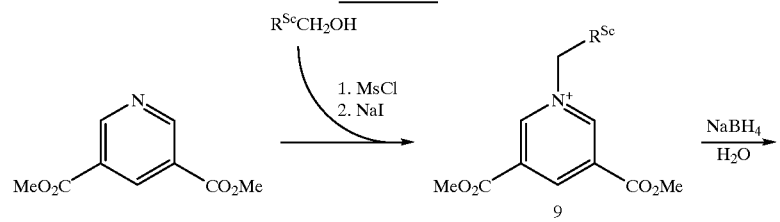
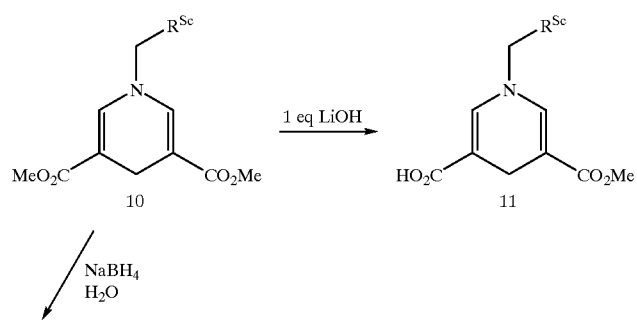
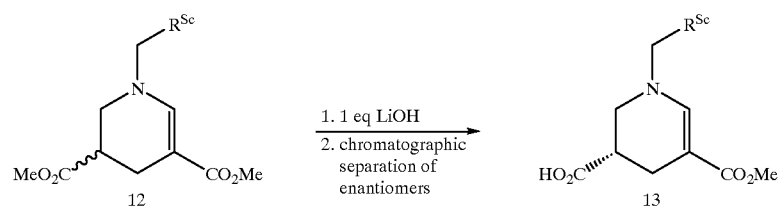

SCHEME 5
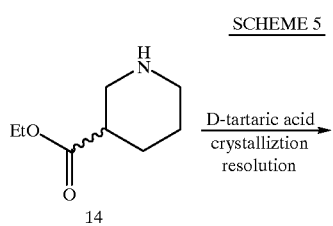
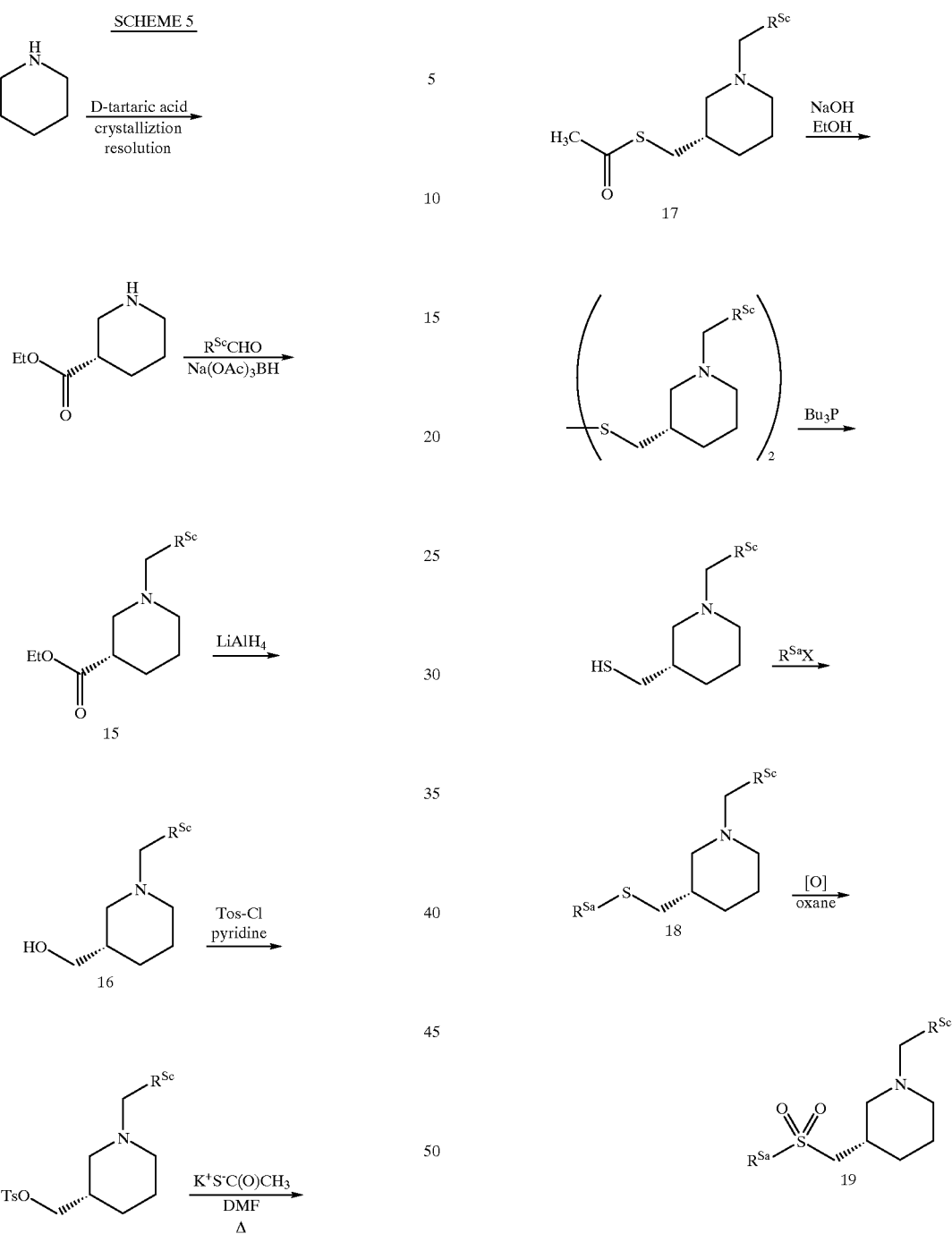
SCHEME 6
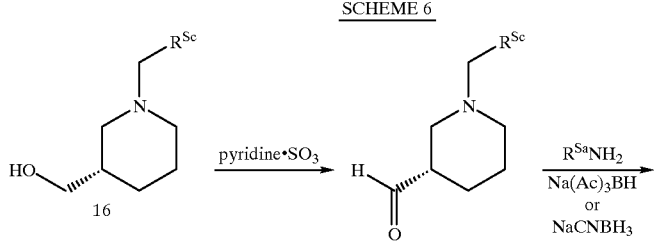

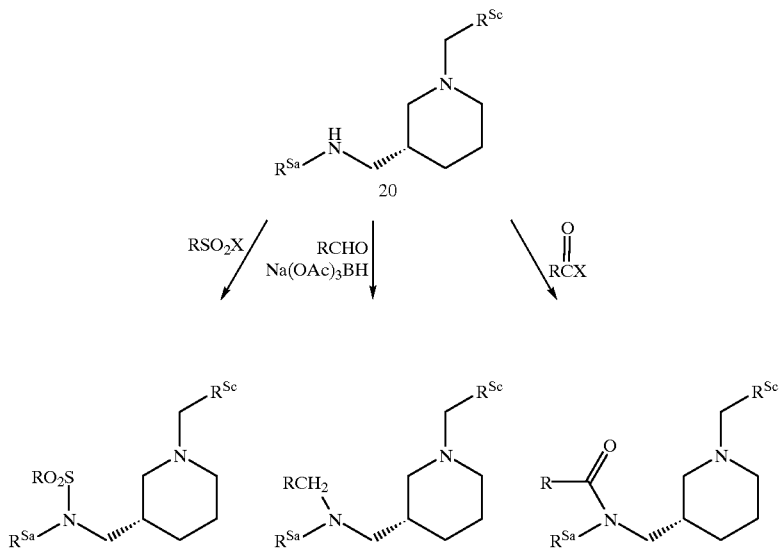

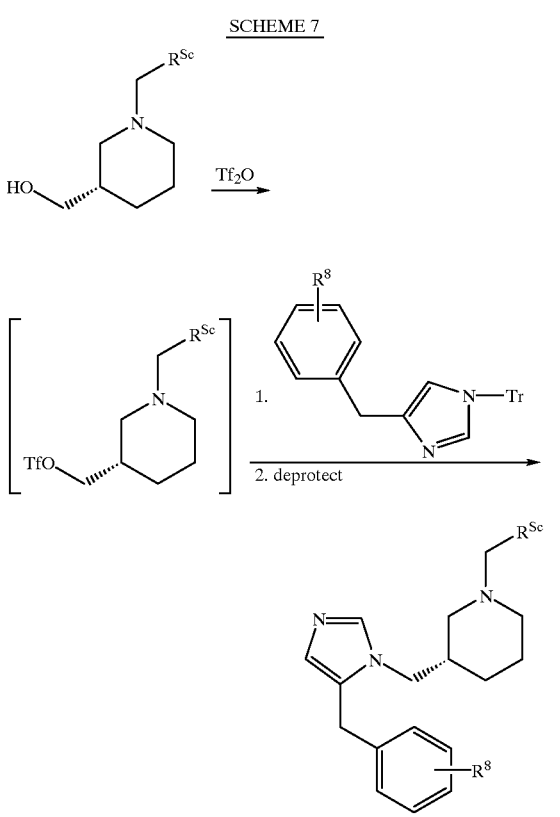

SCHEME 7

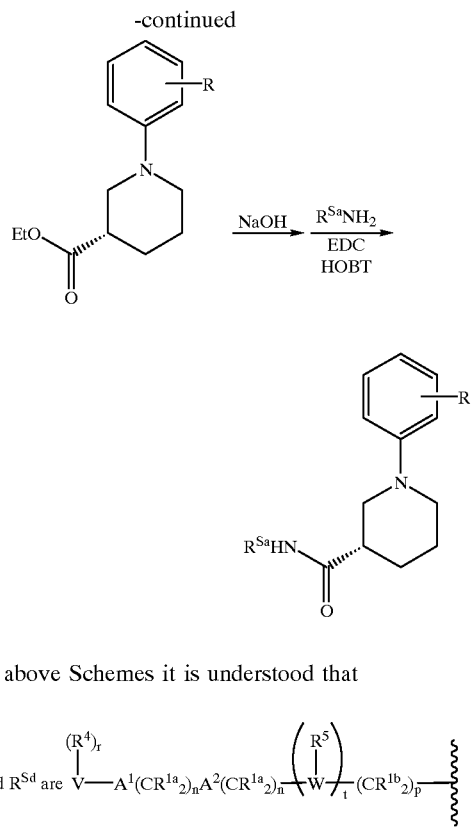

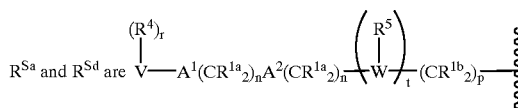

In the above Schemes it is understood that $$R^{Sa} \text{ and } R^{Sd} \text{ are } V—A^1(CR^{1a}{}_2)_n A^2(CR^{1a}{}_2)_{\bar{n}} \left(W\right)_t (CR^{1b}{}_2)_p \sim$$

or a protected precursor thereof;
$R^{Sc}CH_2$— is $R^2$ or a protected precursor thereof; and
$R^{Sb}$— is $R^6$ or a protected precusor thereof; and
R— is a "substituent" or a protected precursor thereof.

It is understood that a variety of amines and acids, either commercially available or readily synthesized by reactions well known in the art, which contain the side-chain moieties $R^{Sa}$ and $R^{Sd}(C=O)$ may be utilized in the reactions described hereinabove. Schemes 9–21 illustrate specific reactions wherein such intermediates containing the side-chain moieties $R^{Sa}$ and $R^{Sd}(C=O)$ may be prepared. It is

SCHEME 8

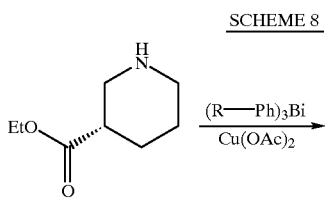

understood that while Schemes 9–21 illustrate preparation of both protected and unprotected intermediates, a person of ordinary skill would appreciate that subsequent reactions which utilize those intermediates, such as those described in Schemes 1–8, may require protection and eventual deprotection of certain intermediate moieties.

The selectively protected intermediate 20 utilized in the synthesis illustrated in Scheme 9 can be reductively alkylated with a variety of aldehydes, such as 21. The aldehydes can be prepared by standard procedures, such as that described by O. P. Goel, U. Krolls, M. Stier and S. Kesten in *Organic Syntheses,* 1988, 67, 69–75. The reductive alkylation can be accomplished at pH 5–7 with a variety of reducing agents, such as sodium triacetoxyborohydride or sodium cyanoborohydride in a solvent such as dichloroethane, methanol or dimethylformamide. The ester product 22 can be deprotected with trifluoroacetic acid in methylene chloride to give the substituted diamine 23. That diamine may be isolated in the salt form, for example, as a trifluoroacetate, hydrochloride or acetate salt, among others. The product diamine 23 can be further selectively protected and reductively alkylated with a second aldehyde to obtain an analogous tertiary amine. Alternatively, the diamine 23 can be cyclized to obtain intermediates such as the dihydroimidazole 24 by procedures known in the literature. The ester 24 can then be utilized in a reaction such as illustrated in Scheme 3 hereinabove or can be converted to the amine 26, via the azido intermediate 25. That amine can then be utilized in reactions such as illustrated in Scheme 1.

Scheme 10 illustrates preparation of aralkyl imidazolyl intermediates 31 that can be utilized in reactions such as illustrated in Scheme 3. Thus imidazole acetic acid 27 can be converted to the protected acetate 29 by standard procedures, and 29 can be first reacted with an alkyl halide, then treated with refluxing methanol to provide the regiospecifically alkylated imidazole acetic acid ester 30. Hydrolysis provides the acetic acid 31.

Alternatively, intermediate 31 can be converted into the homologous amine 34 via the azido intermediate 33, as shown in Scheme 11. This amine can then be utilized in reactions such as illustrated in Scheme 1.

Preparation of amine intermediates having mixed heteroatom substitution is illustrated in Schemes 12 and 13. Thus the protected serine 35 can be reduced to the alcohol 36, which can then undergo a Mitsunobu reaction to provide the phthalimidyl intermediate 37. Deprotection and selective reprotection give the alcohol 39, which can be oxidized to the aldehyde 40. The aldehyde 40 can be subsequently alkylated and finally deprotected to provide the amine intermediate 41.

The Boc protected phthalimidyl alcohol 39 can also be utilized to synthesize 2-aziridinylmethylamines such as 42 (Scheme 13). Treating 39 with 1,1'-sulfonyldiimidazole and sodium hydride in a solvent such as dimethylformamide led to the formation of aziridine 42. The aziridine may then be reacted in the presence of a nucleophile, such as a thiol, in the presence of base to yield, after deprotection, the ring-opened intermediate amine 43.

In addition, amines such as 48 derived from amino acids such as O-alkylated tyrosines can be prepared according to standard procedures as shown in Scheme 14. Illustrated is a procedure where the amine moiety is derived from the azide of an intermediate such as 47.

Schemes 15–18 illustrate syntheses of suitably substituted alkanols useful in the syntheses of the instant compounds wherein the variable W is present as a pyridyl moiety. The hydroxyl moiety of such intermediates may be converted into the corresponding amine, as illustrated in Scheme 15 or may be converted to a suitable leaving group, as illustrated in Scheme 17. Similar synthetic strategies for preparing alkanols that incorporate other heterocyclic moieties for variable W are also well known in the art.

Compounds of the instant invention wherein the $A^1(CR^{1a}_2)_nA^2(CR^{1a}_2)_n$ linker is a substituted methylene may be synthesized by the methods shown in Scheme 19. Thus, the N-protected imidazolyl iodide 50 is reacted, under Grignard conditions with a suitably protected benzaldehyde to provide the alcohol 51. Acylation, followed by the alkylation procedure illustrated in the Schemes above (in particular, Scheme 7) provides the instant compound 52. If other $R^1$ substituents are desired, the acetyl moiety can be manipulated as illustrated in the Scheme.

Scheme 20 illustrates synthesis of an instant compound wherein a non-hydrogen $R^{5b}$ is incorporated in the instant compound. Thus, a readily available 4-substituted imidazole 53 may be selectively iodinated to provide the 5-iodoimidazole 54. That imidazole may then be protected and coupled to a suitably substituted benzyl moiety to provide intermediate 55. Intermediate 55 can then undergo the alkylation reactions that were described hereinabove.

Compounds of the instant invention wherein the $A^1(CR^1_2)_nA^2(CR^1_2)_n$ linker is oxygen may be synthesized by methods known in the art, for example as shown in Scheme 21. The suitably substituted phenol 56 may be reacted with methyl N-(cyano)methanimidate to provide the 4-phenoxyimidazole 57. After selective protection of one of the imidazolyl nitrogens, the intermediate 58 can undergo alkylation reactions as described for the benzylimidazoles hereinabove.

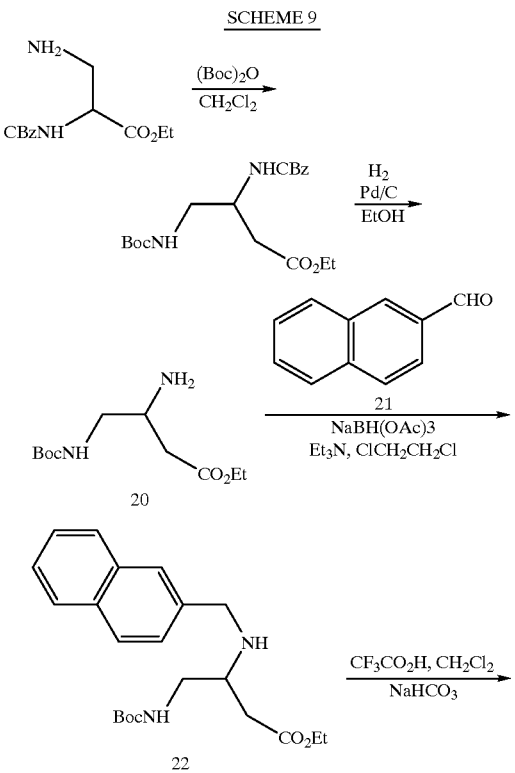

SCHEME 9

6,127,366
47
-continued
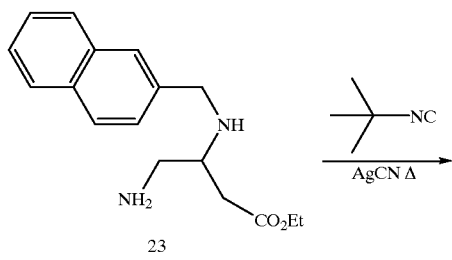
23
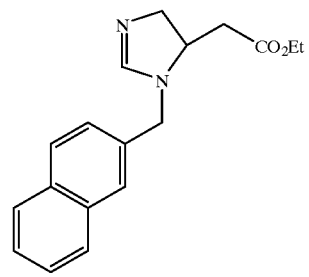
24
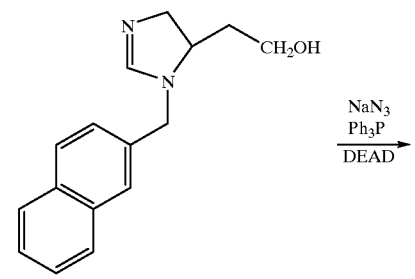
25
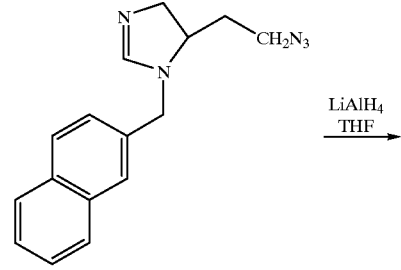
26
SCHEME 10
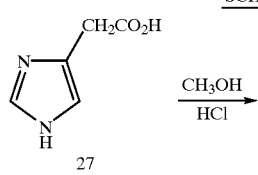
27
48
-continued
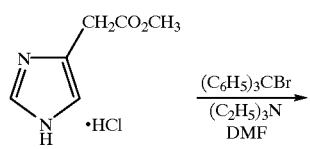
28
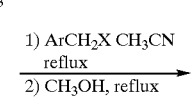
29
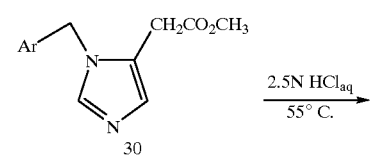
30
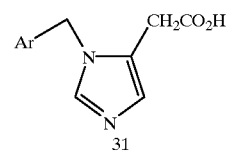
31
SCHEME 11
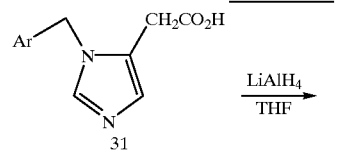
31
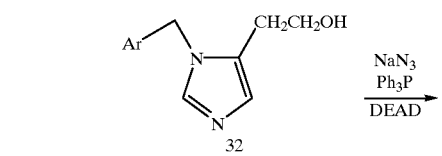
32
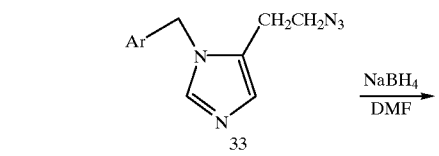
33
34
SCHEME 12
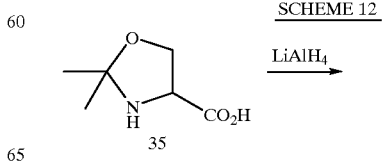
35

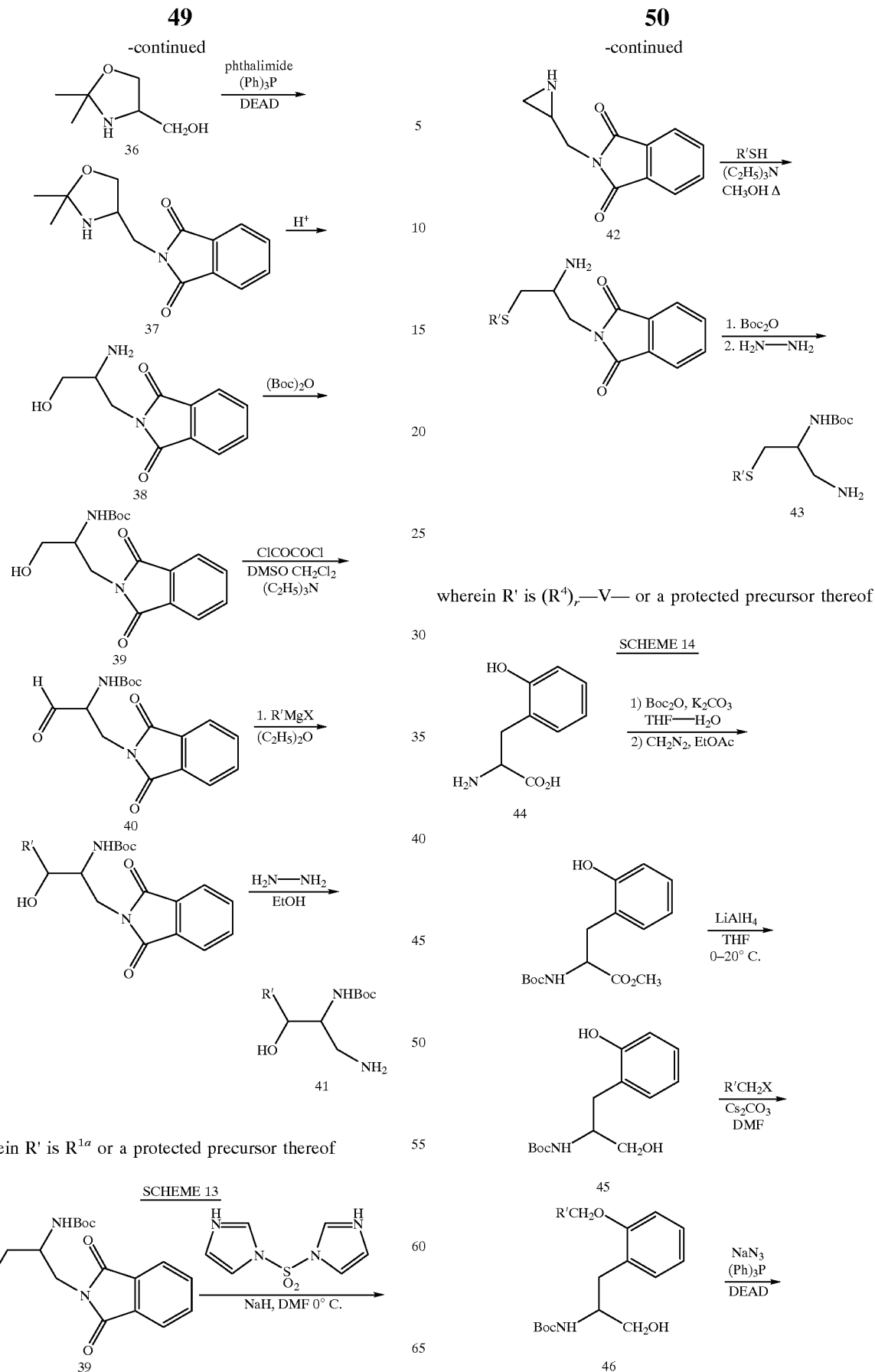

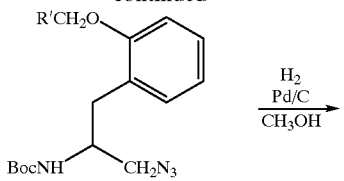
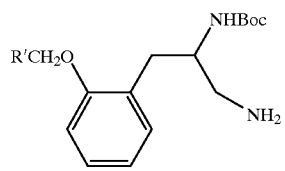
wherein R'CH$_2$— is R$^8$ or a protected precursor thereof
SCHEME 15
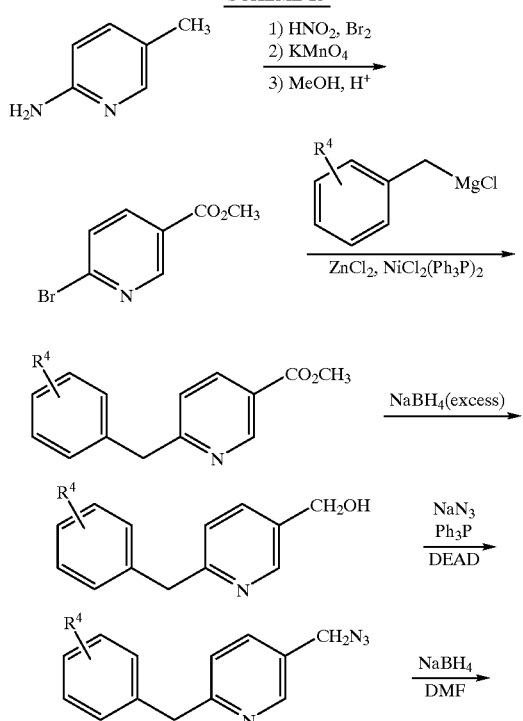
SCHEME 16
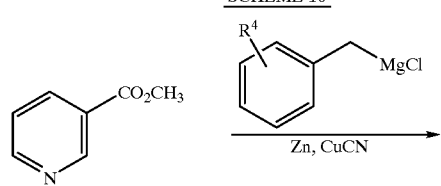
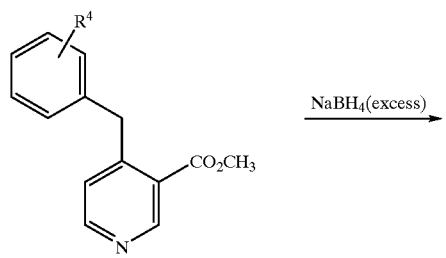
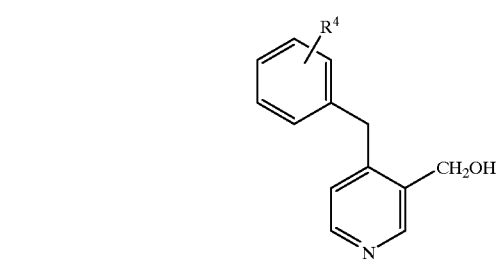
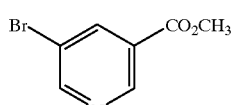
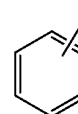
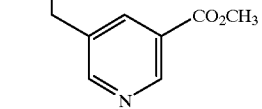
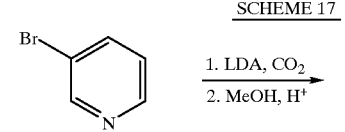
SCHEME 17
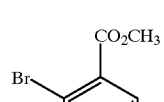

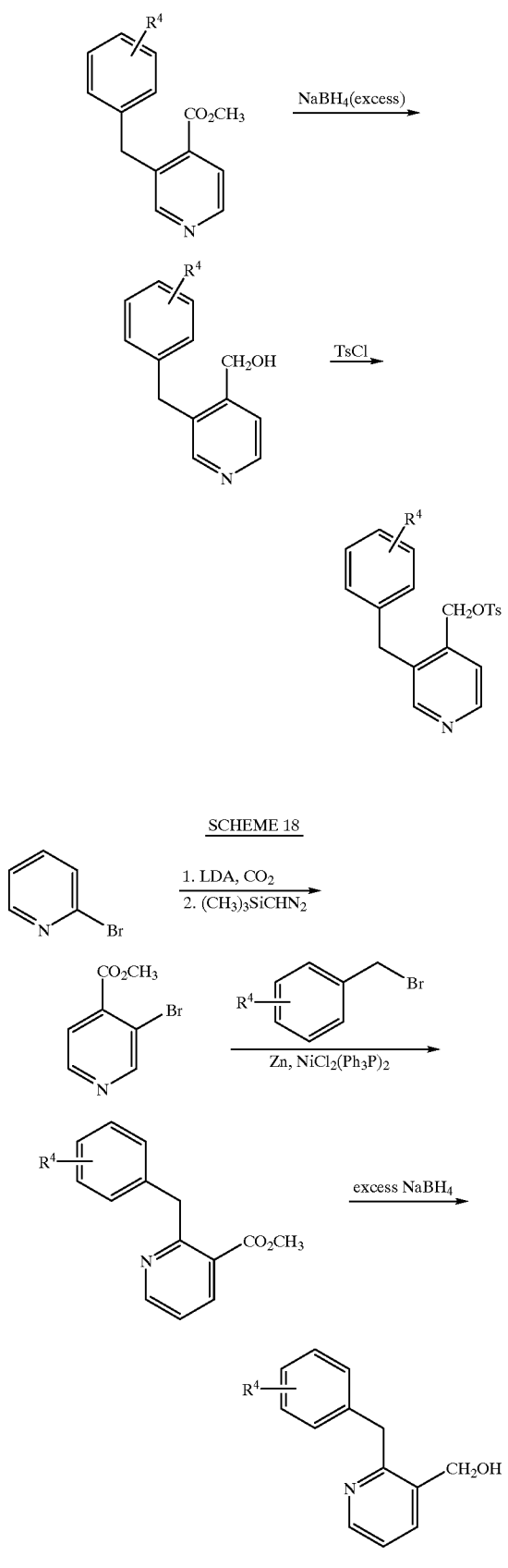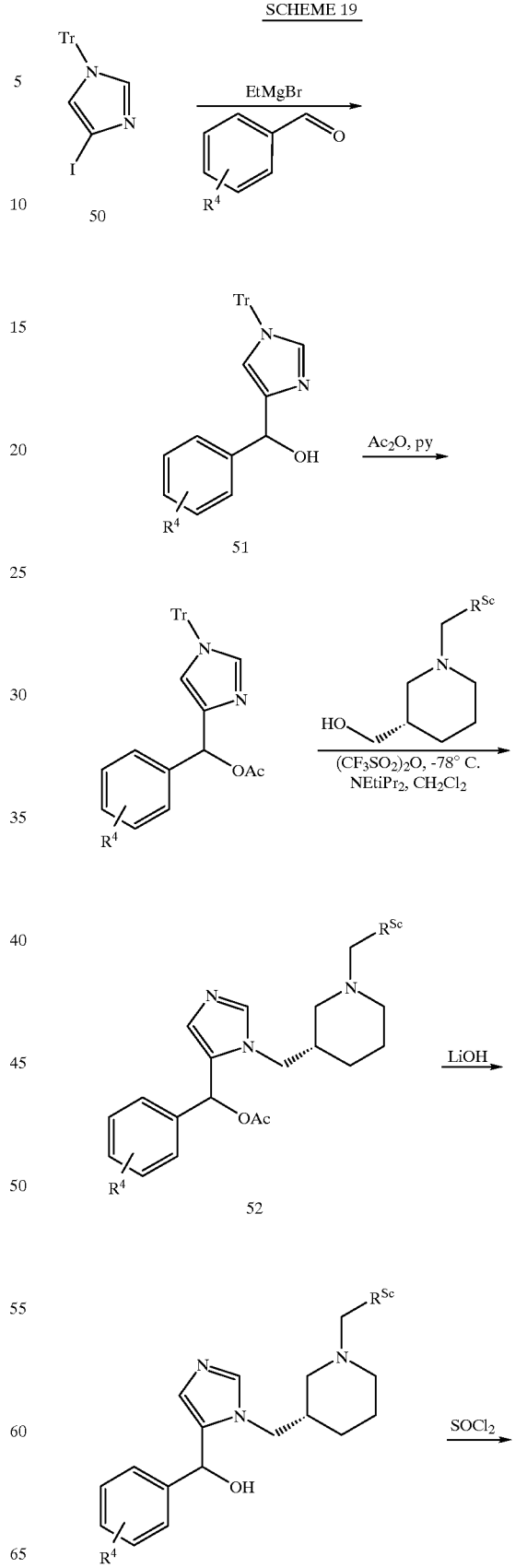

-continued
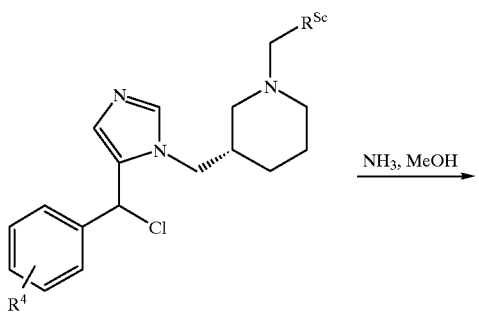
NH₃, MeOH →
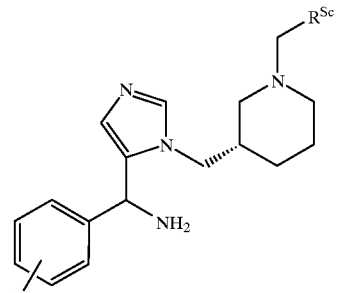
+
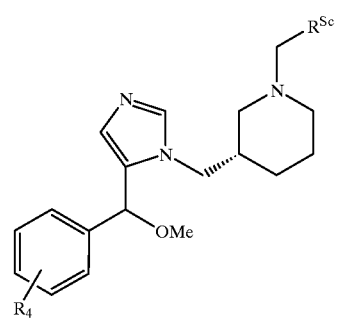
-continued
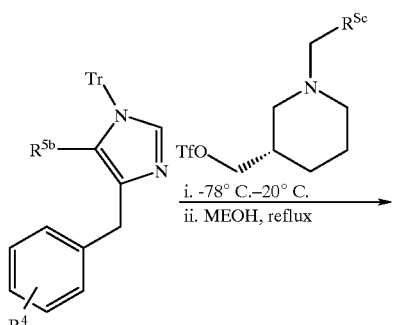
i. -78° C.–20° C.
ii. MEOH, reflux →
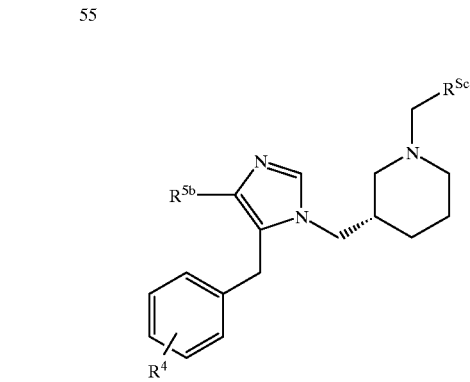
SCHEME 21
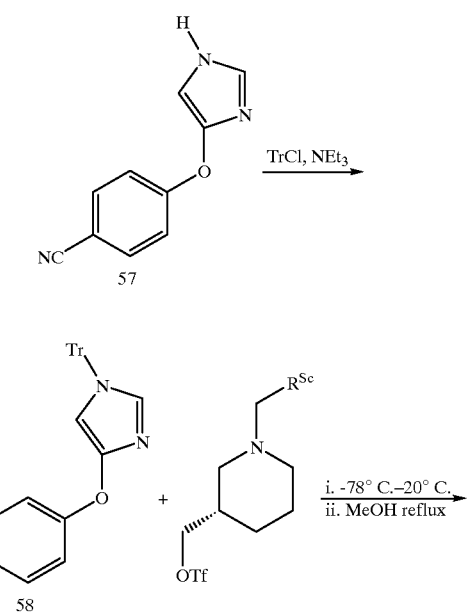
SCHEME 20
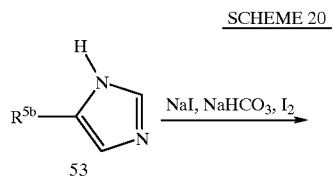
NaI, NaHCO₃, I₂ →
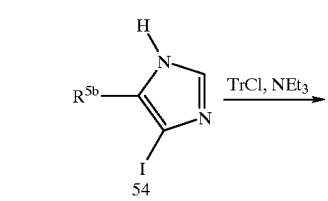
TrCl, NEt₃ →
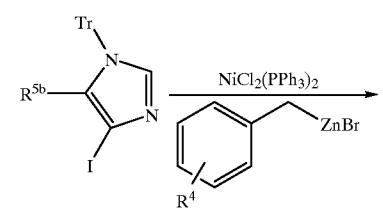

-continued

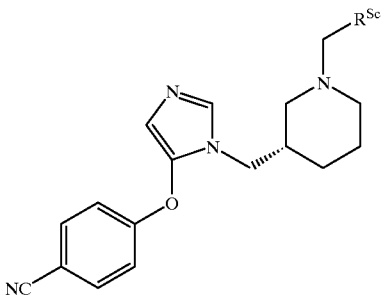

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, scr, abl, lck, fyn) or by other mechanisms.

The compounds of the instant invention inhibit farnesyl-protein transferase and the farnesylation of the oncogene protein Ras. The instant compounds may also inhibit tumor angiogenesis, thereby affecting the growth of tumors (J. Rak et al. *Cancer Research*, 55:4575–4580 (1995)). Such anti-angiogenesis properties of the instant compounds may also be useful in the treatment of certain forms of blindness related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful in the treatment of certain viral infections, in particular in the treatment of hepatitis delta and related viruses (J. S. Glenn et al. *Science*, 256:1331–1333 (1992).

The compounds of the instant invention are also useful in the prevention of restenosis after percutaneous transluminal coronary angioplasty by inhibiting neointimal formation (C. Indolfi et al. *Nature medicine*, 1:541–545(1995).

The instant compounds may also be useful in the treatment and prevention of polycystic kidney disease (D. L. Schaffner et al. *American Journal of Pathology*, 142:1051–1060 (1993) and B. Cowley, Jr. et al. *FASEB Journal*, 2:A3160 (1988)).

The instant compounds may also be useful for the treatment of fungal infections.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

As used herein, the term "composition" is intended to encompass a product comprising the specified ingredients in the specific amounts, as well as any product which results, directly or indirectly, from combination of the specific ingredients in the specified amounts.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof. Purification by HPLC or column chromatography was utilized for each of the Examples 1–24 as set forth below.

Example 1

Preparation of 1-(t-Butoxycarbonyl)-cis-3-methoxycarbonyl-5-[N-(1-(4-cyanobenzyl)-1H-imidazol-5-ylethyl)carbamoyl]piperidine Step A: Preparation of Pyridine-3,5-dicarboxylic acid methyl ester hydrochloride Pyridine-3,5-dicarboxylic acid (5.00 g, 29.9 mmol) was stirred in $CH_3OH$ (100 mL), cooled in an ice bath, and treated dropwise with thionyl chloride (17.45 mL, 239.2 mmol). After 0.5 hr, the reaction mixture was refluxed for 48 hrs. Concentration to dryness gave the title compound as an off-white solid.

Step B: Preparation of Piperidine-cis, trans-3,5-dicarboxylic acid methyl ester hydrochloride Pyridine-3,5-dicarboxylic acid methyl ester hydrochloride (7.07 g, 30.5 mmol) was dissolved in acetic acid(75 mL), treated with platinum(IV) oxide (100 mg, 0.44 mmol) and shaken on a Parr apparatus at 50 psi overnight. The reaction mixture was filtered through celite and concentrated to dryness to give the title compound.

Step C: Preparation of 1-(t-Butoxycarbonyl)piperidine-cis and trans-3,5-dicarboxylic acid methyl ester Piperidine-3,5-dicarboxylic acid methyl ester hydrochloride (7.11 g, 29.9 mmol) was dissolved in THF (60 mL) and $H_2O$ (60 mL). Sodium bicarbonate (13.81 g, 0.164 mol) was added followed by di-tert-butyl dicarbonate (9.79 g, 44.9 mmol). The mixture was stirred at ambient temperature for 5 hrs. The THF was removed under reduced pressure, and the solution was extracted with $CH_2Cl_2$ (3×100 mL). The combined $CH_2Cl_2$ layers were washed with brine and dried ($MgSO_4$). Filtration and concentration to dryness gave, after chromatography (silica gel, 10% ethyl acetate/hexane), racemic 1-(t-Butoxycarbonyl)piperidine-cis-3,5-dicarboxylic acid methyl ester and racemic 1-(t-Butoxycarbonyl) piperidine-trans-3,5-dicarboxylic acid methyl ester.

Step D: Preparation of 1-(t-Butoxycarbonyl)-cis-3-methoxycarbonyl-piperidine-5-carboxylic acid 1-(t-Butoxycarbonyl)piperidine-cis-3,5-dicarboxylic acid methyl ester(0.761 g, 2.52 mmol) was dissolved in DME (6 mL) and $H_2O$ (6 mL) followed by addition of $LiOH \cdot H_2O$ (0.106 g, 2.52 mmol). The mixture was stirred at ambient temperature overnight. The DME was removed under reduced pressure, taken up in EtOAc and water, acidified to pH 3, and extracted with EtOAc (10×). The EtOAc layers were combined, dried ($MgSO_4$), filtered, and concentrated to dryness to give the title compound after chromatography (silica gel, 1–3% $MeOH/CH_2Cl_2$).

Step E: Preparation of 3-(4-cyanobenzyl) histamine

Nγ-Pivaloyloxymethyl-$N^\alpha$-phthaloylhistamine (4.55 g, 12.8 mmol) was prepared as previously described (J. C. Emmett, F. H. Holloway, and J. L. Turner, *J. Chem. Soc., Perkin Trans.* 1, 1341, (1979)). α-Bromo-p-tolunitrile (3.77 g, 19.2 mmol) was dissolved in acetonitrile (70 mL). The solution was heated at 55° C. for 4 h, cooled to room temperature, and filtered to remove the white solid. The acetonitrile (30 mL) was concentrated to ½ its volume under reduced pressure and the solution was heated at 55° C. overnight. The solution was cooled and filtered to give a white solid. The volume of the filtrate was reduced to 10 mL, the solution was heated at 55° C. for 1 hr, then cooled to room temperature, diluted with EtOAc (25 mL) and filtered to obtain additional white solid. The solids were combined, dried, and used without further purification.

1-Pivaloyloxymethyl-3-(4-cyanobenzyl)-4-(2-phthalimidoethyl)imidazolium bromide (6.13 g, 11.1 mmol) in methanol (100 mL) was saturated with ammonia gas while the temperature was maintained below 30° C. The solution was stirred for 1 hr, concentrated to dryness, and extracted with $CH_2Cl_2$ (3×200 mL), dried ($MgSO_4$), concentrated, and chromatographed (silica gel, 10:90:1 $MeOH/CH_2Cl_2/NH_4OH$) to give 4-cyanobenzyl-$N^\alpha$-phthaloylhistamine.

3-(4-Cyanobenzyl)-$N^\alpha$-phthaloylhistamine (1.64 g, 4.61 mmol), and hydrazine (1.46 mL, 46.1 mmol) were dissolved in absolute EtOH (70 mL). The solution was concentrated after 1 hr and filtered to remove a white precipitate which was washed several times with EtOH. The filtrate was concentrated and the residue was chromatographed (silica gel, 10:90:1 $MeOH/CH_2Cl_2/NH_4OH$) to give the title compound.

Step F: Preparation of 1-(t-Butoxycarbonyl)-cis-3-methoxycarbonyl-5-[N-(1-(4-cyanobenzyl)-1H-imidazol-5-ylethyl)carbonyl]-piperidine 1-t-Butoxycarbonyl-cis-3-methoxycarbonyl-piperidine-5-carboxylic acid (1.45 g, 5.06 mmol), 3-(4-cyanobenzyl) histamine (1.14 g, 5.06 mmol), HOBT (0.72 g, 5.31 mmol), EDC (1.02 g, 5.31 mmol), $Et_3N$ (0.63 mL, 4.55 mmol) were dissolved in DMF (20 mL). The solution was stirred overnight, concentrated, and partitioned between EtOAc (300 mL) and sat $NaHCO_3$ solution (200 mL). The organics were washed with brine, dried ($MgSO_4$), filtered and concentration to dryness gave the title compound after chromatography (silica gel, 1–2% $MeOH/CHCl_2$). $^1H$ NMR ($CDCl_3$); δ 7.64 (d, 2H, J=8 Hz), 7.52 (s, 1H), 7.14 (d, 2H, J=8 Hz), 6.90 (s, 1H), 6.12 (br s, 1H), 5.21 (s, 2H), 4.10–4.33 (m, 2H), 3.69 (s, 3H), 3.32–3.46 (m, 2H), 2.71–2.92 (m, 2H), 2.54–2.68 (m, 2H) 2.39–2.50 (m, 1H), 2.12–2.28 (m, 2H), 1.78–1.92 (m, 1H), 1.45 (s, 9H). FAB MS 496 (M+1)

Anal. calcd for $C_{26}H_{33}N_5O_5 \cdot 0.3\ H_2O$: C, 62.34; H, 6.76; N, 13.98; Found: C, 62.32; H, 6.61; N, 13.89.

Following the procedure of Steps D–F but substituting the 1-(t-butoxycarbonyl)piperidine-trans-3,5-dicarboxylic acid methyl ester prepared as described in Step C for the 1-(t-Butoxycarbonyl)piperidine-cis-3,5-dicarboxylic acid methyl ester utilized in Step D provided 1-(t-butoxycarbonyl)-trans-3-methoxy-carbonyl-5-[N-(1-(4-cyanobenzyl)-1H-imidazol-5-ylethyl)carbamoyl]-piperidine.

Example 2

Preparation of 1-Phenethyl-cis-3-methoxycarbonyl-5-[N-(4-cyanobenzyl-1-imidazol-5-ylethyl)carbonyl]piperidine Step A: Preparation of cis-3-Methoxycarbonyl-5-[N-(1-(4-cyanobenzyl)-1H-imidazol-5-ylethyl)carbamoyl]piperidine 1-(t-Butoxycarbonyl)-cis-3-methoxycarbonyl-5-[N-(1-(4-cyanobenzyl)-1H-imidazol-5-ylethyl)carbamoyl]piperidine (1.14 g, 2.30 mmol) was dissolved in $CH_2Cl_2$ (12 mL). Trifluoroacetic acid (6 mL) was added and the solution was stirred at ambient temperature for 3 h. The solution was concentrated to dryness to give the title compound.

Step B: Preparation of 1-Phenethyl-cis-3-methoxycarbonyl-5-[N-(1-(4-cyanobenzyl)-1H-imidazol-5-ylethyl)carbamoyl]piperidine cis-3-Methoxycarbonyl-5-[N-(1-(4-cyanobenzyl)-1H-imidazol-5-ylethyl)carbamoyl]piperidine (59.0 mg, 0.149 mmol) was dissolved in MeOH (2 mL). Phenylacetaldehyde (52.3 ul, 0.447 mmol) was added followed by sodium cyanoborohydride (28.1 mg, 0.447 mmol). The solution was stirred overnight at ambient temperature. The MeOH was removed under reduced pressure and chromatography (silica gel, 1–2% MeOH/$CH_2Cl_2$/$NH_4OH$) gave the title compound as a white solid. $^1H$ NMR ($CDCl_3$); δ 7.62 (d, 2H, J=8 Hz), 7.50 (s, 1H), 7.08–7.37 (m, 7H), 6.88 (s, 1H), 6.46 (br s, 1H), 5.22 (s, 2H), 3.64 (s, 3H), 3.27–3.19 (m, 1H), 3.03–3.20 (m, 1H), 2.86–3.00 (m, 1H), 2.73–2.85 (m, 3H), 2.44–2.70 (m, 5H), 2.26–2.41 (m, 2H), 1.98–2.10 (m, 2H), 1.80–1.95 (m, 1H). FAB MS 500 (M+1)

Using the methods described in Example 2, but substituting the requisite aldehyde for phenylacetaldehyde in Step B, the following compounds were prepared:

1-(1-Naphthylmethyl)-cis-3-methoxycarbonyl-5-[N-(1-(4-cyanobenzyl)-1H-imidazol-5-ylethyl)carbamoyl]piperidine

FAB MS 536 (M+1)

1-Benzyl-cis-3-methoxycarbonyl-5-[N-(1-(4-cyanobenzyl)-1H-imidazol-5-ylethyl)carbamoyl]piperidine

FAB MS 486 (M+1)

1-Methyl-cis-3-methoxycarbonyl-5-[N-(1-(4-cyanobenzyl)-1H-imidazol-5-ylethyl)carbamoyl]piperidine

FAB MS 410 (M+1)

1-(2-Indanyl)-cis-3-methoxycarbonyl-5-[N-(1-(4-cyanobenzyl)-1H-imidazol-5-ylethyl)carbamoyl]piperidine

FAB MS 512 (M+1)

Anal. calcd for $C_{30}H_{33}N_5O_3 \cdot 0.15\ H_2O \cdot 0.5\ CHCl_3$: C, 63.82; H, 5.94; N, 12.20; Found: C, 63.83; H, 5.95; N, 12.16.

1-(2,2-Diphenylethyl)-cis-3-methoxycarbonyl-5-[N-(1-(4-cyanobenzyl)-1H-imidazol-5-ylethyl)carbamoyl]piperidine

FAB MS 576 (M+1)

Anal. calcd for $C_{35}H_{37}N_5O_3 \cdot 0.9\ H_2O$: C, 71.02; H, 6.61; N, 11.83; Found: C, 71.08; H, 6.35; N, 11.71.

Separation of the diastereomers of this compound on a Chiralcel OD HPLC column eluting with hexane/0.2% DEA: 1-propanol, 55:45 provided the following:

1-(2,2-Diphenylethyl)-cis-3(S)-methoxycarbonyl-5-(R)-[N-(1-(4-cyanobenzyl)-1H-imidazol-5-ylethyl)carbamoyl]piperidine

FAB MS 576 (M+1)

Anal. calcd for $C_{35}H_{37}N_5O_3 \cdot 0.9\ H_2O$: C, 71.02; H, 6.61; N, 11.83; Found: C, 71.08; H, 6.35; N, 11.71.

1-(2,2-Diphenylethyl)-cis-3-(R)-methoxycarbonyl-5-(S)-[N-(1-(4-cyanobenzyl)-1H-imidazol-5-ylethyl)carbamoyl]piperidine

FAB MS 576 (M+1)

Anal. calcd for $C_{35}H_{37}N_5O_3 \cdot 0.9\ H_2O$: C, 71.02; H, 6.61; N, 11.83; Found: C, 71.08; H, 6.35; N, 11.71.

1-(3-Phenylpropyl)-cis-3-methoxycarbonyl-5-[N-(1-(4-cyanobenzyl)-1H-imidazol-5-ylethyl)carbamoyl]piperidine

FAB MS 514 (M+1)

Anal. calcd for $C_{30}H_{35}N_5O_3 \cdot 0.8\ H_2O$: C, 68.24; H, 6.99; N, 13.26; Found: C, 68.20; H, 6.69; N, 13.14.

1-(2-Methylpropyl)-cis-3-methoxycarbonyl-5-[N-(1-(4-cyanobenzyl)-1H-imidazol-5-ylethyl)carbamoyl]piperidine

FAB MS 452 (M+1)

Anal. calcd for $C_{25}H_{33}N_5O_3 \cdot 0.75\ H_2O$: C, 64.57; H, 7.48; N, 15.06; Found: C, 64.61; H, 7.19; N, 14.68.

Example 3

Preparation of 1-Phenethyl-cis-3-carboxyl-5-[N-(1-(4-cyanobenzyl)-1H-imidazol-5-ylethyl)carbamoyl]piperidine 1-Phenethyl-cis-3-methoxycarbonyl-5-[N-(1-(4-cyanobenzyl)-1H-imidazol-5-ylethyl)carbamoyl]piperidine (43.1 mg, 0.086 mmol) was dissolved in THF (4 mL) and $H_{2O}$ (1 mL). A 1N solution of $LiOH \cdot H_2O$ (86.2 uL, 0.086 mmol) was added and the solution was stirred overnight at ambient temperature. The solution was purified on a WATERS PrepPak column (0.1% TFA in $CH_3CN$: 0.1% TFA in $H_2O$, 5:95 to 95:5 gradient) to give the title compound.

$^1H$ NMR ($CD_3OD$) δ 8.72 (s, 1H), 7.78 (d, 2H, J=8 Hz), 7.43 (d, 2H, J=8 Hz), 7.20–7.40 (m, 6H), 5.55 (s, 2H), 3.75 (d,1H, J=11 Hz), 3.58 (d, 1H, J=11 Hz), 3.30–3.46 (m, 3H), 2.83–3.16 (m, 6H), 2.77 (t, 2H, J=7 Hz), 2.30 (d, 1H, J=13 Hz), 1.65–1.80 (m, 1H), 1.37 (d, 1H, J=6 Hz).

FAB MS 486 (M+1).

Example 4

Preparation of 1-Phenethyl-cis-3-[N-(1-morpholinyl)carbamoyl]-5-[N-(1-(4-cyanobenzyl)-1H-imidazol-5-ylethyl)carbamoyl]piperidine The lithium salt of 1-phenethyl-cis-3-carboxy-5-[N-(1-(4-cyanobenzyl)-1H-imidazol-5-ylethyl)carbamoyl]piperidine (55.2 mg, 0.112 mmol), morpholine (11.7 μL, 0.134 mmol), HOOBT (21.9 mg, 0.134 mmol), EDC (25.8 mg, 0.134 mmol), and $Et_3N$ (14.0 μL, 0.101 mmol) were dissolved in DMF (2 mL). The solution was stirred overnight at ambient temperature. The solution was concentrated under reduced pressure and the residue chromatographed (silica gel, 1–3% MeOH/$CH_2Cl_2$ with $NH_4OH$) to give the title compound. $^1H$ NMR ($CDCl_3$) δ 7.63 (d, 2H, J=8 Hz), 7.52 (s, 1H), 7.06–7.33 (m, 7H), 6.90 (s, 1H), 5.89 (br s, 1H), 5.21 (s, 2H), 3.55–3.76 (m, 6H), 3.43–3.53 (m, 2H), 3.28–3.40 (m, 2H), 3.09 (d, 1H, J=11 Hz), 2.91 (d, 1H, J=11 Hz), 2.71–2.86 (m, 3H), 2.53–2.70 (m, 4H), 2.36–2.46 (m, 1H), 2.25 (t, 1H, J=11 Hz), 2.15 (t, 1H, J=11 Hz), 2.71–2.93 (m, 2H).

FAB MS 555 (M+1)

Anal. calcd for $C_{32}H_{38}N_6O_3 \cdot 0.30\ H_2O \cdot 0.30\ CHCl_3$: C, 65.10; H, 6.58; N, 14.10; Found C, 65.16; H, 6.59; N, 13.86.

Using the methods described in Examples 2 and 4, the following compounds were prepared:

1-Phenethyl-cis-3-[N-(benzyl)carbamoyl]-5-[N-(1-(4-cyanobenzyl)-1H-imidazol-5-ylethyl)carbamoyl]piperidine

FAB MS 575 (M+1)

Anal. calcd for $C_{35}H_{38}N_6O_2 \cdot 0.2\ H_2O \cdot 0.35\ CH_2Cl_2$: C, 69.83; H, 6.48; N, 13.82; Found: C, 69.82; H, 6.46; N, 13.53.

1-Phenethyl-cis-3-[N-(cyclopropyl)carbamoyl]-5-[N-(1-(4-cyanobenzyl)-1H-imidazol-5-ylethyl)carbamoyl]piperidine

FAB MS 524 (M+1)

Anal. calcd for $C_{31}H_{36}N_6O_2 \cdot 0.5\ H_2O \cdot 0.25$ EtOAc: C, 69.17; H, 7.07; N, 15.12; Found: C, 69.22; H, 6.86; N, 15.12.

1-Phenethyl-cis-3-[N-(t-butyl)carbamoyl]-5-[N-(1-(4-cyanobenzyl)-1H-imidazol-5-ylethyl)carbamoyl]piperidine

FAB MS 541 (M+1)

Anal. calcd for $C_{32}H_{40}N_6O_2 \cdot 0.2\ H_2O \cdot 0.25\ CH_2Cl_2$: C, 68.49; H, 7.29; N, 14.86; Found: C, 68.48; H, 7.27; N, 14.51.

1-(2,2-Diphenylethyl)-cis-3-[N-(t-butyl)carbamoyl]-5-[N-(1-(4-cyanobenzyl)-1H-imidazol-5-ylethyl)carbamoyl]piperidine

FAB MS 617(M+1)

Anal. calcd for $C_{38}H_{44}N_6O_2 \cdot 1.05\ H_2O$: C, 71.80; H, 7.31; N, 13.22; Found: C, 71.76; H, 7.34; N, 12.83.

1-(2,2-Diphenylethyl)-cis-3-[N-(1-morpholinyl)carbamoyl]-5-[N-(1-(4-cyanobenzyl)-1H-imidazol-5-ylethyl)carbamoyl]piperidine

FAB MS 631 (M+1)

Anal. calcd for $C_{38}H_{42}N_6O_3 \cdot 0.4\ H_2O \cdot 0.4$ EtOAc: C, 70.65; H, 6.89; N, 12.48; Found: C, 70.63; H, 6.63; N, 12.46.

Separation of the diastereomers of this compound on a Chiralcel OD HPLC column eluting with hexane/0.1% DEA: ethanol, 55:45 provided the following:

1-(2,2-Diphenylethyl)-cis-3-(R)-[N-(1-morpholinyl)carbamoyl]-5-(S)-[N-(1-(4-cyanobenzyl)-1H-imidazol-5-ylethyl)carbamoyl]piperidine

FAB MS 576 (M+1)

Anal. calcd for $C_{35}H_{37}N_5O_3 \cdot 0.9\ H_2O$: C, 71.02; H, 6.61; N, 11.83; Found: C, 71.08; H, 6.35; N, 11.71.

1-(2,2-Diphenylethyl)-cis-3(S)-[N-(1-morpholinyl)carbamoyl]-5-(R)-[N-(1-(4-cyanobenzyl)-1H-imidazol-5-ylethyl)carbamoyl]piperidine

FAB MS 576 (M+1)

Anal. calcd for $C_{35}H_{37}N_5O_3 \cdot 0.9\ H_2O$: C, 71.02; H, 6.61; N, 11.83; Found: C, 71.08; H, 6.35; N, 11.71.

Example 5

Preparation of N-[1-Phenethyl-cis-5-(N'-(1-(4-cyanobenzyl)-1H-imidazol-5-ylethyl)carbamoyl)piperidine-3-carbonyl]methionine methyl ester The lithium salt of 1-phenethyl-cis-3-carboxy-5-[N-(1-(4-cyanobenzyl)-1H-imidazol-5-ylethyl)carbamoyl]piperidine (90.0 mg, 0.183 mmol), methionine (43.8 mg, 0.219 mmol), HOOBT (35.8 mg, 0.219 mmol), EDC (42.1 mg, 0.219 mmol), and Et3N (60 uL, 0.430 mL) were dissolved in DMF (2 mL). The above solution was stirred overnight at ambient temperature. The solution was concentrated under reduced pressure and the residue chromatographed (silica gel, 1–2.5% MeOH/CH$_2$Cl$_2$ with NH$_4$OH) to give the title compound. $^1$H NMR (CDCl$_3$) δ 7.63(d, 2H, J=8 Hz), 7.51 (s, 1H), 7.10–7.33 (m, 7H), 6.90 (s, 1H), 6.50–6.63 (m, 1H), 6.11–6.36 (m, 1H), 5.21 (s, 2H), 4.65–4.75 (m, 1H), 3.75 (s, 3H), 3.25–3.48 (m, 2H), 2.95–3.11 (m, 2H), 2.73–2.83 (m, 2H), 2.53–2.71 (m, 4H), 2.45–2.52 (m, 3H), 2.35–2.44 (m, 1H), 1.93–2.33 (m, 5H), 2.09 (s, 3H,), 1.67–1.85 (m, 1H). FAB MS 631(M+1)

Anal. calculated for $C_{34}H_{42}N_6O_4S \cdot 0.30\ CH_2Cl_2$: C, 62.46; H, 6.52; N, 12.72; Found C, 62.45; H, 6.53; N, 12.53.

Example 6

Preparation of N-[1-Phenethyl-cis-5-(N'-(1-(4-cyanobenzyl-1-imidazol-5-ylethyl)carbamoyl)piperidine-3-carbonyl]methionine N-[1-Phenethyl-cis-5-(N'-(4-cyanobenzyl-1-imidazol-5-ylethyl)carbamoyl) piperidine-3-carbonyl]methionine methyl ester (19 mg, 0.030 mmol) was dissolved in THF (2 mL) and H$_2$O (1 mL). A 1N solution of LiOH.H$_2$O (30.1 μL, 0.030 mmol) was added and the solution was stirred overnight at ambient temperature. The solution was purified on a RP HPLC VYDAC column (0.1% TFA in CH$_3$CN: 0.1% TFA in H$_2$O, 5:95 to 95:5 gradient) and lyophilized to give the title compound as cis diastereomers.

Diastereomer A: $^1$H NMR (CD$_3$OD) δ 8.99 (s, 1H), 7.80 (d, 2H, J=8 Hz), 7.51 (s, 1H), 7.47 (d, 2H, J=8 Hz), 7.20–7.37 (m, 5H), 5.61 (s, 2H), 4.26–4.57 (m, 1H), 3.60–3.75 (m, 2H), 3.44–3.55 (m, 1H), 3.30–3.43 (m, 3H), 2.90–3.15 (m, 6H), 2.75–2.85 (m, 2H), 2.48–2.70 (m, 2H), 2.09–2.28 (m, 2H), 2.09 (s, 3H), 1.90–2.08 (m,1H), 1.61–1.75 (m, 1H).

FAB MS 617 (M+I)

Diastereomer B: $^1$H NMR (CD$_3$OD) δ 9.02 (s, 1H), 7.81 (d, 2H, J=8 Hz), 7.53 (s, 1H), 7.51 (d, 2H, J=8 Hz), 7.22–7.39 (m, 5H), 5.62 (s, 2H), 4.29–4.59 (m, 1H), 3.76 (d, 1H, J=8 Hz), 3.68 (d,1H, J=10 Hz) 3.33–3.52 (m, 4H), 2.95–3.20 (m, 6H), 2.79–2.87 (m, 2H), 2.50–2.68 (m, 2H), 2.05–2.13 (m, 2H), 2.09 (s, 3H), 1.93–2.08 (m,1H), 1.70–1.82 (m, 1H).

FAB MS =617 (M+1)

Example 7

Preparation of 1-(t-Butoxycarbonyl)-cis-3-methoxycarbonyl-5-[N-(1-(4-cyanobenzyl)-1H-imidazol-5-yl)acetylamino]piperidine Step A: Preparation of 1-(t-Butoxycarbonyl)-cis-3-methoxycarbonyl-5-(benzyloxycarbonyl)amino piperidine 1-(t-Butoxycarbonyl)-cis-3-methoxycarbonyl-piperidine-5-carboxylic acid (1.87 g, 6.51 mmol), benzyl alcohol (1.68 mL, 16,3 mmol), diphenyl phosphorylazide (1.47 mL, 6.83 mmol), and Et$_3$N (0.95 mL, 6.83 mmol) were disolved in toluene (50 mL). The solution was heated at 90° C. for 4 h. The solution was diluted with EtOAc and was washed with Sat. NaHCO$_3$ solution, water, and brine. The organics were dried (MgSO$_4$), filtered, and concentrated to give the title compound without further purification.

Step B: Preparation of 1-(t-Butoxycarbonyl)-cis-3-methoxycarbonyl-5-amino piperidine 1-(t-Butoxycarbonyl)-cis-3-methoxycarbonyl-5-(benzyloxycarbonyl)amino piperidine (2.55 g, 6.51 mmol) was dissolved in EtOAc (75 mL), treated with Pd/C (510 mg) and shaken on a Parr apparatus at 45 psi overnight. The reaction mixture was filtered through celite, concentrated, and chromatographed (silica gel, 2% MeOH/CH$_2$Cl$_2$ with NH$_4$OH) to give the title compound.

Step C: Preparation of 1H-Imidazole-4- acetic acid methyl ester hydrochloride

A solution of 1H-imidazole-4-acetic acid hydrochloride (4.00 g, 24.6 mmol) in methanol (100 ml) was saturated with gaseous hydrogen chloride. The resulting solution was allowed to stand at room temperature (RT) for 18 hr. The solvent was evaporated in vacuo to afford the title compound as a white solid.

$^1$H NMR(CDCl$_3$, 400 MHz) δ 8.85(1H, s),7.45(1H, s), 3.89(2H, s) and 3.75(3H, s) ppm.

Step D: Preparation of 1-(Triphenylmethyl)-1H-imidazol-4-ylacetic acid methyl ester To a solution of 1H-imidazole-4-acetic acid methyl ester hydrochloride (24.85 g, 0.141 mol) in dimethyl formamide (DMF) (115 ml) was added Triethylamine (57.2 ml, 0.412 mol) and triphenylmethyl bromide(55.3 g, 0.171 mol) and the suspension was stirred for 24 hr. After this time, the reaction mixture was diluted with ethyl acetate (EtOAc) (1 l) and water (350 ml). The organic phase was washed with sat. aq. NaHCO$_3$ (350 ml), dried (Na$_2$SO$_4$) and evaporated in vacuo. The residue was purified by flash chromatography (SiO$_2$, 0–100% ethyl acetate in hexanes; gradient elution) to provide the title compound as a white solid.

$^1$H NMR (CDCl$_3$, 400 MHz) δ 7.35(1H, s), 7.31(9H, m), 7.22(6H, m), 6.76(1H, s), 3.68(3H, s) and 3.60(2H, s) ppm.

Step E: Preparation of [1-(4-Cyanobenzyl)-1H-imidazol-5-yl]acetic acid methyl ester To a solution of 1-(triphenylmethyl)-1H-imidazol-4-ylacetic acid methyl ester (8.00 g, 20.9 mmol) in acetonitrile (70 ml) was added bromo-p-toluonitrile (4. 10g, 20.92 mmol) and heated at 55° C. for 3 hr. After this time, the reaction was cooled to room temperature and the resulting imidazolium salt (white precipitate) was collected by filtration. The filtrate was heated at 55° C. for 18 hr. The reaction mixture was cooled to room temperature and evaporated in vacuo. To the residue was added EtOAc (70 ml) and the resulting white precipitate collected by filtration. The precipitated imidazolium salts were combined, suspended in methanol (100 ml) and heated to reflux for 30 min. After this time, the solvent was removed in vacuo, the resulting residue was suspended in EtOAc (75 ml) and the solid isolated by filtration and washed (EtOAc). The solid was treated with sat aq NaHCO$_3$ (300 ml) and CH$_2$Cl$_2$ (300 ml) and stirred at room temperature for 2 hr. The organic layer was separated, dried (MgSO$_4$) and evaporated in vacuo to afford the title compound as a white solid:

$^1$HNMR(CDCl$_3$, 400 MHz) δ 7.65(1H, d, J=8 Hz), 7.53 (1H, s), 7.15(1H, d, J=8 Hz), 7.04(1H, s), 5.24(2H, s), 3.62(3H, s) and 3.45(2H, s) ppm.

Step F: Preparation of [1-(4-cyanobenzyl)-1H-imidazol-5-yl]acetic acid

A solution of [1-(4-cyanobenzyl)-1H-imidazol-5-yl] acetic acid methyl ester (4.44 g, 17.4 mmol) in THF (100 ml) and 1 M lithium hydroxide (17.4 ml, 17.4 mmol) was stirred at RT for 18 hr. 1 M HCl (17.4 ml) was added and the THF was removed by evaporation in vacuo. The aqueous solution was lyophilized to afford the title compound containing lithium chloride as a white solid.

$^1$H NMR(CD$_3$OD, 400 MHz) δ 8.22(1H, s), 7.74(1H, d, J=8.4 Hz), 7.36(1H, d, J=8.4 Hz), 7.15(1H, s), 5.43(2H, s) and 3.49(2H, s) ppm.

Step G: Preparation of 1-(t-Butoxycarbonyl)-cis-3-methoxycarbonyl-5-[N-(1-(4-cyanobenzyl)-1H-imidazol-5-yl)acetylamino]-piperidine 1-(t-Butoxycarbonyl)-cis-3-methoxycarbonyl-5-amino piperidine (134 mg, 0.520 mmol), [1-(4-cyanobenzyl)-1H-imidazol-5-yl]acetic acid (147 mg, 0.520 mmol), HOBT (73,8 mg, 0.546 mmol), EDC (104 mg, 0.546 mmol), and Et$_3$N (65.2 uL, 0.468 mmol) were dissolved in DMF (4 mL) and stirred at ambient temperature overnight. The solution was concentrated under reduced pressure and the residue was chromatographed (silica gel, 0.5–2% MeOH/CH$_2$Cl$_2$ with NH$_4$OH) to give the title compound. $^1$H NMR (CDCl$_3$) d 7.64 (d, 2H, J=8 Hz), 7.52 (s, 1H), 7.19 (d, 2H, J=8 Hz), 6.90–7.05 (m, 1H), 6.98 (s, 1H), 5.22–5.35 (m, 2H), 3.78–3.91 (m, 2H), 3.69 (s, 3H), 3,57–3.64 (m, 1H), 3.45–3.56 (m, 1H), 3.34 (s, 2H), 3.05–3.30 (m, 1H), 2.55–2.68 (m, 1H), 2.05–2.13 (m, 1H), 1.55–1.70 (m, 1H), 1.42 (s, 9H). FAB MS 482 (M+1)

Anal. calculated for C$_{25}$H$_{31}$N$_5$O$_5$.0.90 H$_2$O: C, 60.32; H, 6.64; N, 14.07; Found C, 60.38; H, 6.36; N, 13.78.

Example 8

Preparation of 1-Phenethyl-cis-3-methoxycarbonyl-5-[N-(1-(4-cyanobenzyl)-1H-imidazol-5-yl) acetylamino]piperidine Step A: Preparation of cis-3-methoxycarbonyl-5-[N-(1-(4-cyanobenzyl)-1H-imidazol-5-yl) acetylamino]piperidine 1-(t-Butoxycarbonyl)-3-methoxycarbonyl-5-[N-(1-(4-cyanobenzyl)-1H-imidazol-5-yl)acetylamino]piperidine (44.6 mg, 0.093 mmol) was dissolved in CH$_2$Cl$_2$ (6 mL). Trifluoroacetic acid (3 mL) was added and the solution was stirred at ambient temperature for 4 h. The solution was concentrated under reduced pressure to give the title compound without futher purification.

Step B: Preparation of 1-Phenethyl-cis-3-methoxycarbonyl-5-[N-(1-(4-cyanobenzyl)-1H-imidazol-5-yl)acetylamino] piperidine cis-3-Methoxycarbonyl-5-[N-(1-(4-cyanobenzyl)-1H-imidazol-5-yl)acetylamino]piperidine (35.3 mg, 0.093 mmol), benzaldehyde (32.5 uL, 0.278 mmol), and sodium cyanoborohydride (17.5 mg, 0.278 mmol) was dissolved in MeOH (2 mL) and stirred overnight at ambient temperature. The solution was concentrated under reduced pressure and chromatographed (silica gel, 0.5–2% MeOH/CH$_2$Cl$_2$ with NH$_4$OH) to give the title compound. $^1$H NMR (CDCl$_3$) δ 7.62 (d, 2H, J=8 Hz), 7.52 (s, 1H), 7.11–7.31 (m, 7H), 6.99 (s, 1H), 6.25 (br s, 1H), 5.24 (s, 2H), 3.86–3.96 (m, 1H), 3.65 (s, 3H), 3.29 (s, 2H), 2.48–2.83 (m, 8H), 2.13–2.24 (m, 1H), 1.83–1.95 (m, 1H), 1.50–1.65 (m, 1H). FAB MS 486 (M+1)

Anal. calculated for C$_{28}$H$_{31}$N$_5$O$_3$.0.30 H$_2$O.0.25 CHCl$_3$: C, 65.15; H, 6.16; N, 13.45; Found C, 65.18; H, 6.15; N, 13.46.

Using the methods described in Examples 7 and 8, but substituting 1-(t-butoxycarbonyl-piperidine-3(S)-carboxylic acid for 1-(t-butoxycarbonyl)-cis-3-methoxycarbonyl-piperidine-5-carboxylic acid in Ex. 7, Step A, and diphenylacetaldehyde for phenylacetaldehyde in Ex. 8, Step B, the following compound was prepared:

1-(2,2-Diphenylethyl)-3(S)-[N-(1-(4-cyanobenzyl)-1H-imidazol-5-ylacetyl)amino]piperidine Anal. calculated for C$_{32}$H$_{33}$N$_5$.0.30 H$_2$O: C, 75.50; H, 6.65; N, 13.62; Found C, 75.51; H, 6.79; N, 13.76.

FAB MS (M+1) 504

Using the methods described for Examples 7 and 8, but substituting 1H-imidazole-4-propionic acid for 1H-imidazole-4-acetic acid in Ex. 7, Step C, the following compound was prepared:

1-(2,2-Diphenylethyl)-3(S)-[N-(1-(4-cyanobenzyl)-1H-imidazol-5-ylpropionyl)amino]piperidine Anal. calculated for C$_{33}$H$_{35}$N$_5$O.0.55 H$_2$O: C, 75.13; H, 6.90; N, 13.72; Found C, 75.15; H, 6.89; N, 13.40.

FAB MS (M+1) 518

Using the methods described for Examples 7 and 8, but substituting 1H-imidazole-4-carboxylic acid for 1H-imidazole-4-acetic acid in Ex. 7, Step C, the following compound was prepared:

1-(2,2-Diphenylethyl)-3(S)-[N-(1-(4-cyanobenzyl) -1H-imidazol-5-ylcarbonyl)amino]piperidine

FAB MS (M+1) 490

Example 9

Preparation of 1-(Diphenylacetyl)-cis-3-methoxycarbonyl-5-[N-(1-(4-cyanobenzyl)-1H-imidazol-5-ylethyl)carbamoyl]piperidine cis-3-Methoxycarbonyl-5-[N-(1-(4-cyanobenzyl)-1H-imidazol-5-ylethyl)carbamoyl]piperidine (86.8 mg, 0.219 mmol) (EXAMPLE 2, Step A) diphenyl acetic acid (302 mg, 1.42 mmol), HOOBT (54.3 mg, 0.328 mmol), EDC (63 mg, 0.328 mmol), and Et$_3$N (392 uL, 5.34 mmol) were dissolved in DMF (4 mL) and stirred at ambient temperature for 5 days. The solution was concentrated, the residue was taken up in EtOAc, washed with sat. NaHCO$_3$ solution, water, and brine. The organics were dried (MgSO$_4$), concentrated, and chromatographed (silica gel, 0.5–2% MeOH/CH$_2$Cl$_2$ with NH$_4$OH) to give the title compound. FAB MS=590 (M+1)

Anal. calculated for C$_{35}$H$_{35}$N$_5$O$_4$·0.35 CHCl$_3$·0.20 H$_2$O: C, 66.86; H, 5.67; N, 11.03; Found C, 66.86; H, 5.67; N, 11.01.

Using the methods described above but substituting 3(S)-[N-(1-(4-cyanobenzyl)-1H-imidazol-5-ylethyl)carbamoyl]piperidine (Example 11, Step E) as the starting material and the requisite acid, the following compounds were prepared:
1-(Phenylacetyl)-3(S)-[N-(1-(4-cyanobenzyl)-1H-imidazol-5-ylethyl)carbamoyl]piperidine
FAB MS (M+1) 456
1-(Diphenylacetyl)-3(S)-[N-(1-(4-cyanobenzyl)-1H-imidazol-5-ylethyl)carbamoyl]piperidine
Anal. calculated for C$_{33}$H$_{33}$N$_5$O$_2$·0.45 CH$_2$Cl$_2$·0.10 H$_2$O: C, 70.28; H, 6.01; N, 12.25; Found C, 70.24; H, 5.91; N, 12.09.
1-(3-Chlorobenzoyl)-3(S)-[N-(1-(4-cyanobenzyl)-1H-imidazol-5-ylethyl)carbamoyl]piperidine
Anal. calculated for C$_{26}$H$_{26}$N$_5$O$_2$C$_1$: C, 64.03; H, 5.64; N, 14.36; Found C, 64.09; H, 5.39; N, 14.12.
FAB MS (M+1) 476

Example 10

Preparation of 1-(2,2-Diphenylethyl)-3-[N-(1-(4-cyanobenzyl)-1H-imidazol-5-ylethyl)carbamoyl]piperidine Step A: Preparation of 1-(2,2-Diphenylethyl)-3-carboxy piperidine Nipecotic acid (300 mg, 2.38 mmol), diphenylacetaldehyde (1.26 mL, 7.13 mmol), sodium cyanoborohydride (448 mg, 7.13 mmol), and HOAc (204 uL, 3.57 mmol) were dissolved in MeOH (20 mL) and stirred at ambient temperature overnight. The solution was concentrated under reduced pressure, take up in ether and 1N NaOH, extract with ether (3×), acidify the aqueous layer with 1N HCl, and extract with EtOAc (3×). The EtOAc layers were dried (MgSO$_4$) and concentrated to give the title compound without further purification.

Step B: Preparation of 1-(2,2-Diphenylethyl)-3-[N-(1-(4-cyanobenzyl)-1H-imidazol-5-ylethyl)carbamoyl]piperidine 1-(2,2-Diphenylethyl)-3-carboxy piperidine(472 mg, 1,52 mmol),3-(4-cyanobenzyl) histamine (456 mg, 1.52 mmol) (EXAMPLE 1, Step E) HOBT (216 mg, 1.60 mmol), EDC (307 mg, 1.60 mmol), and Et$_3$N (637 uL, 4.57 mmol) were dissolved in DMF (10 mL) and was stirred overnight at ambient temperature. The solution was concentrated under reduced pressure and chromatographed (silica gel, 0.5–2% MeOH/CH$_2$Cl$_2$ with NH$_4$OH) to give the title compound $^1$H NMR (CDCl$_3$) δ 7.96 (br s, 1H), 7.60 d, 2H, J=8 Hz), 7.46 (s, 1H), 7.09–7.37 (m, 12H), 6,74 (s, 1H), 5.20 (s, 2H), 4.26 (t, 1H, J=8 Hz), 3.05–3.17 (m, 2H), 2.93–3.04 (m,1H), 2.78–2.91 (m,2H), 2.49–2,61 (m 1H), 22.40–2.47 (m, 1H), 2.15–2.30 (m, 2H), 1.95–2.14 (m, 2H), 1.86 (d, 1H, J=12 Hz), 1.29–1.55 (m, 3H). FAB MS 518 (M+1)

Anal. calculated for C$_{33}$H$_{35}$N$_5$O$_1$·0.35 CHCl$_3$·0.10 H$_2$O: C, 71.37; H, 6.38; N, 12.48; Found C, 71.41; H, 6.32; N, 12.36.

Example 11

Preparation of 1-(2-(3-Chlorophenyl)-2-phenylethyl)-3(S)-[N-(1-(4-cyanobenzyl)-1H-imidazol-5-ylethyl)carbamoyl]piperidine Step A: Preparation of S-(−)-Ethyl nipecotate Racemic ethyl nipecotate (122.5 g, 0.78 mol) was resolved with D-tartaric acid (117 g, 0.78 mol) in 95% EtOH (611 mL) following the procedure described by P. Magnus et al. (J. Org. Chem. 1991, 56, 1166–1170) to give S-(−)-ethyl nipecotate.

Step B: Preparation of Ethyl 1-(t-butoxycarbonyl)piperidine-3(S)-carboxylate

S-(−)-Ethyl nipecotate (20.0 g, 0.127 mol) was dissolved in THF (250 mL)-H$_2$O (250 mL) at ambient temperature and treated with NaHCO$_3$ (32.0 g, 0.381 mol) and di-tert-butyl-dicarbonate (43.8 mL, 0.190 mol). After stirring for 16 h, the reaction mixture was concentrated to remove THF and extracted with EtOAc (2×200 mL). The organics were combined, washed with brine, dried (MgSO$_4$), filtered and concentrated to give the title compound.

Step C: Preparation of 1-(tert-Butoxycarbonyl)piperidine-3(S)-carboxylic acid

Ethyl 1-(t-butoxycarbonyl)piperidine-3(S)-carboxylate (35.9 g, 0.099 mol) was dissolved in abs EtOH (70 mL), treated with 0.5N NaOH (418 mL, 0.209 mol), and heated at reflux for 0.75 h. The reaction mixture was cooled and extracted with EtOAc. The aqueous basic layer was cooled with ice, carefully acidified (pH 3) with 3N HCl and extracted with CH$_2$Cl$_2$ (3×100 mL). The organics were combined, dried (MgSO$_4$), filtered, and concentrated to give the title compound.

Step D: Preparation of 1-(tert-Butyloxycarbonyl)-3(S)-[N-1-(4-cyanobenzyl)-1H-imidazol-5-ylethyl)carbamoyl]piperidine 1-(tert-Butoxycarbonyl)piperidine-3(S)-carboxylic acid (5.06 g, 0.022 mol) and 3-(4-cyanobenzyl)histamine (Example 1, Step E) (6.6 g, 0.022 mol) were dissolved in DMF (30 mL) at ambient temperature and treated with EDC (5.07 g, 0.026 mol), HOBT (3.58 g, 0.26 mol), and N-methylmorpholine (12.12 mL, 0.11 mol). After stirring for 18 hr, the reaction mixture was partitioned between EtOAc(500 mL)-aq satd NaHCO$_3$ soln, the organic layer separated, washed with satd NaHCO$_3$ soln, H$_2$O, brine, dried (MgSO$_4$), filtered and concentrated to give the title compound which was used without further purification.

Step E: Preparation of 3(S)-[N-(1-(4-cyanobenzyl)-1H-imidazole-5-ethyl)carbamoyl]piperidine dihydrochloride 1-(tert-Butyloxycarbonyl)-3(S)-[N-1-(4-cyanobenzyl)-1H-imidazol-5-ylethyl)carbamoyl]piperidine (9.25 g, 0.021 mol) was dissolved in EtOAc (500 mL) with stirring at 0° C. in an ice-water bath. HCl gas was bubbled through the solution for 5 min., the flask stoppered, and the solution stirred for 1 hr. The solution was purged with N$_2$ then concentrated to dryness to give the title compound. $^1$H NMR (CD$_3$OD); δ 9.02 (s, 1H), 7.80 (d, 2H, J=8 Hz), 7.52 (s, 1H), 7.48 (d, 2H, J=8 Hz),5.62 (s, 2H), 3.42 (td, 2H, J=3,7 Hz), 3.00–3.26 (m, 4H), 2.80 (t, 2H, J=7 Hz), 2.67–2.78 (m, 1H), 1.65–2.0 (m, 4H).

FAB MS 338 (M+1).

Step F: Preparation of 2-(3-Chlorophenyl)-2-phenyl oxirane

A 250 mL-round bottom flask was charged with NaH (60% dispersion in mineral oil) (1.92 g, 0.048 mol), washed with petroleum ether, then treated with dry DMSO (40 mL) under N$_2$. To this reaction mixture was added trimethylsulfoxonium iodide (10.56 g, 0.048 mol) through a solid addition funnel over 15 min. After stirring for 0.5 hr, a solution of 3-chlorobenzophenone (8.66 g, 0.04 mol) in DMSO (15 mL) was added dropwise, and the mixture was heated at 55° C. for 2 hr. The mixture was added to ice-water, extracted with ether (3×100 mL), the organics combined, dried (MgSO$_4$), filtered, and concentrated to give the title compound.

Step G: Preparation of 2-(3-Chlorophenyl)-2-phenyl carboxaldehyde 2-(3-Chlorophenyl)-2-phenyl oxirane (10.19 g, 0.04 mol) was dissolved in dry benzene (250 mL), treated with BF$_3$.etherate (0.2 mL) and stirred at ambient temperature for 1 hr. The benzene was extracted with H$_2$O until the aqueous layer was no longer acidic, then concentrated to dryness to give the title compound after chromatography (5% EtOAc/hexane on SiO$_2$). $^1$H NMR (CDCl$_3$) δ 9.95 (s, 1H), 7.1–7.5 (m, 9H), 4.85 (s, 1H).

Step H: Preparation of 1-(2-(3-Chlorophenyl)-2-phenylethyl)-3-(S)-[N-(1-(4-cyanobenzyl)-1H-imidazol-5-ylethyl)carbamoyl]piperidine 3(S)-[N-(1-(4-cyanobenzyl)-1H-imidazol-5-ylethyl)carbamoyl]piperidine dihydrochloride (0.256 g, 0.623 mmol) was dissolved in MeOH (10 mL), the pH adjusted to 5 with Et$_3$N, and 2-(3-chlorophenyl)-2-phenylcarboxaldehyde (0.427 g, 1.87 mmol) and NaCNBH$_3$ (0.078 g, 1.25 mmol) were added. After stirring for 18 hr at ambient temperature, the reaction mixture was partitioned between EtOAc and satd NaHCO$_3$ soln, the organic layer separated, washed with H$_2$O, brine, dried (MgSO$_4$), filtered and concentrated to dryness to give the title compound after chromatography on SiO$_2$ eluting with 3% MeOH/CH$_2$Cl$_2$ w/NH$_4$OH. $^1$H NMR (CD$_3$OD); δ 7.88 (br s, 1H), 7.60 (d, 2H, J=8 Hz), 7.47 (s, 1H), 7.07–7.36 (m, 11H), 6.76 (d, 1H, J=2.7 Hz), 5.21 (s, 2H), 4.24 (td, 1H, J=2, 8 Hz), 2.80–3.13 (m, 5H), 2.50–2.65 (m, 1H), 2.44 (s, 1H), 2.0–2.3 (m, 4H), 1.86 (d, 1H, J=12 Hz), 1.3–1.55 (m, 3H). FAB MS 552 (M+1).

Anal. calculated for C$_{33}$H$_{34}$N$_5$OCl.0.40 H$_2$O: C, 70.87; H, 6.27; N, 12.52; Found C, 70.84; H, 6.31; N, 12.39.

Using the methods described above, but substituting the requisite ketone in Step F, the following compounds were prepared:

1-(Dibenzylsuberylmethyl)-3(S)-[N-(1-(4-cyanobenzyl)-1H-imidazol-5-ylethyl)carbamoyl]piperidine Anal. calculated for C$_{35}$H$_{37}$N$_5$O.0.45 H$_2$O: C, 76.18; H, 6.92; N, 12.69; Found C, 76.15; H, 6.84; N, 12.49.

1-(2-(3-Methylphenyl)-2-phenylethyl)-3(S)-[N-(1-(4-cyanobenzyl)-1H-imidazol-5-ylethyl)carbamoyl]piperidine Anal. calculated for C$_{34}$H$_{37}$N$_5$O.0.40 H$_2$O: C, 75.78; H, 7.07; N, 13.00; Found C, 75.81; H, 7.01; N, 13.20

1-(2-(3-Trifluoromethylphenyl)-2-phenylethyl)-$^3$(S)-[N-(1-(4-cyanobenzyl)-1H-imidazol-5-ylethyl)carbamoyl]piperidine Anal. calculated for C$_{34}$H$_{34}$N$_5$OF$_3$.0.20 H$_2$O: C, 69.30; H, 5.88; N, 11.88; Found C, 69.32; H, 5.84; N, 12.04.

1-(2-(2-Chlorophenyl)-2-phenylethyl)-3(S)-[N-(1-(4-cyanobenzyl)-1H-imidazol-5-ylethyl)carbamoyl]piperidine Anal. calculated for C$_{33}$H$_{34}$N$_{50}$Cl.0.50 H$_2$O: C, 70.64; H, 6.29; N, 12.48; Found C, 70.67; H, 6.16; N, 12.50.

1-(2-(4-Chlorophenyl)-2-phenylethyl)-3(S)-[N-(1-(4-cyanobenzyl)-1H-imidazol-5-ylethyl)carbamoyl]piperidine Anal. calculated for C$_{33}$H$_{34}$N$_{50}$Cl: C, 70.98; H, 6.26; N, 12.54; Found C, 71.02; H, 6.22; N, 12.40.

1-(2-(3-Aminomethylphenyl)-2-phenylethyl)-$^3$(S)-[N-(1-(4-cyanobenzyl)-1H-imidazol-5-ylethyl)carbamoyl]piperidine Anal. calculated for C$_{34}$H$_{38}$N$_6$O.4.25 CF$_3$CO$_2$H.0.45 H$_2$O: C, 49.11; H, 4.18; N, 8.09; Found C, 49.11; H, 4.16; N, 8.15.

Using the methods described above, but substituting commercially available aldehydes for 2-(3-chlorophenyl)-2-phenylcarboxaldehyde in Step H, the following compounds were prepared:

1-(2-Phenethyl)-3(S)-[N-(1-(4-cyanobenzyl)-1H-imidazol-5-ylethyl)carbamoyl]piperidine

FAB MS (M+1) 442

1-(2-Phenethyl)-3-(R)-[N-(1-(4-cyanobenzyl)-1H-imidazol-5-ylethyl)carbamoyl]piperidine Anal. calculated for C$_{27}$H$_{31}$N$_5$O.2.0 HCl 1.60 H$_2$O: C, 59.69; H, 6.72; N, 12.89; Found C, 59.72; H, 7.18; N, 11.91.

FAB MS (M+1) 442

1-(3-Phenylpropyl)-3(S)-[N-(1-(4-cyanobenzyl)-1H-imidazol-5-ylethyl)carbamoyl]piperidine Anal. calculated for C$_{28}$H$_{33}$N$_5$O.2.75 CF$_3$CO$_2$H.0.75 H$_2$O: C, 51.14; H, 4.80; N, 8.95; Found C, 51.42; H, 4.78; N, 9.00.

FAB MS (M+1) 456

1-(2-Benzyl)-3-[N-(1-(4-cyanobenzyl)-1H-imidazol-5-ylethyl)carbamoyl]piperidine

Anal. calculated for C$_{26}$H$_{29}$N$_5$O.2.80 CF$_3$CO$_2$H.0.70 H$_2$O: C, 49.98; H, 4.41; N, 9.22; Found C, 49.98; H, 4.39; N, 9.67.

FAB MS (M+1) 428

1-(2-Chlorobenzyl)-3-[N-(1-(4-cyanobenzyl)-1H-imidazol-5-ylethyl)carbamoyl]piperidine Anal. calculated for C$_{26}$H$_{28}$N$_5$OCl.3.25 CF$_3$CO$_2$H.0.50 H$_2$O: C, 46.38; H, 3.86; N, 8.32; Found C, 46.39; H, 3.82; N, 8.54.

FAB MS (M+1) 462

1-(3-Chlorobenzyl)-3-[N-(1-(4-cyanobenzyl)-1H-imidazol-5-ylethyl)carbamoyl]piperidine Anal. calculated for C$_{26}$H$_{28}$N$_5$OCl.2.75 CF$_3$CO$_2$H.0.40 H$_2$O: C, 48.33; H, 4.06; N, 8.95; Found C, 48.30; H, 4.06; N, 9.16.

FAB MS (M+1) 462

1-(3-Chlorobenzyl)-3(S)-[N-(1-(4-cyanobenzyl)-1H-imidazol-5-ylethyl)carbamoyl]piperidine Anal. calculated for C$_{26}$H$_{28}$N$_5$OCl.0.45 H$_2$O: C, 66.43; H, 6.20; N, 14.90; Found C, 66.43; H, 6.07; N, 14.97.

1-(2,2-Diphenyl-2-hydroxyethyl)-3(S)-[N-(1-(4-cyanobenzyl)-1H-imidazol-5-ylethyl)carbamoyl]piperidine Anal. calculated for C$_{33}$H$_{35}$N$_5$O$_2$.0.25 H$_2$O: C, 73.65; H, 6.65; N, 13.01; Found C, 73.69; H, 6.79; N, 12.84.

FAB MS (M+1) 534

1-(3-Methoxybenzyl)-3(S)-[N-(1-(4-cyanobenzyl)-1H-imidazol-5-ylethyl)carbamoyl]piperidine

FAB MS (M+1) 458

1-(3,5-Dichlorobenzyl)-3(S)-[N-(1-(4-cyanobenzyl)-1H-imidazol-5-ylethyl)carbamoyl]piperidine Anal. calculated for C$_{26}$H$_{27}$N$_5$OCl$_2$.0.40 H$_2$O: C, 62.01; H, 5.56; N, 13.91; Found C, 61.98; H, 5.55; N, 13.57.

1-(3-Trifluoromethoxybenzyl)-3(S)-[N-(1-(4-cyanobenzyl)-1H-imidazol-5-ylethyl)carbamoyl]piperidine Anal. calculated for C$_{27}$H$_{28}$N$_5$O$_2$F$_3$.2.0 HCl.1.85 H$_2$O: C, 52.49; H, 5.50; N, 11.34; Found C, 52.50; H, 5.72; N, 11.34.

1-(2,5-Dimethylbenzyl)-3(S)-[N-(1-(4-cyanobenzyl)-1H-imidazol-5-ylethyl)carbamoyl]piperidine Anal. calculated for C$_{28}$H$_{338}$N$_5$O.0.40 H$_2$O: C, 72.67; H, 7.36; N, 15.13; Found C, 72.67; H, 7.27; N, 14.77.

1-(3-Trifluoromethylbenzyl)-3(S)-[N-(1-(4-cyanobenzyl)-1H-imidazol-5-ylethyl)carbamoyl]piperidine Anal. calculated for C$_{27}$H$_{28}$N$_5$OF$_3$.0.15 H$_2$O: C, 65.09; H, 5.73; N, 14.06; Found C, 65.14; H, 5.83; N, 14.01.

1-(3-Bromobenzyl)-3(S)-[N-(1-(4-cyanobenzyl)-1H-imidazol-5-ylethyl)carbamoyl]piperidine Anal. calculated for $C_{26}H_{28}N_5OBr.2.0$ HCl.1.0 $H_2O$: C, 52.28; H, 5.40; N, 11.72; Found C, 52.33; H, 5.51; N, 11.26.

1-(3-Methylbenzyl)-3(S)-[N-(1-(4-cyanobenzyl)-1-H-imidazol-5-ylethyl)carbamoyl]piperidine Anal. calculated for $C_{27}H_{31}N_5O.2.0$ HCl.1.30 $H_2O$: C, 60.54; H, 6.70; N, 13.07; Found C, 60.58; H, 6.68; N, 12.22.

1-Isobutyl-3(S)-[N-(1-(4-cyanobenzyl)-1H-imidazol-5-ylethyl)carbamoyl]piperidine Anal. calculated for $C_{23}H_{31}N_5$.2.3 HCl.0.95 $H_2O$: C, 55.87; H, 7.17; N, 14.16; Found C, 55.91; H, 7.38; N, 14.01.

FAB MS (M+1) 394

1-(2-Methyl-2-phenylethyl)-3-[N-(1-(4-cyanobenzyl)-1H-imidazol-5-ylethyl)carbamoyl]piperidine Anal. calculated for $C_{34}H_{37}N_5O.0.40$ $H_2O$: C, 75.78; H, 7.07; N, 13.00; Found C, 75.81; H, 7.01; N, 13.20.

FAB MS (M+1) 532

Using the methods described above, but substituting 1-morpholinyl-α-phenylacetaldehyde or 1-piperidinyl-α-phenylacetaldehyde (prepared following the procedure described by L. Duhamel, P. Duhamel, P. Siret, *Bull Soc. Chim. Fr.,* [7–8], 2460–2466 (1973)) in Step H, the following compounds were prepared:

1-(2-(1-Morpholinyl)-2-phenylethyl)-3(S)-[N-(1-(4-cyanobenzyl)-1H-imidazol-5-ylethyl)carbamoyl]piperidine-Diastereomer A Anal. calculated for $C_{31}H_{38}N_6O_2.0.80$ $H_2O.0.25$ EtOAc: C, 68.25; H, 7.45; N, 14.92; Found C, 68.27; H, 7.13; N, 14.92.

1-(2-(1-Morpholinyl)-2-phenylethyl)-3(S)-[N-(1-(4-cyanobenzyl)-1H-imidazol-5-ylethyl)carbamoyl]piperidine-Diastereomer B Anal. calculated for $C_{31}H_{38}N_6O_2.0.65$ $H_2O$: C, 69.16; H, 7.36; N, 15.61; Found C, 69.15; H, 7.31; N, 15.48.

1-(2-(1-Piperidinyl)-2-phenylethyl)-3(S)-[N-(1-(4-cyanobenzyl)-1H-imidazol-5-ylethyl)carbamoyl]piperidine

FAB MS (M+1) 525

Using the methods described in Examples 11 and 1, but substituting 2-methylhistamine for the starting material in Ex. 1, Step E, the following compound was prepared:

1-(2,2-Diphenylethyl)-3(S)-[N-(1-(4-cyanobenzyl)-2-methyl-1H-imidazol-5-ylethyl)carbamoyl]piperidine Anal. calculated for $C_{34}H_{37}N_5O.0.45$ $H_2O$: C, 75.65; H, 7.08; N, 12.97; Found C, 75.65; H, 6.93; N, 12.68.

Using the methods described in Examples 11 and 1, but substituting 4-methoxybenzyl bromide for 4-cyanobenzyl bromide in Ex. 1, Step E, the following compound was prepared:

1-(2,2-Diphenylethyl)-3(S)-[N-(1-(4-methoxybenzyl)-1H-imidazol-5-ylethyl)carbamoyl]piperidine Anal. calculated for $C_{33}H_{38}N_4O_2.2.0$ HCl.1.40 $H_2O$: C, 63.84; H, 6.95; N, 9.02; Found C, 63.91; H, 7.33; N, 9.45.

Example 12

Preparation of 1-(Diphenylmethyl)-3(S)-[N-(1-(4-cyanobenzyl)-1H-imidazol-5-ylethyl)carbamoyl]piperidine 3(S)-[N-1-(4-Cyanobenzyl)-1H-imidazol-5-ylethyl)carbamoyl]piperidine dihydrochloride (Example 11, Step E) (0.203 g, 0.494 mmol) was dissolved in DMF (10 mL), treated with $K_2CO_3$ (0.503 g, 1.976 mmol) and bromodiphenylmethane (0.134 g, 0.543 mmol), and stirred for 48 hr at ambient temperature. The reaction mixture was concentrated, dissolved in EtOAc, washed with aq satd NaHCO$_3$ soln, $H_2O$, brine, and dried (MgSO$_4$), filtered and concentrated to give the title compound after SiO$_2$ chromatography eluting with 0–3% MeOH: CH$_2$Cl$_2$ with NH$_4$OH.

Anal. calculated for $C_{32}H_{33}N_5O.0.75$ $H_2O$: C, 74.31; H, 6.72; N, 13.54; Found C, 74.37; H, 6.48; N, 13.37.

FAB MS (M+1) 504.

Using the method described above, but substituting the requisite bromide or mesylate for bromodiphenylmethane, the following compounds were prepared:

1-(3-Methoxyphenethyl)-3(S)-[N-(1-(4-cyanobenzyl)-1H-imidazol-5-ylethyl)carbamoyl]piperidine Anal. calculated for $C_{28}H_{33}N_5O_2.2$ HCl.1.95 $H_2O$: C, 58.02; H, 6.76; N, 12.08; Found C, 58.01; H, 7.03; N, 11.99.

FAB MS (M+1) 472.

1-(1-Naphthylethyl)-3(S)-[N-(1-(4-cyanobenzyl)-1H-imidazol-5-ylethyl)carbamoyl]piperidine Anal. calculated for $C_{31}H_{33}N_5O.0.90$ $H_2O$: C, 73.32; H, 6.91; N, 13.79; Found C, 73.32; H, 7.04; N, 13.46.

1-(3-Chlorophenethyl)-3(S)-[N-1-(4-cyanobenzyl)-1H-imidazol-5-ylethyl)carbamoyl]piperidine Anal. calculated for $C_{27}H_{30}N_5OCl.2HCl.1.65$ $H_2O$: C, 56.04; H, 6.15; N, 12.10; Found C, 56.09; H, 6.43; N, 11.77.

1-(α-Methylbenzyl)-3(S)-[N-(1-(4-cyanobenzyl)-1H-imidazol-5-ylethyl)carbamoyl]piperidine Anal. calculated for $C_{27}H_{31}N_5O.0.45$ $H_2O$: C, 72.12; H, 7.15; N, 15.57; Found C, 71.80; H, 6.81; N, 15.96.

FAB MS (+1) 442.

Using the methods described in Examples 12 and 1, but substituting 2-methylhistamine for the starting material in Ex. 1, Step E, the following compound was prepared:

1-(2-Diphenylmethyl)-3(S)-[N-(1-(4-cyanobenzyl)-2-methyl-1H-imidazol-5-ylethyl)carbamoyl]piperidine Anal. calculated for $C_{33}H_{35}N_5O.0.40$ EtOAc: C, 75.11; H, 6.96; N, 12.66; Found C, 75.15; H, 7.24; N, 12.60.

FAB MS (M+1) 518.

Example 13

Preparation of 1-(α-Toluenesulfonyl)-3(S)-[N-(1-(4-cyanobenzyl)-1H-imidazol-5-ylethyl)carbamoyl]piperidine 3(S)-[N-1-(4-Cyanobenzyl)-1H-imidazol-5-ylethyl)carbamoyl]piperidine dihydrochloride (Example 11, Step E) (0.210 g, 0.512 mmol) was dissolved in CH$_2$Cl$_2$ (6 mL), treated with Et$_3$N (0.285 mL, 2.046 mmol) and α-toluenesulfonyl chloride (0.195 g, 1.023 mmol) and stirred at ambient temperature for 2 hr. The reaction mixture was concentrated to dryness, partitioned between EtOAc and satd NaHCO$_3$ soln, the organic layer separated, washed with brine, and dried (MgSO$_4$). Filtration and concentration to dryness gave the title compound after purification on a Waters Prep Pak eluting with 0.1 %TFA/H$_2$O: 0.1 %TFA/CH$_3$CN, 95:5 to 5:95. 1H NMR (CD$_3$OD); δ 8.80 (s, 1H), 8.02–8.12 (m, 1H), 7.78 (d, 2H, J=8 Hz), 7.34–7.5 (m, 7H), 5.54 (s, 2H), 4.32 (s, 2H), 3.2–3.56 (m, 4H), 2.65–2.95 (m, 4H), 2.25–2.4 (m, 1H), 1.4–1.8 (m, 4H). FAB MS 492 (M+1).

Using this procedure, but substituting the sulfonyl chloride, the following compounds were prepared:

1-(Benzenesulfonyl)-3(S)-[N-(1-(4-cyanobenzyl)-1H-imidazol-5-ylethyl)carbamoyl]piperidine

FAB MS (M+1) 478.

1-(1-Naphthylenesulfonyl)-3(S)-[N-(1-(4-cyanobenzyl)-1H-imidazol-5-ylethyl)carbamoyl]piperidine Anal. calculated for $C_{29}H_{29}N_5O_3S.1.50$ $CF_3CO_2H.0.10$ $H_2O$: C, 54.87; H, 4.42; N, 10.00; Found C, 54.84; H, 4.31; N, 10.19.

1-(3-Chlorobenzenesulfonyl)-3(S)-[N-(1-(4-cyanobenzyl)-1H-imidazol-5-ylethyl)carbamoyl]piperidine Anal. calculated for $C_{25}H_{26}N_5O_3SCl.0.55$ $H_2O$: C, 57.53; H, 5.23; N, 13.42; Found C, 57.51; H, 5.20; N, 13.28.

1-(3,5-Dichlorobenzenesulfonyl)-3(S)-[N-(1-(4-cyanobenzyl)-1H-imidazol-5-ylethyl)carbamoyl]piperidine Anal. calculated for $C_{25}H_{25}N_5O_3SCl.0.30\ H_2O$: C, 54.41; H, 4.68; N, 12.69; Found C, 54.43; H, 4.82; N, 12.49.

1-(α-Toluenesulfonyl)-3-(R)-[N-(1-(4-cyanobenzyl)-1H-imidazol-5-ylethyl)carbamoyl]piperidine Anal. calculated for $C_{26}H_{29}N_5O_3S.0.35\ H_2O$: C, 62.72; H, 6.01; N, 14.07; Found C, 62.73; H, 5.85; N, 13.84.

1-(α-Toluenesulfonyl)-cis-3-methoxycarbonyl-5-[N-(1-(4-cyanobenzyl)-1H-imidazol-5-ylethyl)carbamoyl]piperidine

FAB MS (M+1) 550

1-(Methanesulfonyl)-3(S)-[N-(1-(4-cyanobenzyl)-1H-imidazol-5-ylethyl)carbamoyl]piperidine Anal. calculated for $C_{20}H_{25}N_5O_3S.0.25\ CH_2Cl_2$: C, 55.68; H, 5.89; N, 16.04; Found C, 56.04; H, 5.89; N, 15.70.

FAB MS (M+1) 416

Example 14

Preparation of 1-(Diphenylcarbamoyl)-3(S)-[N-(1-(4-cyanobenzyl)-1H-imidazol-5-ylethyl)carbamoyl]piperidine 3(S)-[N-(1-(4-cyanobenzyl)-1H-imidazol-5-ylethyl)carbamoyl]piperidine dihydrochloride (Example 11, Step E) (0.346 g, 0.843 mmol) was dissolved in $CH_2Cl_2$ (10 mL), treated with $Et_3N$ (0.587 mL, 4.2 mmol) and diphenylcarbamoyl chloride (0.390 g, 1.686 mmol) and stirred at ambient temperature for 1 hr. The reaction mixture was concentrated to dryness, partitioned between EtOAc and satd $NaHCO_3$ soln, the organic layer separated, washed with brine, and dried ($MgSO_4$). Filtration and concentration to dryness gave the title compound after purification on a silica gel column eluting with 0–2% $MeOH/CH_2Cl_2$. Anal. calculated for $C_{32}H_{32}N_6O_2.0.95\ H_2O$: C, 69.91; H, 6.22; N, 15.29; Found C, 69.97; H, 6.15; N, 14.80.

FAB MS (M+1) 533.

Using phenylisocyanate in place of diphenylcarbamoyl chloride provided:

1-(Phenylcarbamoyl)-3(S)-[N-(1-(4-cyanobenzyl)-1H-imidazol-5-ylethyl)carbamoyl]piperidine Anal. calculated for $C_{26}H_{28}N_6O_2.0.45\ H_2O.0.45\ EtOAc$: C, 66.21; H, 6.50; N, 16.66; Found C, 66.18; H, 6.56; N, 16.71.

FAB MS (M+1) 457.

Example 15

Preparation of 1-[2-(2-Pyridyl)-2-phenyl-2-hydroxyethyl]-3(S)-[N-(1-(4-cyanobenzyl)-1H-imidazol-5-ylethyl)carbamoyl]piperidine Step A: Preparation of Ethyl 1-[2-(2-pyridyl)-2-phenyl-2-hydroxyethyl]piperidine-3(S)-carboxylate 2-(2-pyridyl)-2-phenyl oxirane (prepared following the procedure of Example 11, Step F) (0.106 g, 0.537 mmol) and S-(−)-ethyl nipecotate (0.093 g, 0.591 mmol) in EtOH (0.90 mL) were heated at 50° C. in a sealed tube with stirring for 24 hr. The reaction mixture was dissolved in EtOAc, washed with brine, dried ($Na_2SO_4$), filtered, and concentrated to dryness to give the title compound.

Step B: Preparation of 1-[2-(2-Pyridyl)-2-phenyl-2-hydroxyethyl]piperidine-3(S)-carboxylic acid Ethyl 1-[2-(2-pyridyl)-2-phenyl-2-hydroxyethyl]piperidine-3(S)-carboxylate (0.187 g, 0.527 mmol) was dissolved in EtOH (5 mL), 1N NaOH (0.791 mL, 0.791 mmol) and $H_2O$ (5 mL) added, and the reaction mixture heated at reflux for 3 hr. Neutralization with 1N HCl (to a pH of 6) and concentration to dryness gave the title compound which was used without further purification.

Step C: Preparation of 1-[2-(2-Pyridyl)-2-phenyl-2-hydroxyethyl]-3(S)-[N-(1-(4-cyanobenzyl)-1H-imidazol-5-ylethyl)carbamoyl]piperidine 1-[2-(2-Pyridyl)-2-phenyl-2-hydroxyethyl]piperidine-3 (S)-carboxylic acid (0.172 g, 0.527 mmol) was suspended in DMF (5 mL) and treated with EDC (0.106 g, 0.553 mmol), HOBT (0.068 g, 0.501 mmol), followed by N-methylmorpholine to adjust the pH to 7, and 4-(4-Cyanobenzyl) histamine dihydrochloride (0.158 g, 0.527 mmol). stirring at ambient temperature for 18 hr under $N_2$, the reaction mixture was concentrated, partitioned between $CH_2Cl_2$ and $H_2O$, the organic phase washed with aq satd $NaHCO_3$ soln, brine, and dried ($Na_2SO_4$). Filtration and concentration to dryness gave the title compound after purification by RP HPLC on a Waters Prep Pak eluting with 0.1%$TFA/H_2O$: 0.1%$TFA/CH_3CN$, 95:5 to 5:95. FAB MS (M+1) 535.

Anal. calculated for $C_{32}H_{34}N_6O_2.3.0\ HCl.2.10\ H_2O$: C, 56.37; H, 6.09; N, 12.33; Found C, 56.36; H, 6.14; N, 11.54.

Example 16

Preparation of 1-(2-Pyridylethyl)-3(S)-[N-(1-(4-cyanobenzyl)-1H-imidazol-5-ylethyl)carbamoyl]piperidine Step A: Preparation of Ethyl 1-(2-pyridylethyl) piperidine-3(S)-carboxylate S-(−)-Ethyl nipecotate (0.650 g, 4.14 mmol) and 2-vinylpyridine (0.670 mL, 6.21 mmol) were dissolved in n-butanol (50 mL) with stirring under Ar and heated at reflux for 18 hr. The reaction mixture was concentrated, and the residue chromatographed on $SiO_2$ eluting with $CH_2Cl_2$:MeOH, 95:5 to 9:1 to give the title compound.

$^1H$ NMR ($CDCl_3$); δ 8.52 (dd, 1H, J=1, 4 Hz), 7.58 (td, 1H, J=1.8, 8 Hz), 7.26 (s, 1H), 7.18 (d, 1H, J=8 Hz), 7.106 (dd, 1H, J=4, 6 Hz), 4.12 (q, 2H, J=7 Hz), 3.07 (d, 1H, J=10 Hz), 2.95–3.03 (m, 2H), 2.737–2.88 (m, 3H), 2.52–2.62 (m, 1H), 2.28 (t, 1H, J=10 Hz), 2.11 (td, 1H, J=3, 10 Hz), 1.9–2.0 (m, 1H), 1.4–1.8 (m, 4H), 1.25 (t, 3H, J=7 Hz).

Step B: Preparation of 1-(2-Pyridylethyl) piperidine-3(S)-carboxylic acid

Following the procedure of Example 15, Step B, the title compound was prepared.

Step C: Preparation of 1-(2-Pyridylethyl)-3(S)-[N-(1-(4-cyanobenzyl)-1H-imidazol-5-ylethyl)carbamoyl]piperidine Following the procedure of Example 15, Step C, the title compound was prepared. FAB MS (M+1) 413.

Example 17

Preparation of 1-Phenyl-3(S)-[N-(1-(4-cyanobenzyl)-1H-imidazol-5-ylethyl)carbamoyl]piperidine Step A: Preparation of Ethyl 1-phenyl-(S)-piperidine carboxylate To a solution of S-ethyl nipecotate (0.3 g, 1.91 mmol) in $CH_2C_{12}$ (20 mL) was added triphenylbismuth (1.68 g, 3.82 mmol), copper acetate (0.52 g, 2.86 mmol), and $Et_3N$ (0.39 mL, 2.86 mmol). The resulting mixture was stirred at 25° C. for 18 hr. The reaction was partitioned with $CH_2Cl_2$(50 ml) and satd $NaHCO_3$ (30 mL), the organic layer washe with brine (30 ml) and dried ($MgSO_4$). Filtration and concentration in vacuo gave the title compound after $SiO_2$ chromatography eluting with hexane:ethyl acetate 95:5.

Step B: Preparation of 1-Phenyl-(S)-piperidine carboxylic acid

Following the procedure of Example 15, Step B, the title compound was prepared.

Step C: Preparation of 1-Phenyl-3(S)-[N-(1-(4-cyanobenzyl)-1H-imidazol-5-ylethyl)carbamoyl]piperidine Following the procedure of Example 15, Step C, the title compound was prepared. Purification was carried out on RP HPLC Waters Prep Pak eluting with 0.1%TFA/H$_2$O: 0.1%TFA/CH$_3$CN, 95:5 to 5:95.

Anal. calculated for C$_{25}$H$_{27}$N$_5$O.3.1 CF$_3$CO$_2$H.0.8 H$_2$O: C, 47.96; H, 4.09; N, 8.96; Found C, 47.94; H, 4.12; N, 8.97.

Using the methods above, but substituting tri-3-methylphenylbismuth for triphenylbismuth, the following compound was prepared:

1-(3-Methylphenyl)-3(S)-[N-(1-(4-cyanobenzyl)-1H-imidazol-5-ylethyl)carbamoyl]piperidine Anal. calculated for C$_{26}$H$_{29}$N$_5$O.2.9 CF$_3$CO$_2$H.0.8 H$_2$O: C, 49.44; H, 4.37; N, 9.06; Found C, 49.43; H, 4.35; N, 9.15.

Example 18

Preparation of 1-(2,2-Diphenylethyl)-3(S)-[2-(1-(4-cyanobenzyl)-1H-imidazol-5yl)ethylthiomethyl] piperidine Step A: Preparation of Ethyl 1-(2,2-Diphenylethyl)-3(S)-piperidine carboxylate Following the procedure outlined in Example 10, Step A, but using ethyl 3(S)-piperidine carboxylate instead of nipecotic acid, the title compound was prepared.

Step B: Preparation of 1-(2,2-Diphenylethyl)-3(S)-hydroxymethyl-piperidine

Ethyl 1-(2,2-Diphenylethyl)-3(S)-piperidine carboxylate (4.90 g, 0.014 mol) dissolved in dry ether (40 mL) was added to a suspension of lithium aluminum hydride (1.93 g, 0.051 mol) in dry ether (40 mL). The solution was refluxed until the starting material was consumed and then was quenched with saturated potassium sodium tartrate solution (100 mL) and stirred for 2 hr. The layers were separated and the aqueous layer extracted with ether (2×). The combined organic extracts were dried (MgSO$_4$) and concentrated to yield the title compound without further purification.

Step C: Preparation of 1-(2,2-Diphenylethyl)-3(S)-tosyloxymethyl-piperidine 1-(2,2-Diphenylethyl)-3(S)-hydroxymethyl-piperidine (1.01 g, 3.41 mmol) was dissolved in dry pyridine (25 mL) and tosyl chloride (0.684 g, 3.58 mmol) was added to the solution After stirring at ambient temperature for 18 hr, the solution was concentrated, the residue taken up in EtOAc, washed with sat. NaHCO$_3$ solution, H$_2$O, brine, and dried (MgSO$_4$). Filtration and concentration gave the title compound without further purification.

Step D: Preparation of 1-(2,2-Diphenylethyl)-3(S)-acetylthiomethyl-piperidine 1-(2,2-Diphenylethyl)-3(S)-tosyloxymethyl-piperidine (1.35 g, 3.23 mmol), potassium thiol acetate (1.47 g, 12.9 mmol) and DMF (30 mL) were heated at 100° C. for 4 hr. The solution was poured into ice and the resulting green precipitate was dissolved in ETOAc. The organics were washed with H$_2$O (2×), sat. NaHCO$_3$ solution, brine, dried (MgSO4) and concentrated to give the title compound without further purification.

Step D: Preparation of the disulfide of 1-(2,2-Diphenylethyl)-3(S)-mercaptomethyl-piperidine 1-(2,2-Diphenylethyl)-3(S)-acetylthiomethyl-piperidine (0.523 g, 1.47 mmol), EtOH (20 mL), and NaOH (0.5N, 20 mL) was refluxed 3 hr. The solution was concentrated to remove ethanol and the remaining aqueous solution was decanted from the green oil. The oil was washed with water (2×) and decanted. The oil was dried under reduced pressure to give the title compound without further purification.

Step E: Preparation of 1-(2,2-Diphenylethyl)-3(S)-mercaptomethyl-piperidine

The disulfide (0.10 g, 0.161 mmol) was dissolved in acetone (15mL) and 10% aq. MeOH (10 mL). Tributyl phosphine (0.261 mL, 0.322 mmol) was. The solution was stirred for 2 hr, concentrated, and the residue was taken up in EtOAc, washed with satd NaHCO$_3$ and dried (MgSO$_4$). Filtration and concentration gave the title compound without further purification.

Step F: Preparation of 1-Triphenylmethyl-4-(hydroxymethyl)-imidazole

To a solution of 4-(hydroxymethyl)imidazole hydrochloride (35.0 g, 260 mmol) in dry DMF (250 ml) at ambient temperature was added Et$_3$N (90.6 mL, 650 mmol). A white solid precipitated from the solution. Chlorotriphenylmethane (76.1 g, 273 mmol) in of DMF (500 mL) was added dropwise. The reaction mixture was stirred for 20 hrs, poured over ice, filtered, and washed with ice water. The resulting product was slurried with cold dioxane, filtered, and dried in vacuo to provide the title compound as a white solid which was sufficiently pure for use in the next step.

Step G: Preparation of 1-Triphenylmethyl-4-(acetoxymethyl)-imidazole

1-Triphenylmethyl-4-(hydroxymethyl)-imidazole (260 mmol) was suspended in pyridine (500 mL). Acetic anhydride (74 mL, 780 mmol) was added dropwise, and the reaction was stirred for 48 hr during which it became homogeneous. The solution was poured into EtOAc, washed sequentially with water, 5% aqueous HCl solution, satd aqueous NaHCO$_3$, solution, and brine. The organic extracts were dried (Na$_2$SO$_4$), and concentrated in vacuo to provide the product as a white powder, which was sufficiently pure for use in the next reaction.

Step H: Preparation of 1-(4-Cyanobenzyl)-5-(acetoxymethyl)-imidazole hydrobromide 1-Triphenylmethyl-4-(acetoxymethyl)-imidazole (85.8 g, 225 mmol) and 4-cyanobenzyl bromide (50.1 g, 232 mmol) in EtOAc (500 mL) were stirred at 60° C. for 20 hr, during which a pale yellow precipitate formed. The reaction was cooled to room temperature and filtered to provide the solid imidazolium bromide salt. The filtrate was concentrated in vacuo to a volume (200 mL), reheated at 60° C. for 2 hrs, cooled to room temperature, and filtered again. The filtrate was concentrated in vacuo to a volume (100 mL), reheated at 60° C. for another 2 hrs, cooled to room temperature, and concentrated in vacuo to provide a pale yellow solid. All of the solid material was combined, dissolved in methanol (500 mL), and warmed to 60° C. After 2 hrs, the solution was concentrated in vacuo to provide a white solid which was triturated with hexane to remove soluble materials. Removal of residual solvents in vacuo provided the titled product hydrobromide as a white solid which was used in the next step without further purification.

Step I: Preparation of 1-(4-Cyanobenzyl)-5-(hydroxymethyl)-imidazole 1-(4-Cyanobenzyl)-5-(acetoxymethyl)-imidazole hydrobromide (50.4 g, 150 mmol) in 3:1 THF/water (1.5 L) at 0° C. was added lithium hydroxide monohydrate (18.9 g, 450 mmol). After 1 hr, the reaction was concentrated in vacuo, diluted with EtOAc (3 L), and washed with water, sat. aq. NaHCO$_3$ and brine. The solution was then dried (Na$_2$SO$_4$), filtered, and concentrated in vacuo to provide the crude product as a pale yellow fluffy solid which was sufficiently pure for use in the next step without further purification.

Step J: Preparation of 1-(4-Cyanobenzyl)-5-(chloromethyl)-imidazole

A solution of 1-(4-cyanobenzyl)-5-(hydroxymethyl)-imidazole (1.0 g, 4.70 mmol), in thionyl chloride (5 ml), was stirred at 70° C. for 16 hrs. The solvent was evaporated in vacuo and the resulting solid suspended in $CH_2C_{12}$, collected by filtration and dried in vacuo. The material was sufficiently pure to be used without further purification.

$^1H$ NMR $CD_3OD$ d 9.06 (1H, s), 7.83(2H, d, J=8.0 Hz), 7.77(1H, s), 7.55(2H, d, J=8.0 Hz), 5.67(2H, s) and 4.78(2H, s) ppm.

Step K: Preparation of 1-(2,2-Diphenylethyl)-3(S)-[N-(1-(4-cyanobenzyl)-1H-imidazol-5-ylethylthiomethyl]piperidine 1-(2,2-Diphenylethyl)-3(S)-mercaptomethyl-piperidine (0.322 mmol), 1-(4-cyanobenzyl)-5-(chloromethyl)-imidazole (0.117 g, 0.386 mmol), and diisopropylethylamine (0.168 mL, 0.966 mmol) were dissolved in $CH_2Cl_2$ (10 mL) and refluxed overnight. The solution was concentrated and the residue was taken up in EtOAc, washed with sat. $NaHCO_3$, water and brine. The organics were dried ($MgSO_4$), concentrated, chromatographed (0–3% MeOH, $CH_2Cl_2,NH_4OH$), Prep HPLC (100:0–5:95 $H_2O$: $CH_3CN$ w/0.1% TFA), free based, and acidified with 1N HCl solution in ether to yield the title compound. $^1H$ NMR ($CD_3OD$); δ 9.03 (s, 1H), 7.80 (D, 2H, J=8 Hz), 7.65 (s, 1H), 7.50–7.33 (m, 10H), 7.26 (D, 2H, J=8 Hz), 5.64 (s, 2H), 4.68 (t, 1H, J=7 Hz), 3.98–3.88 (m, 2H), 3.72 (s, 2H), 3.59–3.56 (m, 1H), 3.51–3.47 (m, 1H), 2.87–2.83 (m, 1H), 2.64 (t, 1H, J=12 Hz), 2.49–2.42 (m, 1H), 2.35–2.27 (m, 1H), 2.02 (br s, 1H), 1.90–1.77 (m, 3H), 1.19–1.12 (m,1H). FAB MS 507 (M+1)

Anal. calculated for $C_{32}H_{34}N_4S.2.5$ HCl.1.65 $H_2O$: C, 61.24; H, 6.69; N, 8.93; Found C, 61.20; H, 5.93; N, 8.72.

Example 19

Preparation of 1-(2,2-Diphenylethyl)-3(S)-[2-(1-(4-cyanobenzyl)-1H-imidazol-5-yl)ethylsulfonylmethyl]piperidine 1-(2,2-Diphenylethyl)-3(S)-[N-(1-(4-cyanobenzyl)-1H-imidazol-5-ylethylthiomethyl]piperidine (0.050 g, 0.087 mmol) was dissolved in MeOH (1 mL) and $H_2O$ (1 mL), treated with Oxone (0.106 g, 0.173 mmol), and stirred at ambient temperature for 1 hr. The solution was concentrated and the residue was taken up in EtOAc, washed with water and brine. The organics were dried ($MgSO_4$) and chromatographed (RP HPLC Waters Prep Pak, 100:0–5:95 $H_2O:CH_3CN$ w/0.1% TFA) to give the title compound as a TFA salt.

FAB MS 539 (M+1)

Anal. calculated for $C_{32}H_{34}N_4O_2S.3.70$ $CF_3CO_2H.0.90$ $H_2O$: C, 48.44; H, 4.08; N, 5.74; Found C, 48.43; H, 4.06; N, 5.96.

Example 20

Preparation of 1-(2,2-Diphenylethyl)-3(S)-[N-(1-(4-cyanobenzyl)-1H-imidazol-5-ylethyl)-N-methyl-carbamoyl]piperidine Step A: Preparation of 1-(tert-Butyloxycarbonyl)-3(S)-[N-(1-(4-cyanobenzyl)-1H-imidazol-5-ylethyl)-N-methylcarbamoyl]piperidine 1-(tert-Butyloxycarbonyl)-3(S)-[N-(1-(4-cyanobenzyl)-1H-imidazol-5-ylethyl)carbamoyl]piperidine (Example 11, Step D)(0.100 g, 0.228 mmol) was dissolved in dry DMF (5 mL) and cooled in a ice bath. NaH (0.011 g, 0.274 mmol) and $CH_3I$ (0.023 mL, 0.365 mmol) were added, and the mixture was stirred at 0° C. for 1.5 hr. The reaction was quenched with water, extracted with EtOAc, the organics washed with $H_2O$ (3x), dried ($MgSO_4$), and concentrated to give the title compound.

Step B: Preparation of 1-3(S)-[N-(1-(4-cyanobenzyl)-1H-imidazole-5-ethyl)-N-methylcarbamoyl]piperidine The title compound was prepared following the procedure outlined in Example 11, Step E.

Step C: Preparation of 1-(2,2-Diphenylethyl)-3(S)-[N-1-(4-cyanobenzyl)-1H-imidazol-5-ylethyl)-N-methylcarbamoyl]piperidine The title compound was prepared following the procedure outlined in Example 11, Step H. FAB MS (M+1) 532.

Anal. calculated for $C_{34}H_{37}N_5O.2.70$ $CF_3CO_2H.1.60$ $H_2O$: C, 54.50; H, 4.98; N, 8.06; Found C, 54.49; H, 4.97; N, 7.99.

Using the methods described above the following compound was prepared:

1-(3-Bromobenzyl)-3(S)-[N-(1-(4-cyanobenzyl)-1H-imidazol-5-ylethyl)-N-methyl-carbamoyl]piperidine
FAB MS (M+1) 520

Example 21

Preparation of 1-(2,2-Diphenylethyl)-3(S)-[N-(1-(4-cyanobenzyl)-1H-imidazol-5-ylethyl)aminomethyl] piperidine Step A: Preparation of 1-(2,2-Diphenylethyl)-3(S)-piperidine carboxaldehyde 1-(2,2-Diphenylethyl)-3(S)-hydroxymethyl-piperidine (Example 18, Step B)-(2.10 g, 7.10 mmol) and $Et_3N$ (2.97 mL, 21.3 mmol) were dissolved in dry DMSO (40 mL) and cooled in an ice bath. Pyridine $SO_3$ complex (3.39 g, 21.3 mmol) was added slowly, and the solution was stirred for 1 hr while allowing to warm to room temperature. The solution was poured into ice water, extracted with $CH_2CL_2$ (2x), the combined organics washed with satd $NaHCO_3$ solution, $H_2O$, brine, and dried ($MgSO_4$). Filtration and concentration gave the title compound without further purification. Step B: Preparation of 1-(2,2-Diphenylethyl)-3(S)-[N-(1-(cyanobenzyl)-1H-imidazol-5-ylethyl)aminomethyl]-piperidine 1-(2,2-Diphenylethyl)-3(S)-piperidine carboxaldehyde (0.575 g, 1.96 mmol),3-(4-cyanobenzyl) histamine dihydrochloride (0.388 g, 1.30 mmol), and $NaCNBH_3$ (0.123 g, 1.96 mmol) were dissolved in MeOH (15 mL) and stirred at ambient temperature overnight. The solution was concentrated and the residue taken up in EtOAc, washed with sat. $NaHCO_3$ solution, $H_2O$, and brine. The organics were dried, concentrated, and chromatographed (0–4% MeOH/$CH_2Cl_2$/$NH_4OH$) to give the title compound which was isolated as a tris HCl salt. $^1H$ NMR ($CD_3OD$); δ 9.05 (s, 1H), 7.81 (d, 2H, J=8 Hz), 7.68 (s, 1H), 7.54 (d, 2H, J=8 Hz), 7.49–7.25 (m, 10H), 5.67 (s, 2H), 4.76–7.74 (m, 1H), 4.05–3.88 (m, 3H), 3.54–3.47 (m, 1H), 3.33–3.30 (m, 1H), 3.19–3.15 (m, 2H), 3.02–3.00 (m, 2H), 2.92–2.90 (m, 2H), 2.42 (br s, 1H), 1.99–1.91 (m, 2H), 1.82–1.78 (m, 1H), 1.31–1.28 (m, 2H). FAB MS 504 (M+1).

Anal. calculated for $C_{33}H_{37}N_5.3.0$ HCl.0.90 $H_2O$: C, 62.99; H, 6.70; N, 11.13; Found C, 63.04; H, 6.83; N, 11.05.

Example 22

Preparation of 1-(2,2-Diphenylethyl)-3(S)-[N-(1-(4-cyanobenzyl)-1H-imidazol-5-ylethyl)-N-acetyl-aminomethyl]piperidine 1-Diphenylethyl-3(S)-[N-1(4-cyanobenzyl)-1H-imidazol-5-ylethylaminomethyl]piperidine (0.151 g, 0.246 mmol) and $Et_3N$ (0.154 mL, 1.10 mmol) were dissolved in dry $CH_2Cl_2$(15 mL) and cooled in an ice bath. A solution of acetyl chloride (0.026 mL, 0.369 mmol) in $CH_2Cl_2$ (1 mL)

was added and the reaction was stirred for 18 hr while allowing to warm to room temperature. The solution was diluted with EtOAc, washed with sat. NaHCO$_3$ solution, H$_2$O, and brine. The organics were dried (MgSO$_4$) and concentrated to yield the title compound. $^1$H NMR (CDCl$_3$); δ 7.59 (d, 2H, J=8 Hz), 7.52 (s, 1H), 7.49–7.04 (m, 12H), 6.87 (s, 1H), 5.29 (s, 2H), 4.17 (t, 1H, J=7 Hz), 3.32–3.25 (m, 1H), 3.21–3.13 (m, 1H), 3.04–2.96 (m, 4H), 2.68–2.49 (m, 4H), 2.24–2.20 (m, 1H), 1.91–1.73 (m, 6H), 1.56–1.50 (m, 1H), 1.46–1.43 (m, 1H), 0.96–0.92 (m, 1H). FAB MS 546 (M+1).

Anal. calculated for C$_{35}$H$_{39}$N$_5$O.0.70 H$_2$O: C, 75.29; H, 7.29; N, 12.54; Found C, 75.25; H, 7.26; N. 12.06.

Using the methods described in Examples 21 and 22, but substituting the requisite amine in Ex. 21, Step B, and the requisite acylating or alkylating agent in Ex. 22, the following compounds were prepared:

1-(2,2-Diphenylethyl)-3(S)-[N-(1-(4-cyanobenzyl)-2-methyl-1H-imidazol-5-ylethyl)-N-acetyl-aminomethyl] piperidine Anal. calculated for C$_{36}$H$_{41}$N$_5$O.0.35 H$_2$O: C, 76.39; H, 7.43; N, 12.37; Found C, 76.39; H, 7.13; N, 12.32.

FAB MS (M+1) 560

1-(2,2-Diphenylethyl)-3(S)-[N-(1-(4-cyanobenzyl)-1H-imidazol-5-ylethyl)-N-cyclopropylmethyl-aminomethyl] piperidine Anal. calculated for C$_{37}$H$_{43}$N$_5$.3.0 HCl.0.95 H$_2$O.0.60 CH$_2$Cl$_2$: C, 62.41; H, 6.73; N, 9.53; Found C, 62.42; H, 7.02; N, 9.43.

FAB MS (M+1) 558

1-(2,2-Diphenylethyl)-3(S)-[N-(2-methyl-1H-imidazol-4-ylethyl)-N-(4-cyanobenzoyl)aminomethyl]piperidine Anal. calculated for C$_{34}$H$_{37}$N$_5$0.2.95 CF3CO2H.1.00 H$_2$O: C, 54.08; H, 4.77; N, 7.90; Found C, 54.06; H, 4.74; N, 7.91.

FAB MS (M+1) 532

Example 23

Preparation of 1-(2,2-Diphenylethyl)-3(S)-[5-(4-cyanobenzyl)-1H-imidazol-1-ylmethyl]piperidine bistrifluoroacetate Step A: Preparation of 1-Trityl-4-(4-cyanobenzyl)-imidazole To a suspension of activated zinc dust (3.57 g, 54.98 mmol) in THF (50 mL) was added dibromoethane (0.315 mL, 3.60 mmol) and the reaction stirred under argon for 45 minutes, at 20° C. The suspension was cooled to 0° C. and α-bromo-p-toluinitrile (9.33 g, 47.6 mmol) in THF (100 mL) was added dropwise over a period of 10 minutes. The reaction was then allowed to stir at 20° C. for 6 hours and bis(triphenylphosphine)Nickel II chloride (2.40 g, 3.64 mmol) and 5-iodotrityl imidazole (15.95 g, 36.6 mmol) were added in one portion. The resulting mixture was stirred 16 hours at 20° C. and then quenched by addition of saturated NH$_4$Cl solution (100 mL) and the mixture stirred for 2 hours. Saturated aq. NaHCO$_3$ solution was added to give a pH of 8 and the solution was extracted with EtOAc (2×250 mL), dried (MgSO$_4$) and the solvent evaporated in vacuo. The residue was chromatographed (Silica gel, 0–20% EtOAc in CH$_2$Cl$_2$) to afford the title compound as a white solid.

$^1$H NMR (CDCl$_3$, 400 Mz) δ (7.54 (2H, d, J=7.9 Hz), 7.38(1H, s), 7.36–7.29 (11H, m), 7.15–7.09(6H, m), 6.58 (1H, s) and 3.93(2H, s) ppm.

Step B: Preparation of 1-(2,2-Diphenylethyl)-3(S)-[5-(4-cyanobenzyl)-1H-imidazol-1-ylmethyl]piperidine bis trifluoroacetate bistrifluoroacetate To a solution of 1-(2,2-Diphenylethyl)-3(S)-hydroxymethylpiperdine (Example 18, Step B) (0.271 g, 0.917 mmol) and 1-trityl-4-(4-cyanobenzyl)imidazole (0.390 g, 0.917 mmol) in CH$_2$Cl$_2$ (7 mL) was added diisopropylethylamine (0.639 mL, 3.67 mmol) under N$_2$. The mixture was cooled to −78° C. and trifluoromethanesulfonic anhydride (0.154 mL, 0.917 mmol) was added dropwise via syringe. The cooling bath was removed and the reaction was stirred at 25° C. for 18 hr. The reaction was evaporated in vacuo and the residue was dissolved in methanol (20 mL) and heated to reflux for 1 hr. After cooling the mixture was evaporated in vacuo and the residue was partitioned with EtOAc (50 mL) and satd NaHCO$_3$ (30 mL), the organic layer separated, washed with brine (30 mL) and dried (MgSO$_4$). Filtration and evaporation in vacuo gave the title compound which was purified by chromatography on silica gel using CH$_2$Cl$_2$:MeOH, 98:2, followed by preparative HPLC on a Waters C-18 Delta-pak column.

Anal. calculated for C$_{31}$H$_{32}$N$_4$.3.10 CF3CO2H.0.75 H$_2$O: C, 53.98; H, 4.46; N, 6.77; Found C, 54.02; H, 4.47; N, 6.75.

Example 24

Preparation of 1-(2,2-Diphenylethyl)-3(S)-[5-(4-cyanobenzyl)-1H-imidazol-1-ylethylcarbamoyl] piperdine Step A: Preparation of 5-(4-cyanobenzyl)-1H-imidazol-1-ylethylphthalimide 2-Hydroxyethylphthalimide (3.23 g, 16.9 mmol) was dissolved in CH$_2$Cl$_2$ (50 ml) and Et$_3$N(3.92 mL, 28.2 mmol) under N$_2$. The reaction was cooled to −78° C. and trifluoromethanesulfonic anhydride (2.85 ml, 16.9 mmol) was added dropwise via syringe. After stirring for 0.5 hr at 0° C. the reaction was cooled to −20° C. and 1-trityl-4-(4-cyanobenzyl)imidazole (2.4 g, 5.64 mmol) in CH$_2$Cl$_2$ (20 mL) was added to the mixture which was stirred at 25° C. for 18 hr. The reaction was concentrated in vacuo to dryness, and the residue was dissolved in MeOH (75mL) and heated to reflux for 2 hr. After cooling and evaporation in vacuo the residue was partitioned with EtOAc (100 mL) and satd NaHCO$_3$ (30 mL). The organic layer was washed with brine (30 mL) and dried (MgSO$_4$). Evaporation in vacuo gave the title compound after chromatography on silica gel eluting with CH$_2$Cl$_2$:MeOH:NH$_4$OH 95:5:0.5 (3 L), 90:10:1.0 (2 L), 85:15:1.5 (3 L).

Step B: Preparation of 5-(4-cyanobenzyl)-1-(2-aminoethyl)-1H-imidazole

To a solution of 5-(4-cyanobenzyl)-1H-imidazol-1-ylethylphthalimide (3.2 g, 9.2 mmol) in absolute EtOH (75 mL) was added hydrazine (0.72 mL, 23.0 mmol), and the mixture was refluxed for 18 hr. Dimethyl phthalate (7.59 mL, 46 mmol) was added to the mixture and refluxing was continued for 4 hr. The reaction was cooled in a freezer for 18 hr. The solids that formed were filtered and washed with water. Evaporation in vacuo afforded the title compound after chromatography on silica gel eluting with CH$_2$Cl$_2$:MeOH:NH$_4$OH 95:5:0.5 (2 L), 90:10:1.0 (2 L), 85:15:1.5 (2 L).

Step C: Preparation of 1-(2,2-Diphenylethyl)-3(S)-[5-(4-cyanobenzyl)-1H-imidazol-1-ylethylecarbamoyl]piperdine Following the procedure outlined in Example 10, Step B using 1-(2,2-Diphenylethyl)-3(S)-carboxy piperidine and the amine from Step B above, the title compound was prepared.

Anal. calculated for C$_{33}$H$_{35}$N$_5$O.0.60 H$_2$O: C, 74.99; H, 6.90; N, 13.25; Found C, 74.99; H, 6.98; N, 13.19.

Example 25

In vitro inhibition of ras farnesyl transferase

Assays of farnesyl-protein transferase. Partially purified a bovine FPTase and Ras peptides (Ras-CVLS, Ras-CVIM and Ras-CAIL) were prepared as described by Schaber et al., *J. Biol. Chem.* 265:14701–14704 (1990), Pompliano, et al., *Biochemistry* 31:3800 (1992) and Gibbs et al.. *PNAS U.S.A.* 86:6630–6634 (1989), respectively. Bovine FPTase was assayed in a volume of 100 μl containing 100 mM N-(2-hydroxy ethyl) piperazine—N'-(2-ethane sulfonic acid) (HEPES), pH 7.4, 5 mM MgCl$_2$, 5 mM dithiothreitol (DTT), 100 mM [$^3$H]-farnesyl diphosphate ([3H]-FPP; 740 CBq/mmol, New England Nuclear), 650 nM Ras-CVLS and 10 μg/ml FPTase at 31° C. for 60 min. Reactions were initiated with FPTase and stopped with 1 ml of 1.0 M HCL in ethanol. Precipitates were collected onto filter-mats using a TomTec Mach II cell harvester, washed with 100% ethanol, dried and counted in an LKB β-plate counter. The assay was linear with respect to both substrates, FPTase levels and time; less than 10% of the [3H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 μM ZnCl$_2$ and 100 nM Ras-CVIM were added to the reaction mixture. Reactions were performed for 30 min., stopped with 100 μl of 30% (v/v) trichloroacetic acid (TCA) in ethanol and processed as described above for the bovine enzyme.

The compounds of the instant invention that are described in Example 1–24 were tested for inhibitory activity against human FPTase by the assay described above and were found to have IC$_{50}$ of <10 μM.

Example 26

In vivo ras farnesylation assay

The cell line used in this assay is a v-ras line derived from either Rat1 or NIH$_3$T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

Example 27

In vivo growth inhibition assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of 1×10$^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

What is claimed is:

1. A compound which inhibits farnesyl-protein transferase of the formula A:

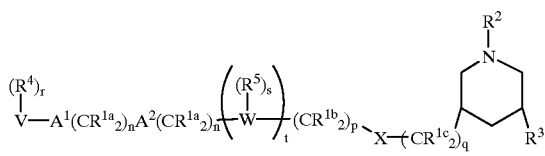

A wherein:

$R^{1a}$, $R^{1b}$ and $R^{1c}$ are independently selected from:

a) hydrogen, b) unsubstituted or substituted aryl, $C_3$–$C_{10}$ cycloalkyl, F, $C_2$–$C_6$ alkenyl, $C_2$–$C_6$ alkynyl, $R^8O$—, $R^9S(O)_m$—, $R^8C(O)NR^8$—, CN, NO$_2$, $(R^8)_2N$—C(NR$^8$)—, $R^8C(O)$—, $R^8OC(O)$—, N$_3$, —N(R$^8$)$_2$, or $R^9OC(O)NR^8$—, c) $C_1$–$C_6$ alkyl unsubstituted or substituted by unsubstituted or substituted aryl, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $(R^8)_2N$—C(NR$^8$)—, $R^8C(O)$—, $R^8OC(O)$—, N$_3$, —N(R$^8$)$_2$, or $R^9OC(O)$—NR$^8$—;

$R^2$ is selected from: H; unsubstituted or substituted $C_{1-8}$ alkyl, unsubstituted or substituted $C_{2-8}$ alkenyl, unsubstituted or substituted aryl, unsubstituted or substituted morpholinyl,

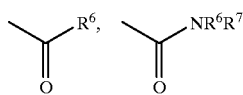 and —S(O)₂R⁶, wherein the substituted group is substituted with one or more of:

1) aryl or morpholinyl, unsubstituted or substituted with one or two groups selected from:
   a) $C_{1-4}$ alkyl,
   b) $(CH_2)_pOR^6$,
   c) $(CH_2)_pNR^6R^7$,
   d) halogen,
   e) $C_{1-4}$ perfluoroalkyl,
2) $C_{3-6}$ cycloalkyl,
3) $OR^6$,
4) $SR^6$, $S(O)R^6$, $SO_2R^6$,
5) —NR⁶R⁷,
6) 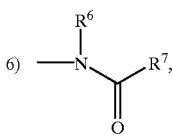
7) 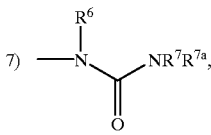
8) 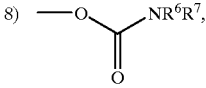
9) 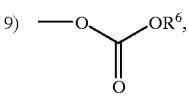
10) 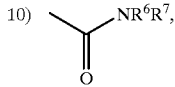
11) —SO₂—NR⁶R⁷,
12) 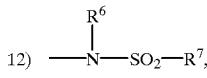
13) 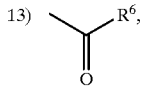
14) 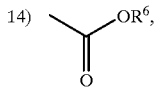
15) $C_{1-8}$ alkyl, or
16) $C_{1-8}$ perfluoroalkyl, provided R² comprises a morpholinyl group if R³ does not comprise a morpholinyl group;

R³ is selected from: H,

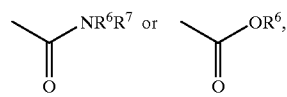

provided R³ comprises a morpholinyl group if R² does not comprise a morpholinyl group;

R⁴ is independently selected from:
a) hydrogen,
b) unsubstituted or substituted aryl, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, NO₂, $R^8_2N$—$C(NR^8)$—, $R^8C(O)$—, $R^8OC(O)$—, N₃, —$N(R^8)_2$, or $R^9OC(O)NR^8$—, and
c) $C_1$–$C_6$ alkyl unsubstituted or substituted by aryl, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NH$—, CN, $H_2N$—$C(NH)$—, $R^8C(O)$—, $R^8OC(O)$—, N₃, —$N(R^8)_2$, or $R^8OC(O)NH$—;

R⁵ is independently selected from:
a) hydrogen,
b) $C_2$–$C_6$ alkenyl, $C_2$–$C_6$ alkynyl, $C_3$–$C_6$ cycloalkyl, perfluoroalkyl, F, Cl, Br, $R^8O$—, $R^9S(O)_m$—, $R^8C(O)NR^8$—, CN, NO₂, $(R^8)_2N$—C-$(NR^8)$—, $R^8C(O)$—, $R^8OC(O)$—, N₃, —$N(R^8)_2$, or $R^9OC(O)NR^8$—, and
c) $C_1$–$C_6$ alkyl, unsubstituted or substituted by perfluoroalkyl, F, Cl, Br, $R^8O$—, $R^9S(O)_m$—, $R^8C(O)NR^8$—, CN, $(R^8)_2N$—$C(NR^8)$—, $R^8C(O)$—, $R^8OC(O)$—, N₃, —$N(R^8)_2$, or $R^9OC(O)NR^8$—;

R⁶, R⁷ and $R^{7a}$ are independently selected from: H; $C_{1-4}$ alkyl, $C_{3-6}$ cycloalkyl, morpholinyl, aryl, $C_{1-4}$ perfluoroalkyl, unsubstituted or substituted with one or two substituents selected from:
a) $C_{1-4}$ alkoxy,
b) substituted or unsubstituted aryl or substituted or unsubstituted morpholinyl,
c) halogen,
d) HO,
e) 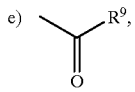
f) 
g) —$S(O)_mR^9$, or
h) $N(R^8)_2$; or R⁶ and R⁷ may be joined in a ring to form a carbocycle or a morpholine;

R⁷ and $R^{7a}$ may be joined in a ring to form a carbocycle or a morpholine;

R⁸ is independently selected from hydrogen, $C_1$–$C_6$ alkyl, benzyl, 2,2,2-trifluoroethyl and aryl;

R⁹ is independently selected from $C_1$–$C_6$ alkyl and aryl;

R¹⁰ is selected from: H; $R^8C(O)$—; $R^9S(O)_m$—; unsubstituted or substituted $C_{1-4}$ alkyl, unsubstituted or substituted $C_{3-6}$ cycloalkyl, unsubstituted or substituted aryl, substituted aroyl, substituted arylsulfonyl, wherein the substituted group is substituted with one or two substituents selected from:

a) $C_{1-4}$ alkoxy,
b) aryl,
c) halogen,
d) HO, e) 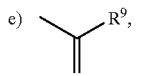

f) 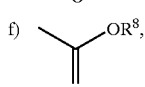

g) 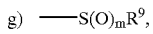

h) $N(R^8)_2$, or
i) $C_{3-6}$ cycloalkyl;

$A^1$ is selected from: a bond, —CH=CH—, —C≡C—, —C(O)—, —C(O)NR$^8$—, O, —N(R$^8$)—, and S(O)$_m$;
$A^2$ is selected from: a bond, —CH=CH—, —C≡C—, —C(O)—, —C(O)NR$^8$—, —NR$^8$C(O)—, O, —N(R$^8$), —S(O)$_2$N(R$^8$)—, —N(R$^8$)S(O)$_2$—, and S(O)$_m$;
V is aryl;
W is a imidazolyl;
X is a bond, —C(=O)NR$^{10}$, —NR$^{10}$C(=O)—, —S(O)$_m$—, or —NR$^{10}$—;

| | |
|---|---|
| m is | 0, 1 or 2; |
| n is | 0 or 1; |
| p is | 0, 1, 2, 3 or 4; |
| q is | 0, 1, 2, 3 or 4; |
| r is | 0 to 5, |
| s is | 1 or 2; and |
| t is | 1; | or an optical isomer or pharmaceutically acceptable salt thereof.

2. The compound according to claim 1, which inhibits farnesyl-protein transferase, of the formula A:

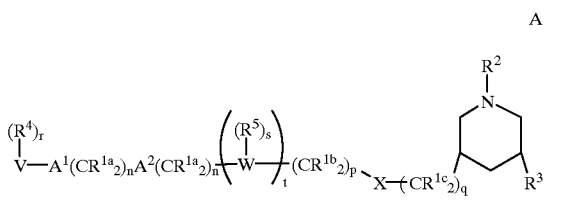

wherein:

$R^{1a}$ and $R^{1c}$ are independently selected from: hydrogen, $C_3$–$C_{10}$ cycloalkyl, $R^8$O—, —N(R$^8$)$_2$, F or $C_1$–$C_6$ alkyl;
$R^{1b}$ is independently selected from:
a) hydrogen,
b) unsubstituted or substituted aryl, $C_3$–$C_6$ cycloalkyl, $R^8$O—, —N(R$^8$)$_2$ or $C_2$–$C_6$ alkenyl,
c) $C_1$–$C_6$ alkyl unsubstituted or substituted by unsubstituted or substituted aryl, $C_3$–$C_6$ cycloalkyl, $C_2$–$C_6$ alkenyl, $R^8$O—, or —N(R$^8$)$_2$;
$R^2$ is selected from:
a) $C_{1-8}$ alkyl, unsubstituted or substituted with one or more of:

1) aryl or morpholinyl, unsubstituted or substituted with:
 i) $C_{1-4}$ alkyl,
 ii) (CH$_2$)$_p$OR$^6$,
 iii) (CH$_2$)$_p$NR$^6$R$^7$,
 iv) halogen,
 v) $C_{1-4}$ perfluoroalkyl,
2) OR$^6$,
3) SR$^6$, SO$_2$R$^6$, or 4) 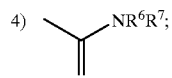

b) 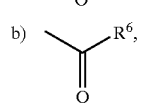

c) aryl, substituted or substituted with one or more of:
1) $C_{1-8}$ alkyl,
2) $C_{1-8}$ perfluoroalkyl,
3) OR$^6$,
4) SR$^6$, SO$_2$R$^6$, or 5) 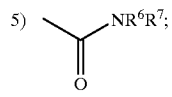

d) —SO$_2$R$^6$,
provided R$^2$ comprises a morpholinyl group if R$^3$ does not comprise a morpholinyl group;

R$^3$ is selected from H;

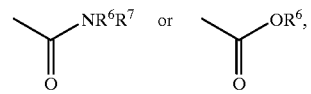

provided R$^3$ comprises a morpholinyl group if R$^3$ does not comprise a morpholinyl group;

R$^4$ is independently selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, R$^8$O—, R$^8$C(O)NR$^8$—, CN, NO$_2$, (R$^8$)$_2$N—C(NR$^8$)—, R$^8$C(O)—, R$^8$OC(O)—, —N(R$^8$)$_2$, or R$^9$OC(O)NR$^8$—, and
c) $C_1$–$C_6$ alkyl substituted by $C_1$–$C_6$ perfluoroalkyl, R$^8$O—, R$^8$C(O)NR$^8$—, (R$^8$)$_2$N—C(NR$^8$)—, R$^8$C(O)—, R$^8$OC(O)—, —N(R$^8$)$_2$, or R$^9$OC(O)NR$^8$—;

R$^5$ is selected from:
a) hydrogen,
b) $C_2$–$C_6$ alkenyl, $C_2$–$C_6$ alkynyl, $C_3$–$C_6$ cycloalkyl, $C_1$–$C_6$ perfluoroalkyl, F, Cl, R$^8$O—, R$^9$S(O)$_m$—, R$^8$C(O)NR$^8$—, CN, NO$_2$, (R$^8$)$_2$N—C(NR$^8$)—, R$^8$C(O)—, R$^8$OC(O)—, —N(R$^8$)$_2$, or R$^9$OC(O)NR$^8$—, and
c) $C_1$–$C_6$ alkyl unsubstituted or substituted by $C_1$–$C_6$ perfluoroalkyl, F, Cl, R$^8$O—, R$^9$S(O)$_m$—, R$^8$C(O)NR$^8$—, CN, (R$^8$)$_2$N—C(NR$^8$)—, R$^8$C(O)—, R$^8$OC(O)—, —N(R$^8$)$_2$, or R$^9$OC(O)NR$^8$—;

R$^6$, R$^7$ and R$^{7a}$ are independently selected from: H, $C_{1-4}$ alkyl, $C_{3-6}$ cycloalkyl, aryl, morpholinyl, unsubstituted or substituted with:

a) $C_{1-4}$ alkoxy, b) halogen, or c) substituted or unsubstituted aryl or substituted or unsubstituted morpholinyl;

$R^6$ and $R^7$ may be joined in a ring to form a carbocycle or a morpholine;

$R^7$ and $R^{7a}$ may be joined in a ring to form a carbocycle or a morpholine;

$R^8$ is independently selected from hydrogen, $C_1$–$C_6$ alkyl, benzyl, 2,2,2-trifluoroethyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1-4}$ alkyl, unsubstituted or substituted $C_{3-6}$ cycloalkyl, unsubstituted or substituted aryl, substituted aroyl, substituted arylsulfonyl, wherein the substituted group is substituted with one or two substituents selected from:

a) $C_{1-4}$ alkoxy, b) aryl, c) halogen, d) HO, e) 

f) 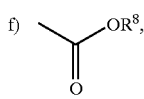

g) 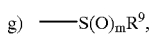

h) $N(R^8)_2$, or i) $C_{3-6}$ cycloalkyl;

$A^1$ and $A^2$ are independently selected from: a bond, —CH=CH—, —C≡C—, —C(O)—, —C(O)NR$^8$—, O, —N(R$^8$)—, or S(O)$_m$;

V is aryl;

W is imidazolyl;

X is a bond, —C(=O)NR$^{10}$—, NR$^{10}$C(=O)—, —S(O)$_m$— or —NR$^{10}$—;

| | |
|---|---|
| m is | 0, 1 or 2; |
| n is | 0 or 1; |
| p is | 1, 2 or 3; |
| q is | 0 or 1; |
| r is | 0 or 5; |
| s is | 1 or 2; and |
| t is | 1; | or an optical isomer or pharmaceutically acceptable salt thereof.

3. The compound according to claim 1, which inhibits farnesyl-protein transferase, of the formula B:

wherein:

$R^{1a}$ and $R^{1c}$ are independently selected from: hydrogen, $C_3$–$C_{10}$ cycloalkyl, $R^8O$—, —$N(R^8)_2$, F or $C_1$–$C_6$ alkyl;

$R^{1b}$ is independently selected from:

a) hydrogen, b) aryl, $C_3$–$C_{10}$ cycloalkyl, $R^8O$—, —$N(R^8)_2$, F or $C_2$–$C_6$ alkenyl, c) unsubstituted or substituted $C_1$–$C_6$ alkyl wherein the substituent on the substituted $C_1$–$C_6$ alkyl is selected from unsubstituted or substituted aryl, $C_3$–$C_{10}$ cycloalkyl, $C_2$–$C_6$ alkenyl, $R^8O$— and —$N(R^8)_2$;

$R^2$ is selected from: H; unsubstituted or substituted $C_{1-8}$ alkyl, unsubstituted or substituted $C_{2-8}$ alkenyl, unsubstituted or substituted aryl, unsubstituted or substituted morpholinyl,

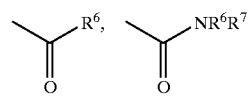

and —$S(O)_2R^6$, wherein the substituted group is substituted with one or more of:

1) aryl or morpholinyl, unsubstituted or substituted with one or two groups selected from:
   a) $C_{1-4}$ alkyl,
   b) $(CH_2)_pOR^6$,
   c) $(CH_2)_pNR^6R^7$,
   d) halogen,
   e) $C_{1-4}$ perfluoroalkyl, 2) $C_{3-6}$ cycloalkyl,

3) $OR^6$,

4) $SR^6$, $S(O)R^6$, $SO_2R^6$,

5) 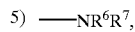

6) 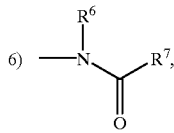

7) 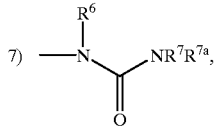

8) 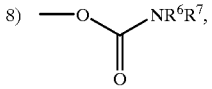

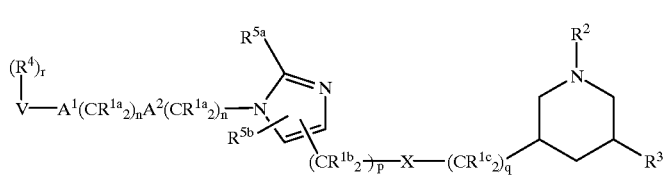

B

-continued

9) 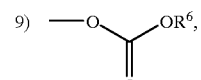

10) 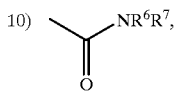

11) —SO₂—NR⁶R⁷,

12) 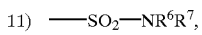

13) 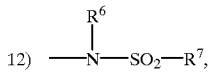

14) 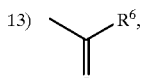

15) $C_{1-8}$ alkyl, or
16) $C_{1-8}$ perfluoroalkyl,
provided $R^2$ comprises a morpholinyl group if $R^3$ does not comprise a morpholinyl group;
$R^3$ is selected from: H;

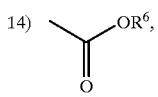

provided $R^3$ comprises a morpholinyl group if $R^2$ does not comprise a morpholinyl group;
$R^4$ is independently selected from:
  a) hydrogen,
  b) aryl, substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, —$N(R^8)_2$, or $R^9OC(O)NR^8$—, and
  c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, —$N(R^8)_2$, or $R^9OC(O)NR^8$—;
$R^{5a}$ and $R^{5b}$ are independently hydrogen, $C_1$–$C_6$ alkyl, cyclopropyl, trifluoromethyl and halogen;
$R^6$, $R^7$ and $R^{7a}$ are independently selected from: H; $C_{14}$ alkyl, $C_{3-6}$ cycloalkyl, aryl, morpholinyl, unsubstituted or substituted with:
  a) $C_{1-4}$ alkoxy,
  b) halogen, or
  c) substituted or unsubstituted aryl or substituted or unsubstituted morpholinyl;
$R^6$ and $R^7$ may be joined in a ring to form a carbocycle or a morpholine;
$R^7$ and $R^{7a}$ may be joined in a ring to form a carbocycle or a morpholine;

$R^8$ is independently selected from hydrogen, $C_1$–$C_6$ alkyl, 2,2,2-trifluoroethyl, benzyl and aryl;
$R^9$ is independently selected from $C_1$–$C_6$ alkyl and aryl;
$R^{10}$ is selected from: H; $R^8C(O)$—; $R^9S(O)_m$—; unsubstituted or substituted $C_{1-4}$ alkyl, unsubstituted or substituted $C_{3-6}$ cycloalkyl, or substituted heteroaroyl, substituted arylsulfonyl, wherein the substituted group is substituted with one or two substituents selected from:
  a) $C_{1-4}$ alkoxy,
  b) aryl,
  c) halogen,
  d) HO,
  e) 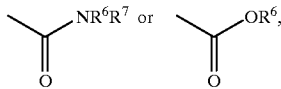
  f) (same structure with $OR^8$)
  g) —$S(O)_mR^9$,
  h) $N(R^8)_2$, or
  i) $C_{3-6}$ cycloalkyl;
$A^1$ and $A^2$ are independently selected from: a bond, —CH=CH—, —C≡C—, —C(O)—, —C(O)NR⁸—, O, —N(R⁸)—, or $S(O)_m$;
V is aryl;
X is a bond, —C(=O)NR¹⁰—, —NR¹⁰C(=O)—, —S(O)ₘ— or —NR¹⁰—;

| | |
|---|---|
| m is | 0, 1 or 2; |
| n is | 0 or 1; |
| p is | 0, 1, 2, 3 or 4; |
| q is | 0 or 1; and |
| r is | 0 to 5; | or an optical isomer or pharmaceutically acceptable salt thereof.

4. The compound according to claim 1, which inhibits farnesyl-protein transferase, of the formula C:

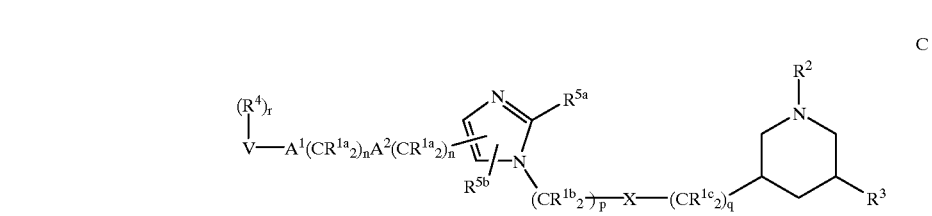

wherein:
$R^{1a}$ and $R^{1c}$ are independently selected from: hydrogen, $C_3$–$C_{10}$ cycloalkyl, $R^8O$—, —$N(R^8)_2$, F or $C_1$–$C_6$ alkyl;
$R^{1b}$ is independently selected from:
  a) hydrogen,
  b) aryl, $C_3$–$C_{10}$ cycloalkyl, $R^8O$—, —$N(R^8)_2$, F or $C_2$–$C_6$ alkenyl,
  c) unsubstituted or substituted $C_1$–$C_6$ alkyl wherein the substituent on the substituted $C_1$–$C_6$ alkyl is selected from unsubstituted or substituted aryl, $C_3$–$C_{10}$ cycloalkyl, $C_2$–$C_6$ alkenyl, $R^8O$— and —$N(R^8)_2$;

$R^2$ is selected from: H; unsubstituted or substituted $C1$-$8$ alkyl, unsubstituted or substituted $C_{2-8}$ alkenyl, unsubstituted or substituted aryl, unsubstituted or substituted morpholinyl,

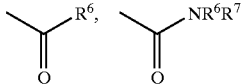

and —$S(O)_2R^6$, wherein the substituted group is substituted with one or more of:

1) aryl or morpholinyl, unsubstituted or substituted with one or two groups selected from:
   a) $C_{1-4}$ alkyl,
   b) $(CH_2)_pOR^6$,
   c) $(CH_2)_pNR^6R^7$,
   d) halogen,
   e) $C_{1-4}$perfluoroalkyl,
2) $C_{3-6}$ cycloalkyl,
3) $OR^6$,
4) $SR^6$, $S(O)R^6$, $SO_2R^6$,

5) —$NR^6R^7$,

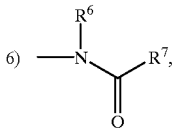

6)

7)

8)

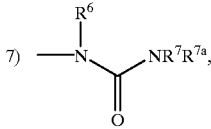

9)

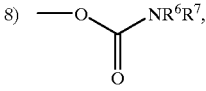

10)

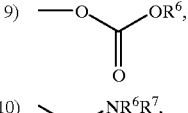

11) —$SO_2$—$NR^6R^7$,

12)

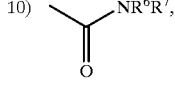

13)

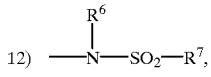

14)

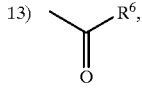

15) $C_{1-8}$ alkyl, or
16) $C_{1-8}$ perfluoroalkyl, provided $R^2$ comprises a morpholinyl group if $R^3$ does not comprise a morpholinyl group;

$R^3$ is selected from: H;

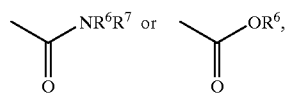

provided $R^3$ comprises a morpholinyl group if $R^2$ does not comprise a morpholinyl group;

$R^4$ is independently selected from:
a) hydrogen,
b) aryl, substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, —$N(R^8)_2$, or $R^9OC(O)NR^8$—, and
c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, —$N(R^8)_2$, or $R^9OC(O)NR^8$—;

$R^{5a}$ and $R^{5b}$ are independently hydrogen, $C_1$–$C_6$ alkyl, cyclopropyl, trifluoromethyl and halogen;

$R^6$, $R^7$ and $R^{7a}$ are independently selected from: H; $C_{1-4}$ alkyl, $C_{3-6}$ cycloalkyl, aryl, morpholinyl, unsubstituted or substituted with:
a) $C_{1-4}$ alkoxy,
b) halogen, or
c) substituted or unsubstituted aryl or substituted or unsubstituted morpholinyl;

$R^6$ and $R^7$ may be joined in a ring to form a carbocycle or a morpholine;

$R^7$ and $R^{7a}$ may be joined in a ring to form a carbocycle or a morpholine;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1-4}$ alkyl, unsubstituted or substituted $C_{3-6}$ cycloalkyl, unsubstituted or substituted aryl, substituted aroyl, substituted arylsulfonyl, wherein the substituted group is substituted with one or two substituents selected from:
a) $C_{1-4}$ alkoxy,
b) aryl,
c) halogen,
d) HO, e) 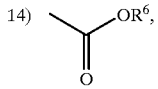

f)

g) —$S(O)_mR^9$, h) $N(R^8)_2$, or
i) $C_{3-6}$ cycloalkyl;

$A^1$ and $A^2$ are independently selected from: a bond, —CH=CH—, —C≡C—, —C(O)—, —C(O)$NR^8$—, O, —$N(R^8)$—, or $S(O)_m$;

V is aryl;

X is a bond, —C(=O)$NR^{10}$—, —$NR^{10}$C(=O)—, —$S(O)_m$— or —$NR^{10}$—;

| | |
|---|---|
| m is | 0, 1 or 2; |
| n is | 0 or 1; |
| p is | 0, 1, 2, 3 or 4, provided that p is not 0 if X is a bond or —NR$^{10}$—. |
| q is | 0 or 1; and |
| r is | 0 to 5; | or an optical isomer or pharmaceutically acceptable salt thereof.

5. The compound according to claim 3, which inhibits farnesyl-protein transferase, of the formula D:

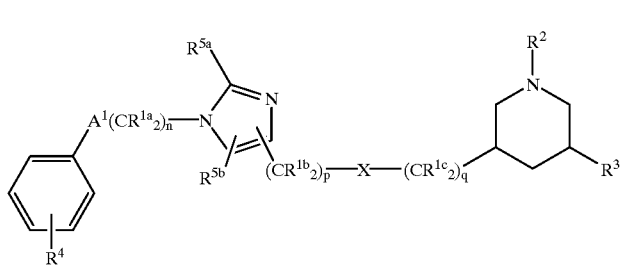

wherein:

R$^{1a}$ and R$^{1c}$ are independently selected from: hydrogen, C$_3$–C$_{10}$ cycloalkyl or C$_1$–C$_6$ alkyl;

R$^{1b}$ is independently selected from:
 a) hydrogen,
 b) aryl, C$_3$–C$_{10}$ cycloalkyl, R$^8$O—, —N(R$^8$)$_2$, F or C$_2$–C$_6$ alkenyl,
 c) C$_1$–C$_6$ alkyl unsubstituted or substituted by aryl, C$_3$–C$_{10}$ cycloalkyl, C$_2$–C$_6$ alkenyl, R$^8$O—, or —N(R$^8$)$_2$;

R$^2$ is selected from: H; unsubstituted or substituted C$_{1-8}$ alkyl, unsubstituted or substituted aryl,

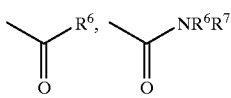

and —S(O)$_2$R$^6$, wherein the substituted group is substituted with one or more of:

1) aryl or morpholinyl, unsubstituted or substituted with one or two groups selected from:
 a) C$_{1-4}$ alkyl,
 b) (CH$_2$)$_p$OR$^6$,
 c) (CH$_2$)$_p$NR$^6$R$^7$,
 d) halogen,
 e) C$_{1-4}$ perfluoroalkyl,
2) C$_{3-6}$ cycloalkyl,
3) OR$^6$,
4) SR$^6$, S(O)R$^6$, SO$_2$R$^6$,

5) —NR$^6$R$^7$,

6) 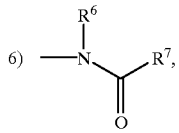

7) 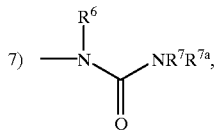

8) 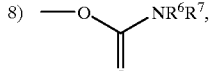

9) 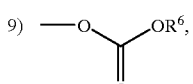

10) 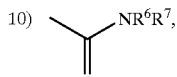

11) —SO$_2$—NR$^6$R$^7$,

12) 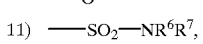

13) 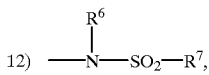

14) 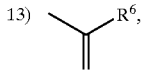

15) C$_{1-8}$ alkyl, or
16) C$_{1-8}$ perfluoroalkyl, provided R$^2$ comprises a morpholinyl group if R$^3$ does not comprise a morpholinyl group;

R$^3$ is selected from: H;

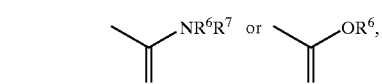

provided R$^3$ comprises a morpholinyl group if R$^2$ does not comprise a morpholinyl group;

$R^4$ is independently selected from:
a) hydrogen,
b) aryl, substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, —$N(R^8)_2$, or $R^9OC(O)NR^8$—, and
c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, —$N(R^8)_2$, or $R^9OC(O)NR^8$—;

$R^{5a}$ and $R^{5b}$ are independently hydrogen, ethyl, cyclopropyl or methyl;

$R^6$, $R^7$ and $R^{7a}$ are independently selected from: H; $C_{1-4}$ alkyl, $C_{3-6}$ cycloalkyl, aryl, morpholinyl, unsubstituted or substituted with:
a) $C_{1-4}$ alkoxy,
b) halogen, or
c) substituted or unsubstituted aryl or substituted or unsubstituted morpholinyl;

$R^6$ and $R^7$ may be joined in a ring to form a carbocycle or a morpholine;

$R^7$ and $R^{7a}$ may be joined in a ring to form a carbocycle or a morpholine;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1-4}$ alkyl, wherein the substituted alkyl group is substituted with one or two substituents selected from:
a) $C_{1-4}$ alkoxy,
b) aryl,
c) halogen,
d) HO, e) 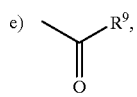

f) 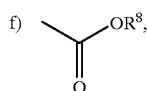

g) 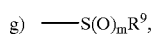

h) $N(R^8)_2$, or
i) $C_{3-6}$ cycloalkyl;

$A^1$ is selected from: a bond, —C(O)—, O, —$N(R^8)$—, or $S(O)_m$;

X is a bond, —C(=O)$NR^{10}$—, —$NR^{10}$C(=O)—, —$S(O)_m$— or —$NR^{10}$—;

n is 0 or 1; provided that n is not 0 if $A^1$ is a bond, O, —$N(R^8)$—, or $S(O)_m$;
m is 0, 1 or 2;
p is 0, 1, 2, 3 or 4; and
q is 0 or 1;

or an optical isomer or pharmaceutically acceptable salt thereof.

6. The compound according to claim 4, which inhibits farnesyl-protein transferase, of the formula E:

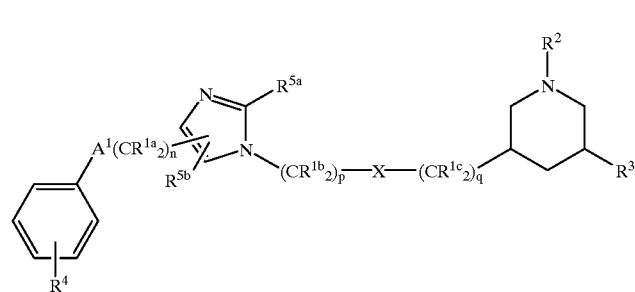

E wherein:

$R^{1a}$ and $R^{1c}$ are independently selected from: hydrogen, $R^8O$—, —$N(R^8)_2$, F, $C_3$–$C_{10}$ cycloalkyl or $C_1$–$C_6$ alkyl;

$R^{1b}$ is independently selected from:
a) hydrogen,
b) aryl, $C_3$–$C_{10}$ cycloalkyl, $R^8O$—, —$N(R^8)_2$, F or $C_2$–$C_6$ alkenyl,
c) $C_1$–$C_6$ alkyl unsubstituted or substituted by aryl, $C_3$–$C_{10}$ cycloalkyl, $C_2$–$C_6$ alkenyl, $R^8O$—, or —$N(R^8)_2$;

$R^2$ is selected from: H; unsubstituted or substituted $C_{1-8}$ alkyl, unsubstituted or substituted aryl,

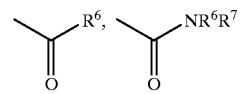

and —$S(O)_2R^6$, wherein the substituted group is substituted with one or more of:

1) aryl or morpholinyl, unsubstituted or substituted with one or two groups selected from:
a) $C_{1-4}$ alkyl,
b) $(CH_2)_pOR^6$,
c) $(CH_2)_pNR^6R^7$,
d) halogen,
e) $C_{1-4}$ perfluoroalkyl,
2) $C_{3-6}$ cycloalkyl,
3) $OR^6$,

4) $SR^6$, $S(O)R^6$, $SO_2R^6$,

5) —$NR^6R^7$,

6) 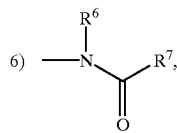

7) 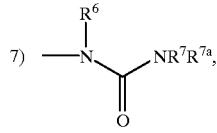

8) 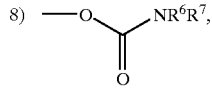

9) 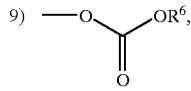

10) 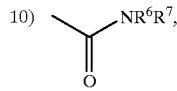

11) —$SO_2$—$NR^6R^7$,

12) 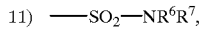

13) 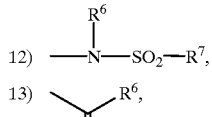

14) 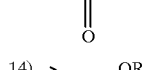

15) $C_{1-8}$ alkyl, or
16) $C_{1-8}$ perfluoroalkyl,
provided $R^2$ comprises a morpholinyl group if $R^3$ does not comprise a morpholinyl group;
$R^3$ is selected from: H;

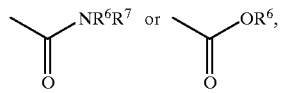

provided $R^3$ comprises a morpholinyl group if $R^2$ does not comprise a morpholinyl group;
$R^4$ is independently selected from:
a) hydrogen,
b) aryl, substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, —$N(R^8)_2$, or $R^9OC(O)NR^8$—, and
c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, —$N(R^8)_2$, or $R^9OC(O)NR^8$—;
$R^{5a}$ and $R^{5b}$ are independently hydrogen, ethyl, cyclopropyl or methyl;
$R^6$, $R^7$ and $R^{7a}$ are independently selected from: H; $C_{1-4}$ alkyl, $C_{3-6}$ cycloalkyl, aryl, morpholinyl, unsubstituted or substituted with:

a) $C_{1-4}$ alkoxy,
b) halogen, or
c) substituted or unsubstituted aryl or substituted or unsubstituted morpholinyl;
$R^6$ and $R^7$ may be joined in a ring to form a carbocycle or a morpholine;
$R^7$ and $R^{7a}$ may be joined in a ring to form a carbocycle or a morpholine;
$R^8$ is independently selected from hydrogen, $C_1$–$C_6$ alkyl, 2,2,2-trifluoroethyl, benzyl and aryl;
$R^9$ is independently selected from $C_1$–$C_6$ alkyl and aryl;
$R^{10}$ is selected from: H; $R^8C(O)$—; $R^9S(O)_m$—; unsubstituted or substituted $C_{1-4}$ alkyl, wherein the substituted alkyl group is substituted with one or two substituents selected from:
a) $C_{1-4}$ alkoxy,
b) aryl,
c) halogen,
d) HO, e) 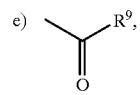

f) 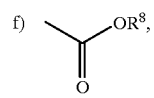

g) —$S(O)_mR^9$, h) $N(R^8)_2$, or
i) $C_{3-6}$ cycloalkyl;
X is a bond, —$C(=O)NR^{10}$—, —$NR^{10}C(=O)$—, —$S(O)_m$— or $NR^{10}$—;

| | |
|---|---|
| n is | 0 or 1; |
| m is | 0, 1 or 2; |
| p is | 0, 1, 2, 3 or 4, provided that p is not 0 if X is a bond or —$NR^{10}$—; and |
| q is | 0 or 1. | or an optical isomer or pharmaceutically acceptable salt thereof.

7. The compound according to claim 5, which inhibits farnesyl-protein transferase, of the formula F:

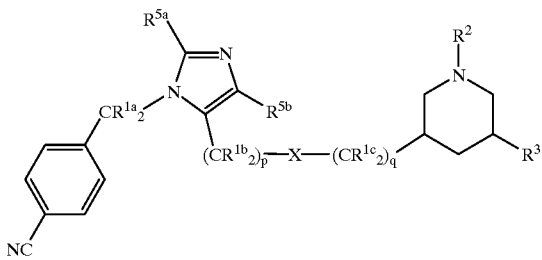

wherein:
$R^{1a}$ and $R^{1c}$ are independently selected from: hydrogen, $C_3$–$C_{10}$ cycloalkyl or $C_1$–$C_6$ alkyl;

$R^{1b}$ is independently selected from:
a) hydrogen,
b) aryl, $C_3$–$C_{10}$ cycloalkyl, $R^8O$—, —$N(R^8)_2$ or F,
c) $C_1$–$C_6$ alkyl unsubstituted or substituted by aryl, $C_3$–$C_{10}$ cycloalkyl, $R^8O$—, or —$N(R^8)_2$;

$R^2$ is selected from: H; unsubstituted or substituted $C_{1\text{-}8}$ alkyl, unsubstituted or substituted aryl,

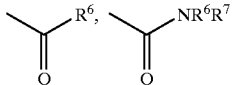

and —$S(O)_2R^6$,
wherein the substituted group is substituted with one or more of:
1) aryl or morpholinyl, unsubstituted or substituted with one or two groups selected from:
   a) $C_{1\text{-}4}$ alkyl,
   b) $(CH_2)_pOR^6$,
   c) $(CH_2)_pNR^6R^7$,
   d) halogen,
   e) $C_{1\text{-}4}$ perfluoroalkyl,
2) $C_{3\text{-}6}$ cycloalkyl,
3) $OR^6$,
4) $SR^6$, $S(O)R^6$, $SO_2R^6$,

5) —$NR^6R^7$,

6) 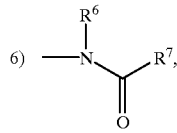

7) 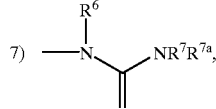

8) 

9) 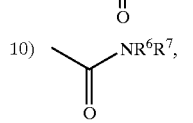

10) 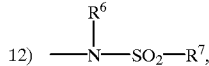

11) —$SO_2$—$NR^6R^7$,

12) 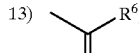

13) 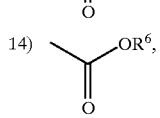

14) 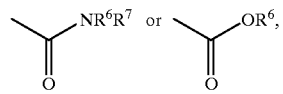

15) $C_{1\text{-}8}$alkyl, or
16) $C_{1\text{-}8}$ perfluoroalkyl,
provided $R^2$ comprises a morpholinyl group if $R^3$ does not comprise a morpholinyl group;

$R^3$ is selected from: H;

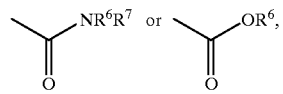

provided $R^3$ comprises a morpholinyl group if $R^2$ does not comprise a morpholinyl group;

$R^{5a}$ and $R^{5b}$ are independently hydrogen, ethyl, cyclopropyl or methyl;

$R^6$, $R^7$ and $R^{7a}$ are independently selected from: H; $C_{1\text{-}4}$ alkyl, $C_{3\text{-}6}$ cycloalkyl, aryl, morpholinyl, unsubstituted or substituted with:
a) $C_{1\text{-}4}$ alkoxy,
b) halogen, or
c) substituted or unsubstituted aryl or substituted or unsubstituted morpholinyl, $R^6$ and $R^7$ may be joined in a ring to form a carbocycle or a morpholine;

$R^7$ and $R^{7a}$ may be joined in a ring to form a carbocycle or a morpholine;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1\text{-}4}$ alkyl, wherein the substituted alkyl group is substituted with one or two substituents selected from:
a) $C_{1\text{-}4}$ alkoxy,
b) aryl,
c) halogen,
d) HO, e) 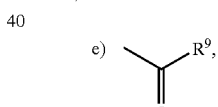

f) 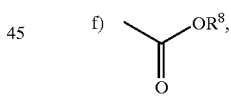

g) —$S(O)_mR^9$, h) $N(R^8)_2$, or i) $C_{3\text{-}6}$ cycloalkyl;

X is a bond, —$C(=O)NR^{10}$—, —$NR^{10}C(=O)$—, —$S(O)_m$— or —$NR^{10}$—;

| | |
|---|---|
| m is | 0, 1 or 2; |
| p is | 0, 1, 2, 3 or 4; and |
| q is | 0 or 1; | or an optical isomer or pharmaceutically acceptable salt thereof.

8. The compound according to claim 6, which inhibits farnesyl-protein transferase, of the formula G:

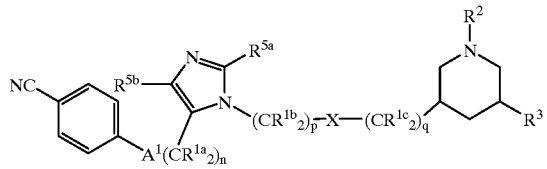

wherein:

$R^{1a}$ and $R^{1c}$ are independently selected from: hydrogen, $R^8O-$, $-N(R^8)_2$, F, $C_3-C_{10}$ cycloalkyl or $C_1-C_6$ alkyl;

$R^{1b}$ is independently selected from:
a) hydrogen,
b) aryl or $C_3-C_{10}$ cycloalkyl,
c) $C_1-C_6$ alkyl unsubstituted or substituted by aryl, $C_3-C_{10}$ cycloalkyl, $C_2-C_6$ alkenyl, $R^8O-$, or $-N(R^8)_2$;

$R^2$ is selected from: H; unsubstituted or substituted $C_{1-8}$ alkyl, unsubstituted or substituted aryl,

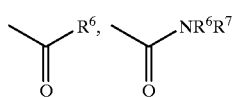

and $-S(O)_2R^6$, wherein the substituted group is substituted with one or more of:

1) aryl or morpholinyl, unsubstituted or substituted with one or two groups selected from:
   a) $C_{1-4}$ alkyl,
   b) $(CH_2)_pOR^6$,
   c) $(CH_2)_pNR^6R^7$,
   d) halogen,
   e) $C_{1-4}$ perfluoroalkyl,
2) $C_{3-6}$ cycloalkyl,
3) $OR^6$,
4) $SR^6$, $S(O)R^6$, $SO_2R^6$,

5) $-NR^6R^7$,

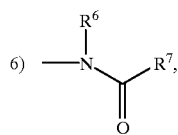

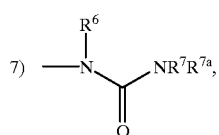

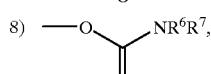

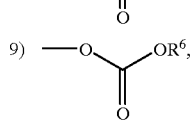

10) 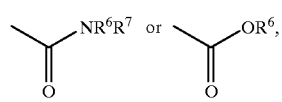

11) $-SO_2-NR^6R^7$, 12) (structure with $R^6$, N, $SO_2-R^7$)

13) (acyl with $R^6$)

14) (acyl with $OR^6$)

15) $C_{1-8}$ alkyl, or
16) $C_{1-8}$ perfluoroalkyl, provided $R^2$ comprises a morpholinyl group if $R^3$ does not comprise a morpholinyl group;

$R^3$ is selected from: H;

(structures: $-C(O)NR^6R^7$ or $-C(O)OR^6$)

provided $R^3$ comprises a morpholinyl group if $R^2$ does not comprise a morpholinyl group;

$R^{5a}$ and $R^{5b}$ are independently hydrogen, ethyl, cyclopropyl or methyl;

$R^6$, $R^7$ and $R^{7a}$ are independently selected from: H; $C_{1-4}$ alkyl, $C_{3-6}$ cycloalkyl, aryl, morpholinyl, unsubstituted or substituted with:
   a) $C_{1-4}$ alkoxy,
   b) halogen, or
   c) substituted or unsubstituted aryl or substituted or unsubstituted morpholinyl;

$R^6$ and $R^7$ may be joined in a ring to form a carbocycle or a morpholine;

$R^7$ and $R^{7a}$ may be joined in a ring to form a carbocycle or a morpholine;

$R^8$ is independently selected from hydrogen, $C_1-C_6$ alkyl, 2,2,2-trifluoroethyl, benzyl and aryl;

$R^9$ is independently selected from $C_1-C_6$ alkyl and aryl;

$R^{10}$ is selected from: H; $R^8C(O)-$; $R^9S(O)_m-$; unsubstituted or substituted $C_{1-4}$ alkyl, wherein the substituted alkyl group is substituted with one or two substituents selected from:
   a) $C_{1-4}$ alkoxy,
   b) aryl,
   c) halogen,
   d) HO, e) (acyl with $R^9$), f) (acyl with $OR^8$), -continued g) —S(O)$_m$R$^9$, h) N(R$^8$)$_2$, or i) C$_{3-6}$ cycloalkyl;

A$^1$ is selected from: a bond, —C(O)—, O, —N(R$^8$)—, or S(O)$_m$;

X is a bond, —C(=O)NR$^{10}$—, —NR$^{10}$C(=O)—, —S(O)$_m$— or —NR$^{10}$;

| | |
|---|---|
| m is | 0, 1 or 2; |
| n is | 0 or 1; |
| p is | 1, 2 or 3; and |
| q is | 0 or 1; | or an optical isomer or pharmaceutically acceptable salt thereof.

9. A compound which inhibits farnesyl-protein transferase which is:

1-Phenethyl-cis-3-[N-(1-morpholinyl)carbamyl]-5-[N-(1-(4-cyanobenzyl-1H-imidazol-5-ylethyl)carbamoyl]piperidine, 1-(2,2-Diphenylethyl)-cis-3-[N-(1-morpholinyl)carbamyl]-5-[N-(1-(4-cyanobenzyl-1H-imidazol-5-ylethyl)carbamoyl]piperidine, or 1-(2-(1-Morpholinyl)-2-phenylethyl)-3(S)-[N-(1-(4-cyanobenzyl)-1H-imidazol-5-ylethyl)carbamoyl]piperidine, or an optical isomer or a pharmaceutically acceptable salt thereof.

10. The compound according to claim 9 which is:

1-Phenethyl-cis-3-[N-(1 morpholinyl)carbamyl]-5-[N-(4-cyanobenzyl-1-imidazole-5-ylethyl)carbamyl]piperidine

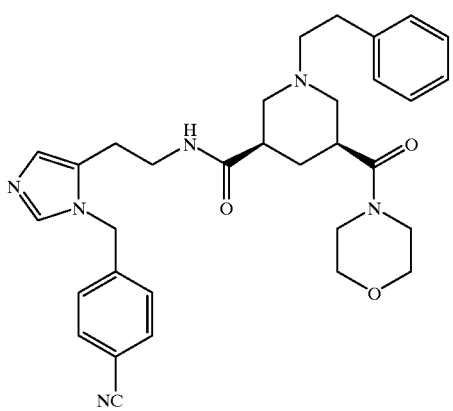

or an optical isomer or a pharmaceutically acceptable salt thereof.

11. The compound according to claim 9 which is:

1-(2,2-Diphenylethyl)-cis-3-[N-(1-morpholinyl)carbamyl]-5-[N-(4-cyanobenzyl-1H-imidazole-5-ylethyl)carbamyl]piperidine

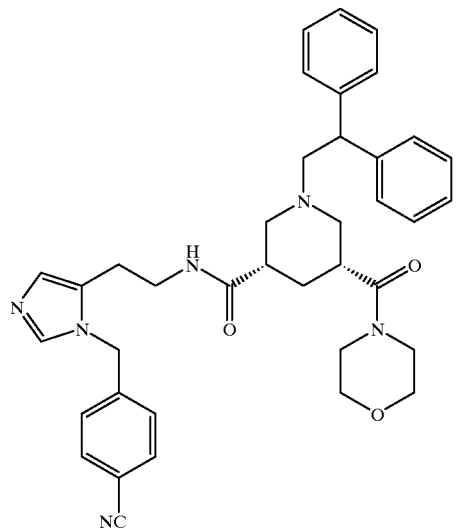

or an optical isomer or a pharmaceutically acceptable salt thereof.

12. The compound according to claim 9 which is:

1-(2-(1-Morpholinyl)-2-phenylethyl)-3(S)-[N-(1-(4-cyanobenzyl)-1H-imidazol-5-ylethyl)carbamoyl]piperidine

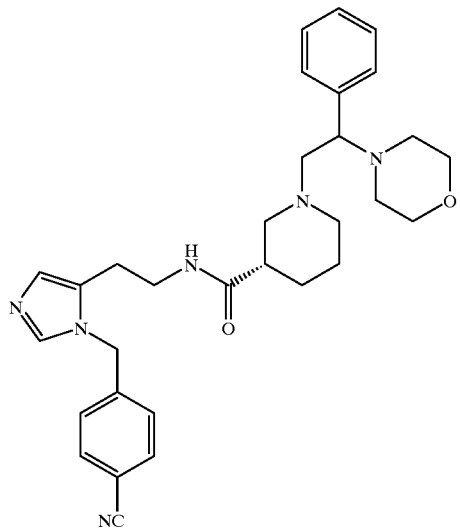

or an optical isomer or a pharmaceutically acceptable salt thereof.

13. A pharmaceutical composition comprising a pharmaceutical carrier, and dispersed therein, a therapeutically effective amount of a compound of claim 1.

14. A pharmaceutical composition comprising a pharmaceutical carrier, and dispersed therein, a therapeutically effective amount of a compound of claim 5.

15. A pharmaceutical composition comprising a pharmaceutical carrier, and dispersed therein, a therapeutically effective amount of a compound of claim 6.

16. A pharmaceutical composition comprising a pharmaceutical carrier, and dispersed therein, a therapeutically effective amount of a compound of claim 9.

17. A pharmaceutical composition made by combining the compound of claim 1 and a pharmaceutically acceptable carrier.

18. A process for making a pharmaceutical composition comprising combining a compound of claim 1 and a pharmaceutically acceptable carrier.

19. A method for treating cancer by inhibiting farnesyl-protein transferase which comprises administering to a mammal in need thereof a therapeutically effective amount of a composition of claim 13.

20. A method for treating cancer by inhibiting farnesyl-protein transferase which comprises administering to a mammal in need thereof a therapeutically effective amount of a composition of claim 14.

21. A method for treating cancer by inhibiting farnesyl-protein transferase which comprises administering to a mammal in need thereof a therapeutically effective amount of a composition of claim 15.

22. A method for treating cancer by inhibiting farnesyl-protein transferase which comprises administering to a mammal in need thereof a therapeutically effective amount of a composition of claim 16.

* * * * *